(12) United States Patent
Vågberg et al.

(10) Patent No.: US 11,339,183 B2
(45) Date of Patent: *May 24, 2022

(54) PHOSPHATE AND PHOSPHONATE DERIVATIVES OF 7-AMINO-5-THIO-THIAZOLO[4,5-D] PYRIMIDINES AND THEIR USE IN TREATING CONDITIONS ASSOCIATED WITH ELEVATED LEVELS OF CX3CR1 AND/OR CX3CL1

(71) Applicant: KANCERA AB, Banvaktsvagen (SE)

(72) Inventors: Jan Vågberg, Sollentuna (SE); Styrbjörn Byström, Täby (SE); Elisabeth Olsson, Sollentuna (SE); Mattias Jönsson, Knivsta (SE)

(73) Assignee: KANCERA AB, Banvaktsvagen (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/372,125

(22) Filed: Jul. 9, 2021

(65) Prior Publication Data

US 2021/0340167 A1    Nov. 4, 2021

Related U.S. Application Data

(63) Continuation of application No. 17/257,917, filed as application No. PCT/EP2019/068169 on Jul. 5, 2019.

(30) Foreign Application Priority Data

Jul. 6, 2018 (GB) ...................................... 1811169

(51) Int. Cl.
| | |
|---|---|
| *C07F 9/6561* | (2006.01) |
| *A61K 9/08* | (2006.01) |
| *A61K 31/685* | (2006.01) |
| *A61K 31/70* | (2006.01) |
| *A61K 45/06* | (2006.01) |

(52) U.S. Cl.
CPC ............. *C07F 9/6561* (2013.01); *A61K 9/08* (2013.01); *A61K 31/685* (2013.01); *A61K 31/70* (2013.01); *A61K 45/06* (2013.01)

(58) Field of Classification Search
None
See application file for complete search history.

(56) References Cited

U.S. PATENT DOCUMENTS

2021/0292349 A1*  9/2021  Vågberg et al. .......... A61P 9/10

FOREIGN PATENT DOCUMENTS

| WO | WO 2005/033115 | 4/2005 |
|---|---|---|
| WO | WO 2006/107257 | 10/2006 |
| WO | WO 2006/107258 | 10/2006 |
| WO | WO 2008/005555 | 1/2008 |
| WO | WO 2008/039138 | 4/2008 |
| WO | WO 2008/039139 | 4/2008 |
| WO | WO 2009/120140 | 10/2009 |
| WO | WO 2016/200939 | 12/2016 |

OTHER PUBLICATIONS

International Preliminary Report on Patentability issued in International Application No. PCT/EP2019/068169, dated Jan. 12, 2021.
International Search Report and Written Opinion issued in International Application No. PCT/EP2019/068169, dated Aug. 29, 2019.
Karlstrom, et al. "Substituted 7-amino-5-thio-thiazolo [4, 5-d] pyrimidines as potent and selective antagonists of the fractalkine receptor (CX3CR1)." *Journal of Medicinal Chemistry* 56.8 (2013): 3177-3190.

* cited by examiner

*Primary Examiner* — Jeffrey S Lundgren
*Assistant Examiner* — Michael J Schmitt
(74) *Attorney, Agent, or Firm* — Parker Highlander PLLC

(57) ABSTRACT

There is provided a compound of formula I,

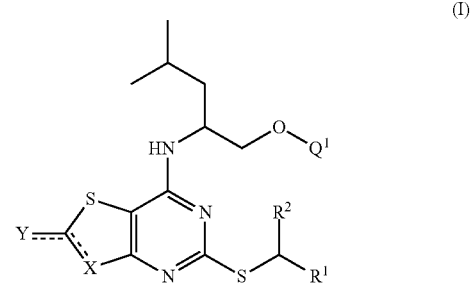

wherein $R^1$, $R^2$, $Q^1$ and

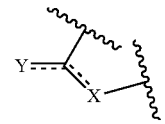

are as defined herein, which compounds are useful in the treatment of diseases and disorders associated with elevated levels of CX3CR1 and/or CX3CL1, in particular acute and/or chronic inflammation, eye diseases, lung diseases, skin diseases, joint and/or bone diseases, autoimmune diseases, cardiovascular diseases, metabolic diseases, brain diseases, neurodegenerative diseases, pain, cancer, liver diseases, kidney diseases, gastrointestinal diseases, human immunodeficiency virus and mood disorders.

17 Claims, No Drawings

PHOSPHATE AND PHOSPHONATE DERIVATIVES OF 7-AMINO-5-THIO-THIAZOLO[4,5-D] PYRIMIDINES AND THEIR USE IN TREATING CONDITIONS ASSOCIATED WITH ELEVATED LEVELS OF CX3CR1 AND/OR CX3CL1

This application is a continuation of U.S. application Ser. No. 17/257,917, filed Jan. 5, 2021, as a national phase application under 35 U.S.C. § 371 of International Application No. PCT/EP2019/068169, filed Jul. 5, 2019, which claims priority to United Kingdom Application No. 1811169.0, filed Jul. 6, 2018. The entire text of each of the above referenced disclosures is specifically incorporated herein by reference.

FIELD OF THE INVENTION

This invention relates to novel pharmaceutically-active compounds, to pharmaceutical compositions comprising such compounds, as well as to their pharmaceutical use. In particular, the invention relates to antagonists of the fractalkine receptor and their use in the treatment of diseases and disorders associated with elevated levels of CX3CR1 and/or CX3CL1.

BACKGROUND OF THE INVENTION

The listing or discussion of an apparently prior-published document in this specification should not necessarily be taken as an acknowledgement that the document is part of the state of the art or is common general knowledge.

7-Amino-5-thio-thiazolo[4,5-d]pyrimidines, such as (2R)-2-[(2-amino-5-{[(1S)-1-phenylethyl]thio}[1,3]thiazolo[4,5-d]pyrimidin-7-yl)amino]-4-methylpentan-1-ol (A) and 5-{[(1S)-1-(5-chloropyridin-2-yl)ethyl]sulfanyl}-7-{[(1R)-1-(hydroxymethyl)-3-methylbutyl]amino}[1,3]thiazolo[4,5-d]pyrimidin-2(3H)-one (B) are known to be antagonists of the fractalkine receptor (Karlström et al. *J. Med. Chem.*, 2013, 56, 3177-3190).

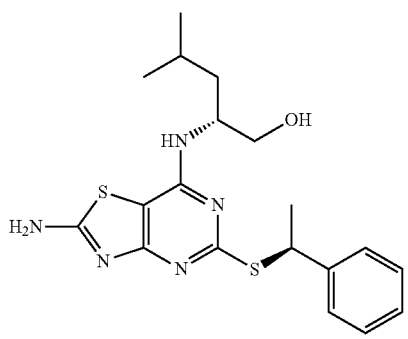

(A)

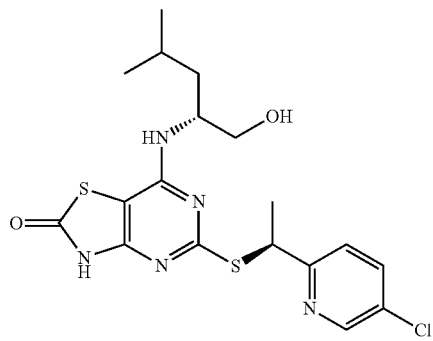

(B)

However, these compounds are poorly-water soluble, making formulating suitable pharmaceutical dosage forms a considerable challenge.

DETAILED DESCRIPTION OF THE INVENTION

It has now surprisingly been found that certain phosphate derivatives of compounds such as compounds A and B offer several advantages over the known fractalkine receptor antagonists. In addition to markedly improved aqueous solubility, the compounds are also considerably more stable to long-term storage under aqueous conditions, and achieve higher blood plasma concentrations than administering the known compounds.

Without wishing to be bound by theory, it is believed that, as a result of the higher blood plasma concentrations achieved by these compounds, there is reason to believe that they are likely to put less stress on the liver during first-pass metabolism after peroral administration compared to administering the known antagonists. Therefore, the compounds may be better tolerated at higher dosages and/or for longer term treatment than known fractalkine receptor antagonists.

In a first aspect of the invention, there is provided a compound of formula I,

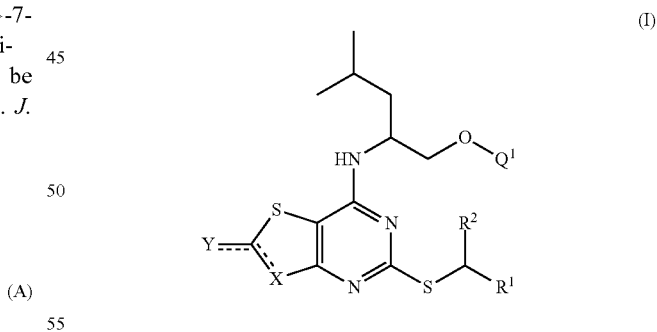

(I)

wherein $R^1$ represents aryl (e.g. phenyl) or pyridyl, both of which are optionally substituted by one or more groups selected from halo, —CN, —C(O)NR$^3$R$^4$, —S(O)$_2$R$^5$, $C_{1-6}$ alkyl, $C_{2-6}$ alkenyl or $C_{2-6}$ alkynyl, wherein the latter three groups are optionally substituted by one or more F;

$R^2$ represents H or $C_{1-6}$ alkyl optionally substituted by one or more F;

$R^3$ and $R^4$ each independently represent H or $C_{1-6}$ alkyl optionally substituted by one of more F;

$R^5$ represents $C_{1-6}$ alkyl optionally substituted by one or more F;

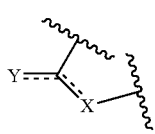

represents

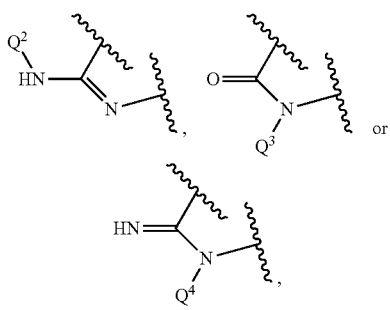

wherein " ∼∼∼ " indicates a point of attachment to the rest of the molecule;

$Q^1$ and $Q^2$ each independently represent H or —PO(OR$^6$)(OR$^7$);

$Q^3$ represents H or —CH$_2$OPO(OR$^6$)(OR$^7$); and $Q^4$ represents —CH$_2$OPO(OR$^6$)(OR$^7$);

wherein $R^6$ and $R^7$ each independently represent H, C$_{1-4}$ alkyl or C$_{2-4}$ alkenyl;

wherein at least one of $Q^1$, and $Q^2$, $Q^3$ or $Q^4$ represents —PO(OR$^6$)(OR$^7$) or —CH$_2$OPO(OR$^6$)(OR$^7$);

or a pharmaceutically-acceptable salt thereof, which compounds (including pharmaceutically acceptable salts) may be referred to herein as the "compounds of the invention".

For the avoidance of doubt, the skilled person will understand that references herein to compounds of particular aspects of the invention (such as the first aspect of the invention, i.e. referring to compounds of formula I as defined in the first aspect of the invention) will include references to all embodiments and particular features thereof, which embodiments and particular features may be taken in combination to form further embodiments and features of the invention.

Unless indicated otherwise, all technical and scientific terms used herein will have their common meaning as understood by one of ordinary skill in the art to which this invention pertains.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Particular acid addition salts that may be mentioned include those formed by reaction with corresponding acids, thus protonating the compound of the invention, to form carboxylate salts (e.g. formate, acetate, trifluoroacetate, propionate, isobutyrate, heptanoate, decanoate, caprate, capry- late, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulphonate salts (e.g. benzenesulphonate, methyl-, bromo- or chloro-benzenesulphonate, xylenesulphonate, methanesulphonate, ethanesulphonate, propanesulphonate, hydroxy-ethanesulphonate, 1- or 2-naphthalene-sulphonate or 1,5-naphthalene-disulphonate salts) or sulphate, pyrosulphate, bisulphate, sulphite, bisulphite, phosphate, monohydrogenphosphate, dihydrogenphosphate, metaphosphate, pyrophosphate or nitrate salts, and the like.

Particular base addition salts that may be mentioned include salts formed by reaction with corresponding bases, thus removing a proton from compounds of the invention, to form salts with alkali metals (such as Na and K salts), alkaline earth metals (such as Mg and Ca salts), organic bases (such as ethanolamine, diethanolamine, triethanolamine and tromethamine) and inorganic bases (such as ammonia).

More particular salts that may be mentioned include Li, Na, K and ammonium salts (including monosalts and disalts). In particular, for compounds of the invention wherein $R^6$ and $R^7$ each represent H particular salts that may be mentioned include diammonium salts, disodium salts, dilithium salts and dipotassium salts.

For the avoidance of doubt, compounds of the invention may exist as solids, and thus the scope of the invention includes all amorphous, crystalline and part crystalline forms thereof, and may also exist as oils. Where compounds of the invention exist in crystalline and part crystalline forms, such forms may include solvates, which are included in the scope of the invention.

For the avoidance of doubt, compounds of the invention may also exist in solution (i.e. in solution in a suitable solvent). For example, compounds of the invention may exist in aqueous solution, in which case compounds of the invention may exist in the form of hydrates thereof.

Compounds of the invention may contain double bonds and, unless otherwise indicated, may thus exist as E (entgegen) and Z (zusammen) geometric isomers about each individual double bond. Unless otherwise specified, all such isomers and mixtures thereof are included within the scope of the invention.

Compounds of the invention may also exhibit tautomerism. All tautomeric forms and mixtures thereof are included within the scope of the invention (particularly those of sufficient stability to allow for isolation thereof).

Compounds of the invention may also contain one or more asymmetric carbon atoms and may therefore exhibit optical and/or diastereoisomerism (i.e. existing in enantiomeric or diastereomeric forms). Diastereoisomers may be separated using conventional techniques, e.g. chromatography or fractional crystallisation. The various stereoisomers (i.e. enantiomers) may be isolated by separation of a racemic or other mixture of the compounds using conventional, e.g. fractional crystallisation or HPLC techniques. Alternatively the desired enantiomer or diastereoisomer may be obtained from appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution; for example, with a homochiral acid followed by separation of the diastereomeric derivatives by conventional means such as chromatography), or by reaction with an appropriate chiral reagent or chiral catalyst, all of which methods and processes may be performed under conditions known to the skilled person. Unless otherwise specified, all stereoisomers and mixtures thereof are included within the scope of the invention.

Unless otherwise specified, C-z alkyl groups (where z is the upper limit of the range) defined herein may be straight-chain or, when there is a sufficient number (i.e. a minimum of two or three, as appropriate) of carbon atoms, be branched-chain, and/or cyclic (so forming a $C_{3-z}$ cycloalkyl group). When there is a sufficient number (i.e. a minimum of four) of carbon atoms, such groups may also be part cyclic (so forming a $C_{4-z}$ partial cycloalkyl group). For example, cycloalkyl groups that may be mentioned include cyclopropyl, cyclopentyl and cyclohexyl. Similarly, part cyclic alkyl groups (which may also be referred to as "part cycloalkyl" groups) that may be mentioned include cyclopropylmethyl. When there is a sufficient number of carbon atoms, such groups may also be multicyclic (e.g. bicyclic or tricyclic) and/or spirocyclic. For the avoidance of doubt, particular alkyl groups that may be mentioned include straight chain (i.e. not branched and/or cyclic) alkyl groups.

Unless otherwise specified, $C_{2-z}$ alkenyl groups (where z is the upper limit of the range) defined herein may be straight-chain or, when there is a sufficient number (i.e. a minimum of three) of carbon atoms, be branched-chain, and/or cyclic (so forming a $C_{4-z}$ cycloalkenyl group). When there is a sufficient number (i.e. a minimum of five) of carbon atoms, such groups may also be part cyclic. For example, part cyclic alkenyl groups (which may also be referred to as "part cycloalkenyl" groups) that may be mentioned include cyclopentenylmethyl and cyclohexenylmethyl. When there is a sufficient number of carbon atoms, such groups may also be multicyclic (e.g. bicyclic or tricyclic) or spirocyclic. For the avoidance of doubt, particular alkenyl groups that may be mentioned include straight chain (i.e. not branched and/or cyclic) alkenyl groups.

Unless otherwise specified, $C_{2-z}$ alkynyl groups (where z is the upper limit of the range) defined herein may be straight-chain or, when there is a sufficient number (i.e. a minimum of four) of carbon atoms, be branched-chain. For the avoidance of doubt, particular alkynyl groups that may be mentioned include straight chain (i.e. not branched and/or cyclic) alkynyl groups.

For the avoidance of doubt, unless otherwise specified, groups referred to herein as "alkyl", "alkenyl" and/or "alkynyl" will be taken as referring to the highest degree of unsaturation in a bond present in such groups. For example, such a group having a carbon-carbon double bond and, in the same group, a carbon-carbon triple bond will be referred to as "alkynyl". Alternatively, it may be particularly specified that that such groups will comprise only the degree of unsaturation specified (i.e. in one or more bond therein, as appropriate; e.g. in in one bond therein).

For the avoidance of doubt, alkyl, alkenyl and alkynyl groups as described herein may also act as linker groups (i.e. groups joining two or more parts of the compound as described), in which case such groups may be referred to as "alkylene", "alkenylene" and/or "alkynylene" groups, respectively.

As may be used herein, the term aryl may refer to $C_{6-14}$ (e.g. $C_{6-10}$) aromatic groups. Such groups may be monocyclic or bicyclic and, when bicyclic, be either wholly or partly aromatic. $C_{6-10}$ aryl groups that may be mentioned include phenyl, naphthyl, 1,2,3,4-tetrahydronaphthyl, indanyl, and the like (e.g. phenyl, naphthyl, and the like). For the avoidance of doubt, the point of attachment of substituents on aryl groups may be via any suitable carbon atom of the ring system.

For the avoidance of doubt, the skilled person will understand that aryl groups that may form part of compounds of the invention are those that are chemically obtainable, as known to those skilled in the art. Particular aryl groups that may be mentioned include phenyl and naphthyl, such as phenyl.

For the avoidance of doubt, references to polycyclic (e.g. bicyclic or tricyclic) groups (for example when employed in the context of heterocyclyl or cycloalkyl groups (e.g. heterocyclyl)) will refer to ring systems wherein at least two scissions would be required to convert such rings into a non-cyclic (i.e. straight or branched) chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of alkyl groups) may refer to groups in which the second ring of a two-ring system is formed between two adjacent atoms of the first ring, to groups in which two non-adjacent atoms are linked by an alkyl (which, when linking two moieties, may be referred to as alkylene) group (optionally containing one or more heteroatoms), which later groups may be referred to as bridged, or to groups in which the second ring is attached to a single atom, which latter groups may be referred to as spiro compounds.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. compounds of the invention in which one or more hydrogen atoms are replaced by the hydrogen isotope deuterium.

Further for the avoidance of doubt, when it is specified that a substituent is itself optionally substituted by one or more substituents (e.g. $C_{1-3}$ alkyl optionally substituted by one or more F), these substituents where possible may be positioned on the same or different atoms. Such optional substituents may be present in any suitable number thereof (e.g. the relevant group may be substituted with one or more such substituents, such as one such substituent).

For the avoidance of doubt, where groups are referred to herein as being optionally substituted it is specifically contemplated that such optional substituents may be not present (i.e. references to such optional substituents may be removed), in which case the optionally substituted group may be referred to as being unsubstituted.

Where used herein, a wavy bond (i.e. "〜", or the like) may indicate a (or the) point of attachment of the relevant substituent to the core molecule (i.e. the compound of the compound of formula I to which the substituent is attached).

For the avoidance of doubt, the skilled person will appreciate that compounds of the invention that are the subject of this invention include those that are obtainable, i.e. those that may be prepared in a stable form. That is, compounds of the invention include those that are sufficiently robust to survive isolation, e.g. from a reaction mixture, to a useful degree of purity.

In particular embodiments of the compounds of the invention that may be mentioned, $R^1$ represents phenyl or pyridyl, both of which are optionally substituted by one or more (e.g. one) fluoro, chloro, bromo, —CN, —C(O)NR$^3$R$^4$, —S(O)$_2$R$^5$, C$_{1-4}$ alkyl (for example C$_{1-3}$ alkyl, e.g. C$_{1-2}$ alkyl), C$_{2-6}$ alkenyl (for example C$_{2-3}$ alkenyl, e.g. ethenyl) or C$_{2-4}$ alkynyl (for example C$_{2-3}$ alkenyl, e.g. ethynyl) wherein the latter three groups are optionally substituted by one or more F, wherein $R^3$, $R^4$ and $R^5$ are as defined herein.

In further particular embodiments, $R^1$ represents phenyl or pyridyl, both of which are optionally substituted by one or more fluoro, chloro, bromo, —CN, —C(O)NR$^3$R$^4$ or —S(O)$_2$Me group, wherein $R^3$ and $R^4$ are as defined herein.

In further particular embodiments, $R^1$ represents phenyl or pyridyl, both of which are optionally substituted by one or more (e.g. one) fluoro, chloro, bromo or methyl group.

In further particular embodiments, $R^1$ represents phenyl or pyridyl, both of which are optionally substituted by one or more (e.g. one) fluoro, chloro or bromo group.

In further particular embodiments, $R^1$ is selected from

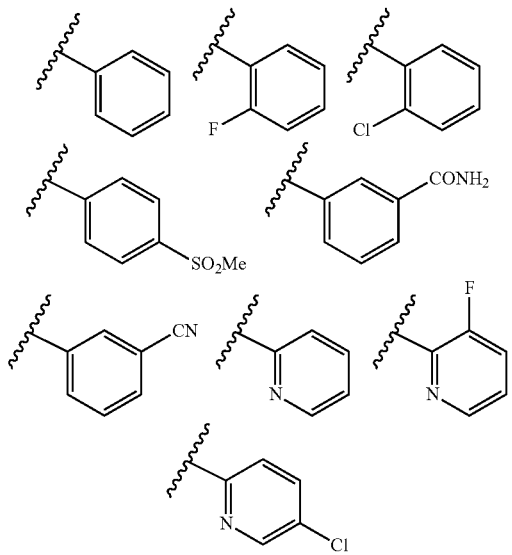

wherein " ∿ " indicates the point of attachment to the rest of the molecule.

In further particular embodiments, $R^1$ represents phenyl or pyridyl, both of which are optionally substituted by one or more (e.g. one) chloro group.

In more particular embodiments, $R^1$ represents phenyl (i.e. unsubstituted) or 5-chloropyridin-2-yl (e.g. phenyl).

In particular embodiments, $R^2$ represents C$_{1-6}$ alkyl optionally substituted by one or more F.

In particular embodiments, $R^2$ represents C$_{1-6}$ alkyl (i.e. unsubstituted). In more particular embodiments $R^2$ represents C$_{1-3}$ alkyl optionally substituted by one or more F (e.g. unsubstituted). In yet more particular embodiments, $R^2$ represents trifluoromethyl, difluoromethyl, fluoromethyl or, particularly, methyl.

In further particular embodiments, $R^2$ represents H or, particularly, methyl.

In particular embodiments, $R^3$ and $R^4$ each independently represent H or C$_{1-6}$ alkyl (i.e. unsubstituted). In more particular embodiments, $R^3$ and $R^4$ each independently represent C$_{1-3}$ alkyl optionally substituted by one or more F (e.g. unsubstituted). In yet more particular embodiments, $R^3$ and $R^4$ each independently represent H, trifluoromethyl, difluoromethyl, fluoromethyl or methyl. In further particular embodiments $R^3$ and $R^4$ both represent H.

In particular embodiments, $R^5$ represents C$_{1-6}$ alkyl (i.e. unsubstituted). In more particular embodiments $R^5$ represents C$_{1-3}$ alkyl optionally substituted by one or more F (e.g. unsubstituted). In yet more particular embodiments, $R^5$ represents trifluoromethyl, difluoromethyl, fluoromethyl or, particularly, methyl.

In the compounds of the invention, at least one of $Q^1$ and $Q^2$, $Q^3$ or $Q^4$ (i.e. at least one of $Q^1$ and $Q^2$; or $Q^1$ and $Q^3$; or $Q^1$ and $Q^4$, as appropriate) represents —PO(OR$^6$)(OR$^7$) or —CH$_2$OPO(OR$^6$)(OR$^7$). Thus, compounds of the invention may contain one or two phosphate or phosphoamidic acid groups or esters thereof (—OPO(OR$^6$)(OR$^7$) or —NHPO(OR$^6$)(OR$^7$)/—NR$^x$PO(OR$^6$)(OR$^7$), wherein R$^x$ represents a carbon-based group (e.g. alkyl)) groups (i.e. one or two of $Q^1$ and $Q^2$, $Q^3$ or $Q^4$ may represent —PO(OR$^6$)(OR$^7$) or —CH$_2$OP(OR$^6$)(OR$^7$) (as appropriate)). If one of $Q^1$ and $Q^2$, $Q^3$ or $Q^4$ represents —PO(OR$^6$)(OR$^7$) or —CH$_2$OP(OR$^6$)(OR$^7$), the remaining group represents H.

In more particular embodiments, one of $Q^1$ and $Q^2$, $Q^3$ or $Q^4$ represents —PO(OR$^6$)(OR$^7$) or —CH$_2$OPO(OR$^6$)(OR$^7$), and the remainder of $Q^1$, and (if present) $Q^2$ or $Q^3$ represent H ($Q^4$ either represents —CH$_2$OPO(OR$^6$)(OR$^7$) or is absent).

Particular compounds of the invention that may be mentioned include those in which

represents

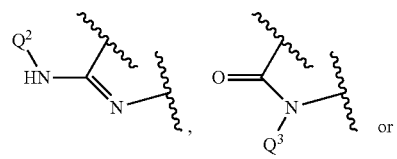, 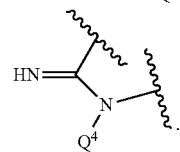 or

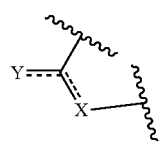.

Particular compounds of the invention that may be mentioned include those in which if represents

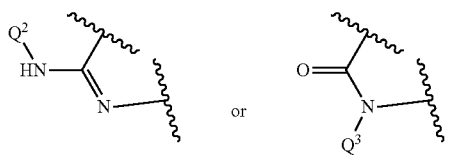 or one of $Q^1$ and $Q^2$ or $Q^3$ represents —PO(OR$^6$)(OR$^7$) or —CH$_2$OPO(OR$^6$)(OR$^7$) and the other of $Q^1$, and $Q^2$ or $Q^3$ represents H; and if

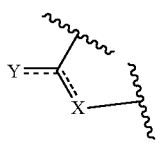

represents

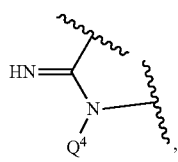, $Q^1$ represents H and $Q^4$ represents —CH$_2$OPO(OR$^6$)(OR$^7$).

In particular embodiments that may be mentioned,

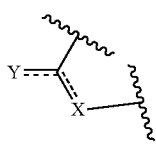

represents

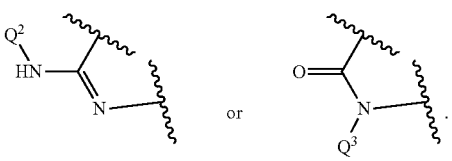.

In more particular embodiments,

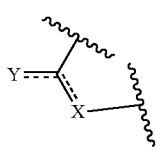

represents N

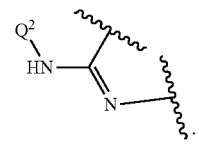.

In alternative particular embodiments,

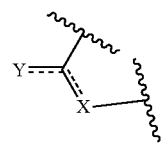

represents

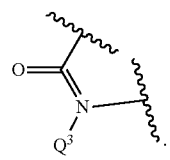.

In particular embodiments that may be mentioned, $Q^1$ represents —PO(OR$^6$)(OR$^7$).

In particular embodiments that may be mentioned,

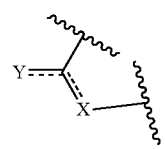

represents

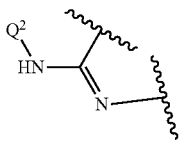 or 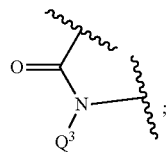;

and $Q^1$ represents —PO(OR$^6$)(OR$^7$).

In further particular embodiments in which

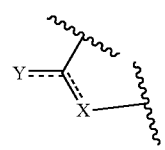

represents

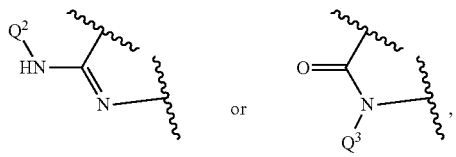 or $Q^1$ represents —PO(OR$^6$)(OR$^7$);

and $Q^2$ or $Q^3$ (as appropriate) each represent H.

In particular embodiments, $Q^1$ represents —PO(OR$^6$)(OR$^7$).

In particular embodiments, $Q^2$ represents —PO(OR$^6$)(OR$^7$).

In more particular embodiments in which

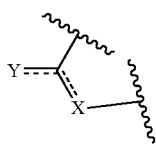

represents

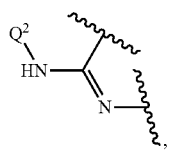, $Q^2$ represents —PO(OR$^6$)(OR$^7$); and $Q^1$ represents H.

In particular embodiments, $Q^3$ represents —CH$_2$PO(OR$^6$)(OR$^7$).

In more particular embodiments in which

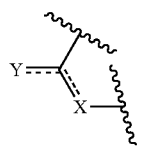

represents

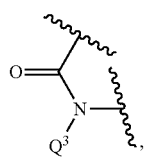, $Q^3$ represents —CH$_2$PO(OR$^6$)(OR$^7$); and $Q^1$ represents H.

In particular embodiments in which

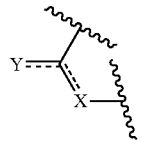

represents

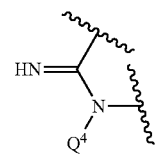

$Q^1$ represents H.

In particular embodiments, $Q^2$ represents H.

In particular embodiments $Q^3$ represents H.

In further particular embodiments, $Q^2$, $Q^3$ or $Q^4$ (as appropriate) represents H.

In particular embodiments that may be mentioned,
$Q^1$ represents —PO(OR$^6$)(OR$^7$) (e.g. —PO(OH)$_2$);

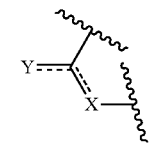

represents

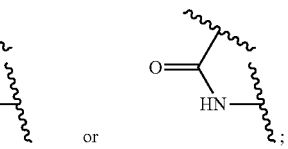;

or $Q^1$ represents H and

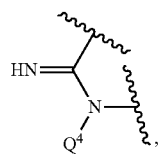

represents

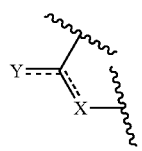, wherein, $Q^4$ represents —CH$_2$OPO(OR$^6$)(OR$^7$) (e.g. —CH$_2$OPO(OH)$_2$);

and $R^1$ and $R^2$ are as defined herein.

In particular embodiments that may be mentioned, $R^6$ and $R^7$ each independently represent $C_{1-3}$ alkyl (e.g. $C_{1-2}$ alkyl) or H. In more particular embodiments, $R^6$ and $R^7$ each represent H.

In further embodiments, $R^6$ and $R^7$ each represent methyl or each represent ethyl.

In further particular embodiments, $R^6$ represents iso-propyl and $R^7$ represents H.

In particular embodiments that may be mentioned, the compound of formula I is a compound of formula Ia,

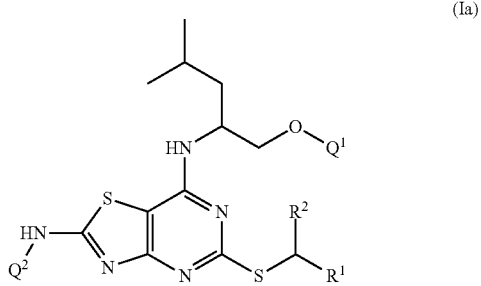

(Ia)

wherein $R^1$, $R^2$, $Q^1$ and $Q^2$ are as defined herein, or a pharmaceutically-acceptable salt thereof.

In particular embodiments of a compound of formula Ia that may be mentioned,
$Q^1$ represents —PO(OR$^6$)(OR$^7$);
$Q^2$ represents H;
$R^1$ represents phenyl or pyridyl both of which are optionally substituted by one or more (e.g. one) groups selected from the group consisting of chloro, fluoro, —CN, —CONH$_2$ and —SO$_2$Me (particularly phenyl (i.e. unsubstituted));
$R^2$ represents H or $C_{1-3}$ alkyl (e.g. methyl);
$R^6$ and $R^7$ each independently represent $C_{1-3}$ alkyl (e.g. Me) or H; more particularly $R^6$ represents iso-propyl and $R^7$ represents H or $R^6$ and $R^7$ each represent H (e.g. $R^6$ and $R^7$ each represent H).

In further particular embodiments of a compound of formula Ia that may be mentioned,
$Q^1$ represents —PO(OR$^6$)(OR$^7$);
$Q^2$ represents H;
$R^1$ represents phenyl or pyridyl both of which are optionally substituted by one or more (e.g. one) chloro (particularly phenyl (i.e. unsubstituted));
$R^2$ represents $C_{1-3}$ alkyl (e.g. methyl);
$R^6$ and $R^7$ each independently represent $C_{1-2}$ alkyl (e.g. Me) or particularly H.

In other particular embodiments of a compound of formula Ia,
$Q^1$ represents H;
$Q^2$ represents —PO(OR$^6$)(OR$^7$);
$R^1$ represents phenyl or pyridyl both of which are optionally substituted by one or more (e.g. one) groups selected from the group consisting of fluoro, chloro or —CN (particularly phenyl (i.e. unsubstituted));
$R^2$ represents $C_{1-3}$ alkyl (e.g. methyl);
$R^6$ and $R^7$ each independently represent $C_{1-3}$ alkyl (e.g. Me) or particularly H.

In further particular embodiments of a compound of formula Ia,
$Q^1$ represents H;
$Q^2$ represents —PO(OR$^6$)(OR$^7$);
$R^1$ represents phenyl or pyridyl both of which are optionally substituted by one or more (e.g. one) chloro (particularly phenyl (i.e. unsubstituted));
$R^2$ represents $C_{1-3}$ alkyl (e.g. methyl);
$R^6$ and $R^7$ each independently represent $C_{1-2}$ alkyl (e.g. Me) or particularly H.

In other particular embodiments that may be mentioned, the compound of formula I is a compound of formula Ib,

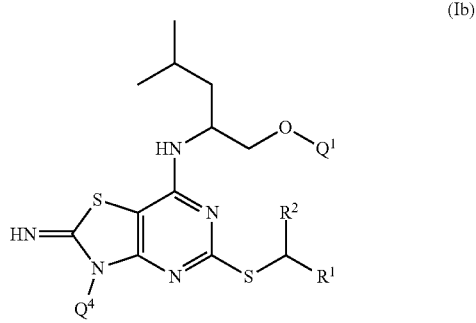

(Ib)

wherein $R^1$, $R^2$, $Q^1$ $Q^4$ are as defined herein, or a pharmaceutically-acceptable salt thereof.

In particular embodiments of a compound of formula Ib that may be mentioned,
$Q^4$ represents —CH$_2$OPO(OR$^6$)(OR$^7$);
$Q^1$ represents H;
$R^1$ represents phenyl or pyridyl both of which are optionally substituted by one or more (e.g. one) group selected from fluoro, chloro and —CN (particularly phenyl (i.e. unsubstituted));
$R^2$ represents $C_{1-3}$ alkyl (e.g. methyl); and
$R^6$ and $R^7$ each independently represent $C_{1-2}$ alkyl (e.g. Me) or particularly H.

In further particular embodiments of a compound of formula Ib that may be mentioned,
$Q^4$ represents —CH$_2$OPO(OR$^6$)(OR$^7$);
$Q^1$ represents H;
$R^1$ represents phenyl or pyridyl both of which are optionally substituted by one or more (e.g. one) chloro (particularly phenyl (i.e. unsubstituted));
$R^2$ represents $C_{1-3}$ alkyl (e.g. methyl); and
$R^6$ and $R^7$ each independently represent $C_{1-2}$ alkyl (e.g. Me) or particularly H.

In other particular embodiments that may be mentioned, the compound of formula I is a compound of formula Ic,

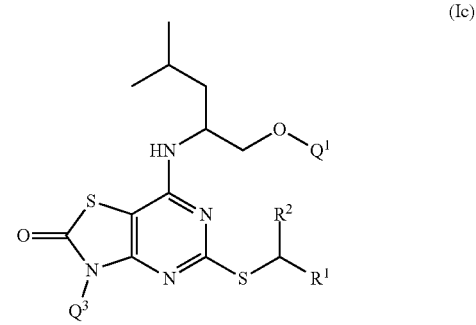

(Ic)

wherein $R^1$, $R^2$, $Q^1$ and $Q^3$ are as defined herein, or a pharmaceutically-acceptable salt thereof.

In particular embodiments that may be mentioned of the compound of formula Ic
- $Q^1$ represents —PO(OR$^6$)(OR$^7$);
- $Q^3$ represents H;
- $R^1$ represents phenyl optionally substituted by one or more (e.g. one) group selected from the group consisting of chloro, —SO$_2$Me, —CN and —CONH$_2$; or, particularly, pyridyl optionally substituted by one or more (e.g. one) chloro (e.g. 5-chloropyridin-2-yl);
- $R^2$ represents $C_{1-3}$ alkyl (e.g. methyl); and
- $R^6$ and $R^7$ each independently represent $C_{1-2}$ alkyl (e.g. Me) or particularly H.

In further particular embodiments that may be mentioned of the compound of formula Ic,
- $Q^1$ represents —PO(OR$^6$)(OR$^7$);
- $Q^3$ represents H;
- $R^1$ represents phenyl optionally substituted by one or more (e.g. one) chloro or, particularly, pyridyl optionally substituted by one or more (e.g. one) chloro (e.g. 5-chloropyridin-2-yl);
- $R^2$ represents $C_{1-3}$ alkyl (e.g. methyl); and
- $R^6$ and $R^7$ each independently represent $C_{1-2}$ alkyl (e.g. Me) or particularly H.

In other particular embodiments, of a compound of formula Ic that may be mentioned
- $Q^1$ represents H;
- $Q^3$ represents —CH$_2$OPO(OR$^6$)(OR$^7$);
- $R^1$ represents phenyl optionally substituted by one or more (e.g. one) chloro or, particularly, pyridyl optionally substituted by one or more (e.g. one) chloro (e.g. 5-chloropyridin-2-yl);
- $R^2$ represents $C_{1-3}$ alkyl (e.g. methyl); and
- $R^6$ and $R^7$ each independently represent $C_{1-2}$ alkyl (e.g. Me) or particularly H.

In further particular embodiments, the compound of formula I is a compound of formula IA

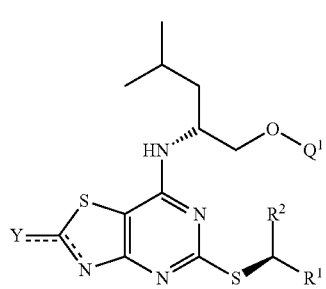

(IA)

wherein $R^1$, $R^2$, $Q^1$ and

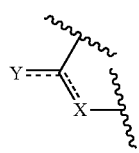

are as defined herein, or a pharmaceutically-acceptable salt thereof.

The skilled person will understand that the compound of formula IA is single enantiomer of the compound of formula I. In accordance with convention, the wedged and hashed bonds indicate a substantial absence of the other stereochemistry in at each stereocentre.

In further particular embodiments, the compound of formula IA is a compound of formula IAa, IAb or IAc,

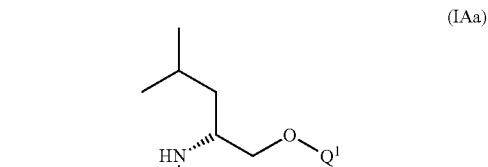

(IAa)

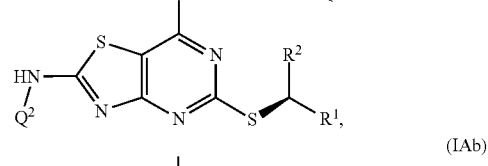

(IAb)

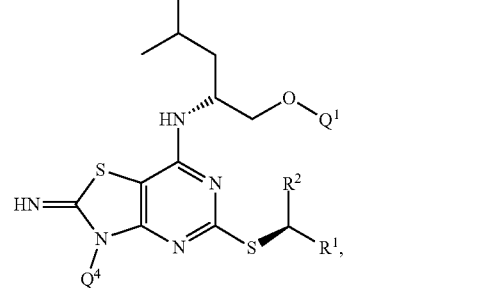

(IAc)

wherein (for each of the compounds IAa, IAb and IAc), $R^1$, $R^2$, $Q^1$, $Q^2$, $Q^3$ and $Q^4$ are as defined herein, particularly with respect to compounds of formula Ia, Ib and Ic, respectively, or a pharmaceutically-acceptable salt thereof.

In further particular embodiments, the compound of formula I is a compound of formula IB or IC.

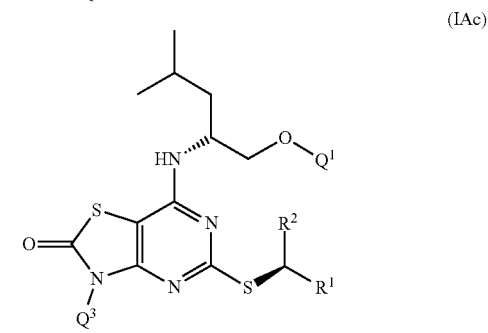

(IB)

wherein $R^1$, $R^2$, $Q^1$, $Q^2$, $Q^3$ and $Q^4$ are as defined herein, particularly with respect to compounds of formula Ia, Ib and Ic.

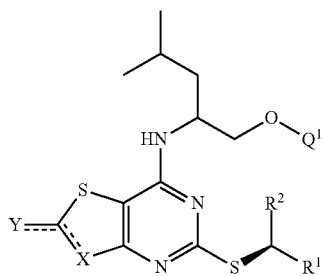

(IC)

wherein $R^1$, $R^2$, $Q^1$, $Q^2$, $Q^3$ and $Q^4$ are as defined herein, particularly with respect to compounds of formula Ia, Ib and Ic.

Particular compounds of the invention that may be mentioned include those compounds as described in the examples provided herein, and pharmaceutically acceptable salts thereof.

For the avoidance of doubt, where such compounds of the invention include compounds in a particular salt form, compounds of the invention include those compounds in non-salt form and in the form of any pharmaceutically acceptable salt thereof (which may include the salt form present in such examples).

More particular compounds of the invention that may be mentioned include:
(2R)-2-[(2-Amino-5-{[(1S)-1-phenylethyl]sulfanyl}[1,3] thiazolo[4,5-d]pyrimidin-7-yl)amino]-4-methylpentyl dihydrogen phosphate,
[7-{[(1R)-1-(Hydroxymethyl)-3-methylbutyl]amino}-2-imino-5-{[(1S)-1-phenylethyl]sulfanyl}[1,3]thiazolo[4,5-d]pyrimidin-3(2H)-yl]methyl dihydrogen phosphate, and
(2R)-2-[(5-{[(1S)-1-(5-chloropyridin-2-yl)ethyl]sulfanyl}-2-oxo-2,3-dihydro[1,3]thiazolo[4,5-d]pyrimidin-7-yl) amino]-4-methylpentyl dihydrogen phosphate, and pharmaceutically acceptable salts thereof.

Pharmaceutically-Acceptable Salts

As mentioned above, the compounds of the invention may be in the form of pharmaceutically-acceptable salts.

In particular embodiments, the pharmaceutically-acceptable salt is a base-addition salt.

In more particular embodiments, particularly those in which $R^6$ and $R^7$ each represent H (i.e. compounds containing phosphate —OPO(OH)$_2$ groups) the pharmaceutically-acceptable salt is a double base addition salt.

As used herein, the phrase 'double base addition salt' may be understood to indicate a salt formed from the reaction of an acidic compound (such as a compound of the invention wherein $R^6$ and $R^7$ each represent H) with two moles of a suitable base.

In particular embodiments, the pharmaceutically-acceptable salt is an ammonium salt, or an alkali metal (Li, K, or, particularly Na) salt (including monosalts and disalts). In more particular embodiments the salt is a diammonium or a disodium salt.

Medical Uses

As indicated herein, the compounds of the invention, and therefore compositions and kits comprising the same, are useful as pharmaceuticals. In particular the compounds of the invention and their derivatives are modulators of the fractalkine receptor (CX3CR1) activity, and may therefore be used in the treatment and/or prevention of diseases or disorders associated with elevated levels of the fractalkine receptor (CX3CR1) and/or its associated ligand fractalkine (CX3CL1).

Thus, according to a second aspect of the invention there is provided a compound of the invention, as hereinbefore defined (i.e. a compound as defined in the first aspect of the invention, including all embodiments and particular features thereof), for use as a pharmaceutical (or for use in medicine).

For the avoidance of doubt, references to compounds as defined in the first aspect of the invention will include references to compounds of formula I (including all embodiments thereof, such as compounds of formulas Ia, Ib, Ic, IA, IAa, IAb, IAc, IB, IC) and pharmaceutically acceptable salts thereof.

For the avoidance of doubt, compounds of the invention are therefore useful because they possess pharmacological activity, and/or are metabolised in the body following oral or parenteral administration to form compounds that possess pharmacological activity.

As described herein, compounds of the invention may be particularly useful in treating and/or preventing diseases or disorders associated with elevated levels of CX3CR1 and/or CX3CL1.

Thus, in a third aspect of the invention, there is provided a compound of the invention, as hereinbefore defined, for use in the treatment and/or prevention of a disease or disorder associated with elevated levels of CX3CR1 and/or CX3CL1.

In an alternative third aspect of the invention, there is provided a method of treating and/or preventing disease or disorder associated with elevated levels of CX3CR1 and/or CX3CL1, comprising administering to a patient in need thereof a therapeutically effective amount of a compound of the invention, as hereinbefore defined.

In a further alternative third aspect of the invention, there is provided the use of a compound of the invention, as hereinbefore defined, for the manufacture of a medicament for the treatment and/or prevention of a disease or disorder associated with elevated levels of CX3CR1 and/or CX3CL1.

The skilled person will understand that references to the treatment of a particular condition (or, similarly, to treating that condition) will take their normal meanings in the field of medicine. In particular, the terms may refer to achieving a reduction in the severity and/or frequency of occurrence of one or more clinical symptom associated with the condition, as adjudged by a physician attending a patient having or being susceptible to such symptoms. For example, in the case of cancer, the term may refer to achieving a reduction of the amount of cancerous cells present (e.g. in the case of a cancer forming a solid tumour, as indicated by a reduction in tumour volume).

As used herein, the term prevention (and, similarly, preventing) will include references to the prophylaxis of the disease or disorder (and vice-versa). As such, references to prevention may also be references to prophylaxis, and vice versa. In particular, such terms term may refer to achieving a reduction (for example, at least a 10% reduction, such as at least a 20%, 30% or 40% reduction, e.g. at least a 50% reduction) in the likelihood of the patient (or healthy subject) developing the condition (which may be understood as meaning that the condition of the patient changes such that patient is diagnosed by a physician as having, e.g. requiring treatment for, the relevant disease or disorder).

As used herein, references to a patient (or to patients) will refer to a living subject being treated, including mammalian (e.g. human) patients. In particular, references to a patient will refer to human patients.

For the avoidance of doubt, the skilled person will understand that such treatment or prevention will be performed in a patient (or subject) in need thereof. The need of a patient (or subject) for such treatment or prevention may be assessed by those skilled the art using routine techniques.

As used herein, the terms disease and disorder (and, similarly, the terms condition, illness, medical problem, and the like) may be used interchangeably.

As used herein, the term effective amount will refer to an amount of a compound that confers a therapeutic effect on the treated patient. The effect may be observed in a manner that is objective (i.e. measurable by some test or marker) or subjective (i.e. the subject gives an indication of and/or feels an effect). In particular, the effect may be observed (e.g. measured) in a manner that is objective, using appropriate tests as known to those skilled in the art.

Diseases and disorders that are known to be associated with elevated levels of CX3CR1 and/or CX3CL1 include acute and/or chronic inflammation, eye diseases (such as macular degeneration), lung diseases (such as pulmonary arterial hypertension, asthma and pulmonary fibrosis), skin diseases (such as atopic dermatitis and pruritus), joint and/or bone diseases (such as osteoarthritis, osteoporosis and aplastic anaemia), autoimmune diseases (such as ankylosing spondylitis, multiple sclerosis, systemic sclerosis and rheumatoid arthritis), cardiovascular and metabolic diseases (such as stroke and arteriosclerosis (including atherosclerosis), unstable angina, myocardial infarction, carotid artery diseases, chronic heart failure, inflammatory cardiomyopathy, peripheral artery disease and diabetes), brain and neurodegenerative diseases (such as Alzheimer's disease, Parkinson's disease and traumatic brain injury), pain (such as chronic pain, fibromyalgia, neuropathic pain, chemotherapy-induced pain and intervertebral disc herniation), cancer (such as ovarian cancer, lung cancer, prostate cancer, liver cancer, pancreatic cancer, B-cell lymphomas and breast cancer), liver disease (such as cirrhosis), kidney diseases (such as IgA nephropathy, renal inflammation, lupus, ischemia reperfusion injury, ischemic acute renal failure and contrast-induced kidney injury), gastrointestinal diseases (such as colitis, Crohn's disease, inflammatory bowel disease and pancreatitis), human immunodeficiency virus (HIV) (such as HIV-1 and HIV-associated dementia) and mood disorders (such as depression, anxiety, schizophrenia and autism spectrum disorders).

Particular diseases and disorders that are known to be associated with elevated levels of CX3CR1 and/or CX3CL1 that may be mentioned include eye diseases (such as macular degeneration), lung diseases (such as pulmonary arterial hypertension, asthma and pulmonary fibrosis), skin diseases (such as atopic dermatitis and pruritus), joint and/or bone diseases (such as osteoarthritis, osteoporosis and aplastic anaemia), autoimmune diseases (such as ankylosing spondylitis, multiple sclerosis, systemic sclerosis and rheumatoid arthritis), cardiovascular and metabolic diseases (such as arteriosclerosis (including atherosclerosis), unstable angina, myocardial infarction, carotid artery diseases, chronic heart failure and diabetes), brain and neurodegenerative diseases (such as Alzheimer's disease and traumatic brain injury), pain (such as chronic pain, fibromyalgia, neuropathic pain, chemotherapy-induced pain and intervertebral disc herniation), cancer (such as ovarian cancer, lung cancer, prostate cancer, liver cancer, pancreatic cancer, B-cell lymphomas and breast cancer), liver disease (such as cirrhosis), kidney diseases (such as IgA nephropathy, renal inflammation, lupus and ischemia reperfusion injury), gastrointestinal diseases (such as colitis, inflammatory bowel disease and pancreatitis), and human immunodeficiency virus (HIV) (such as HIV-1 and HIV-associated dementia).

In particular embodiments (i.e. certain embodiments of the third aspect of the invention), the disease or disorder associated with elevated levels of CX3CR1 and/or CX3CL1 is selected from eye diseases, lung diseases, skin diseases, joint and/or bone diseases, autoimmune diseases, cardiovascular diseases, metabolic diseases, brain diseases, neurodegenerative diseases, pain, cancer, liver diseases, kidney diseases, gastrointestinal diseases and human immunodeficiency virus.

In particular embodiments (i.e. certain embodiments of the third aspect of the invention), the disease or disorder associated with elevated levels of CX3CR1 and/or CX3CL1 is selected from eye diseases, lung diseases, skin diseases, joint and/or bone diseases, autoimmune diseases, cardiovascular diseases, metabolic diseases, brain diseases, neurodegenerative diseases, pain, cancer, liver diseases, kidney diseases, gastrointestinal diseases, human immunodeficiency virus and mood disorders.

In more particular embodiments, the fractalkine-related disease or disorder associated with elevated levels of CX3CR1 and/or CX3CL1 is selected from macular degeneration, pulmonary arterial hypertension, asthma, pulmonary fibrosis, atopic dermatitis, pruritus, osteoarthritis, osteoporosis, aplastic anaemia, ankylosing spondylitis, multiple sclerosis, systemic sclerosis, rheumatoid arthritis, arteriosclerosis, unstable angina, myocardial infarction, carotid artery diseases, chronic heart failure, diabetes, Alzheimer's disease, traumatic brain injury, chronic pain, fibromyalgia, neuropathic pain, chemotherapy-induced pain, intervertebral disc herniation, cancer (for example ovarian cancer, lung cancer, liver cancer, pancreatic cancer, B-cell lymphomas and breast cancer) liver cirrhosis, IgA nephropathy, renal inflammation, lupus, ischemia reperfusion injury, colitis, inflammatory bowel disease, pancreatitis, human immunodeficiency virus-1 and human immunodeficiency virus-associated dementia, stroke, Parkinson's disease, depression, anxiety, schizophrenia and autism spectrum disorders.

In more particular embodiments, the fractalkine-related disease or disorder associated with elevated levels of CX3CR1 and/or CX3CL1 is selected from macular degeneration, pulmonary arterial hypertension, asthma, pulmonary fibrosis, atopic dermatitis, pruritus, osteoarthritis, osteoporosis, aplastic anaemia, ankylosing spondylitis, multiple sclerosis, systemic sclerosis, rheumatoid arthritis, arteriosclerosis, unstable angina, myocardial infarction, carotid artery diseases, chronic heart failure, diabetes, Alzheimer's disease, traumatic brain injury, chronic pain, fibromyalgia, neuropathic pain, chemotherapy-induced pain, intervertebral disc herniation, cancer (for example ovarian cancer, lung cancer, liver cancer, pancreatic cancer, B-cell lymphomas and breast cancer) liver cirrhosis, IgA nephropathy, renal inflammation, lupus, ischemia reperfusion injury, colitis, inflammatory bowel disease, pancreatitis, human immunodeficiency virus-1 and human immunodeficiency virus-associated dementia.

In more particular embodiments, the disease or disorder associated with elevated levels of CX3CR1 and/or CX3CL1 is selected from atopic dermatitis, multiple sclerosis, rheumatoid arthritis, atherosclerosis, myocardial infarction, chronic heart failure, inflammatory cardiomyopathy, fibromyalgia, neuropathic pain, chemotherapy-induced pain, B-cell lymphomas, breast cancer, IgA nephropathy, lupus, ischemic acute renal failure and pancreatitis.

In yet more particular embodiments, the disease or disorder associated with elevated levels of CX3CR1 and/or CX3CL1 is selected from myocardial infarction, arteriosclerosis, multiple sclerosis, rheumatoid arthritis, Crohn's disease, pancreatitis, neuropathic pain, chemotherapy-induced pain and cancer (for example ovarian cancer, lung cancer, liver cancer, pancreatic cancer, B-cell lymphomas and breast cancer).

In particular embodiments, the treatment of the disease or disorder associated with elevated levels of CX3CR1 and/or CX3CL1 is in a patient with significantly elevated CX3CL1 blood plasma levels. For example, such patients may have a blood plasma concentration of CX3CL1 of more than about 300 picograms per millilitre (pg/mL). In particular, such patients may have a blood plasma concentration of CX3CL1 from about 350 pg/mL to about 600 pg/mL.

Pharmaceutical Compositions

As described herein, compounds of the invention are useful as pharmaceuticals. Such compounds may be administered alone or may be administered by way of known pharmaceutical compositions/formulations.

In a fourth aspect of the invention, there is provided a pharmaceutical composition comprising a compound of the invention as defined herein, and optionally one or more pharmaceutically-acceptable excipient.

As used herein, the term pharmaceutically-acceptable excipients includes references to vehicles, adjuvants, carriers, diluents, pH adjusting and buffering agents, tonicity adjusting agents, stabilizers, wetting agents and the like. In particular, such excipients may include adjuvants, diluents or carriers.

In a particular embodiment of the fourth aspect of the invention, the pharmaceutical composition comprises at least one pharmaceutically-acceptable excipient.

For the avoidance of doubt, references herein to compounds of invention being for particular uses (and, similarly, to uses and methods of use relating to compounds of the invention) may also apply to pharmaceutical compositions comprising compounds of the invention, as described herein.

Thus, in a fifth aspect of the invention, there is provided a pharmaceutical composition as defined in the fourth aspect of the invention for use in the treatment of fractalkine-related diseases (as defined herein, with reference to the third aspect of the invention and all embodiments thereof).

The skilled person will understand that compounds of the invention act systemically and/or locally (i.e. at a particular site), and may therefore be administered accordingly using suitable techniques known to those skilled in the art.

The skilled person will understand that compounds and compositions as described herein will normally be administered orally, intravenously, intraocularly, subcutaneously, buccally, rectally, dermally, nasally, tracheally, bronchially, sublingually, intranasally, topically, by any other parenteral route or via inhalation, in a pharmaceutically acceptable dosage form. In particular, the compounds may be administered orally (i.e. through per oral administration) or intravenously.

Pharmaceutical compositions as described herein will include compositions in the form of tablets, capsules or elixirs for oral administration, suppositories for rectal administration, sterile solutions or suspensions for parenteral (e.g. intravenous) or intramuscular administration, and the like.

Thus, in particular embodiments, the pharmaceutical formulation is provided in a pharmaceutically acceptable dosage form, including tablets or capsules, liquid forms to be taken orally or by injection, suppositories, creams, gels, foams, inhalants (e.g. to be applied intranasally), or forms suitable for topical administration (e.g. eye drops). For the avoidance of doubt, in such embodiments, compounds of the invention may be present as a solid (e.g. a solid dispersion), liquid (e.g. in solution) or in other forms, such as in the form of micelles.

For example, in the preparation of pharmaceutical formulations for oral administration, the compound may be mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or compressed into tablets.

Soft gelatin capsules may be prepared with capsules containing one or more active compounds (e.g. compounds of the first and, therefore, second and third aspects of the invention, and optionally additional therapeutic agents), together with, for example, vegetable oil, fat, or other suitable vehicle for soft gelatin capsules. Similarly, hard gelatine capsules may contain such compound(s) in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the compound(s) mixed with a neutral fat base; (ii) in the form of a gelatin rectal capsule which contains the active substance in a mixture with a vegetable oil, paraffin oil, or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing the compound(s) and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of the compound(s) in a pharmaceutically acceptable solvent (e.g. water). These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

Depending on e.g. potency and physical characteristics of the compound of the invention (i.e. active ingredient), pharmaceutical formulations that may be mentioned include those in which the active ingredient is present in an amount that is at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The skilled person will understand that compounds of the invention may be administered (for example, as formulations as described hereinabove) at varying doses, with suitable doses being readily determined by one of skill in the art. Oral, pulmonary and topical dosages (and subcutaneous dosages, although these dosages may be relatively lower) may range from between about 0.01 mg/kg of body weight per day (mg/kg/day) to about 30 mg/kg/day, preferably about 0.1 to about 5.0 mg/kg/day, and more preferably about 0.5 to about 3.0 mg/kg/day. For example, when administered orally, treatment with such compounds may comprise administration of a formulations typically containing between about 0.01 mg to about 5000 mg, for example between about 0.1 mg to about 500 mg, or between 1 mg to about 400 mg (e.g. about 20 mg to about 200 mg), of the active ingredient(s). When administered intravenously, the most preferred doses will range from about 0.001 to about 10 mg/kg/hour during constant rate infusion. Advantageously, treatment may comprise administration of such compounds and compositions in a single daily dose, or the total daily dosage may be administered in divided doses of two, three or four times daily (e.g. twice daily with reference to the doses described herein, such as a dose of 25 mg, 50 mg, 100 mg or 200 mg twice daily).

When used herein in relation to a specific value (such as an amount), the term "about" (or similar terms, such as "approximately") will be understood as indicating that such values may vary by up to 10% (particularly, up to 5%, such as up to 1%) of the value defined. It is contemplated that, at each instance, such terms may be replaced with the notation "±10%", or the like (or by indicating a variance of a specific amount calculated based on the relevant value). It is also contemplated that, at each instance, such terms may be deleted.

For the avoidance of doubt, the skilled person (e.g. the physician) will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. Although the above-mentioned dosages are exemplary of the average case, there can, of course, be individual instances where higher or lower dosage ranges are merited, and such doses are within the scope of the invention.

The compounds of the invention display considerably-improved aqueous solubility compared to known fractalkine receptor antagonists, as well as considerably-improved stability to long-term storage in an aqueous environment.

Accordingly, in particular embodiments, pharmaceutical compositions comprising one or more (e.g. one) compounds of the invention further comprise water.

In more particular embodiments, the pharmaceutical composition comprising one or more (e.g. one) compounds of the invention is in the form of an aqueous solution.

The skilled person will understand that references to pharmaceutical compositions being in the form of an aqueous solution refer to compositions in which the active ingredient, and optionally, one or more pharmaceutically-acceptable excipients are dissolved in water.

The considerably-enhanced aqueous solubility and stability to storage under aqueous conditions allows the compounds of the invention to be formulated in water (e.g. as aqueous solutions) without the need to include solubilising excipients.

Thus, in particular embodiments, there is provided a pharmaceutical composition comprising one or more (e.g. one) compounds of the invention, water and less than 20% (w/w) of I solubilising excipients (such as less than 10%, for example less than 5% (e.g less than 1%). In more particular embodiments, such a composition is in the form of an aqueous solution.

As used herein, the phrase solubilising excipients may be understood to refer to (pharmaceutically-acceptable) excipients that are used to solubilise organic compounds in an aqueous environment (such as in an aqueous pharmaceutical formulation), to produce a stable solution or suspension of the active ingredient. Such solubilising excipients include water-miscible/soluble solvents, and water-soluble surfactants. Examples of such excipients include ethanol, polyethyelene glycol (PEG) (PEG 400, PEG 300), polysorbates, cyclodextrins, dimethylsulfoxide, polysorbate 80 (Tween 80), propylene glycol, ethylene glycol, glycerol, dimethyl acetamide, polyoxyethylated castor oils (e.g. Chremophor), polyoxyethylated glycerides, stearyl alcohol, oleyl alcohol In alternative embodiments, the pharmaceutical compositions comprising the compounds of the invention are in the form of a (dry) powder (i.e. a powder comprising a compound of the invention, and optionally, one or more pharmaceutically-acceptable excipients. As described above, it is envisaged that such a powder may be reconstituted with a suitable liquid (particularly water, optionally in the form of an aqueous solution of pharmaceutically-acceptable excipients) to form a liquid dosage form (e.g. an aqueous solution) prior to administration.

In particular embodiments, the compositions comprising the compounds of the invention (and or pharmaceutical formulations comprising the same), are in a dosage form suitable for oral or intravenous administration (e.g. oral administration).

Combinations and Kits-of-Parts

The skilled person will understand that treatment with compounds of the invention may further comprise (i.e. be combined with) further treatment(s) or preventative methods for the same condition. In particular, treatment with compounds of the invention may be combined with means for the treatment of a fractalkine-related disease as described herein, e.g. an inflammatory disease, an autoimmune disease, cancer and/or cardiovascular disease), such as treatment with one or more other therapeutic agent that is useful in the in the treatment or prevention of a fractalkine-related disease and/or one or more physical method used in the treatment (such as treatment through surgery), as known to those skilled in the art.

As described herein, compounds of the invention may also be combined with one or more other (i.e. different) therapeutic agents (i.e. agents that are not compounds of the invention) that are useful in the treatment and/or prevention of a fractalkine-related disease. Such combination products that provide for the administration of a compound of the invention in conjunction with one or more other therapeutic agent may be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the one or more other therapeutic agent).

Thus, according to a sixth aspect of the invention, there is provided a combination product comprising:

(I) a compound of the invention, as hereinbefore defined (i.e. in the first aspect of the invention, including all embodiments and particular features thereof); and (II) one or more other therapeutic agent that is useful in the treatment and/or prevention of a disease or disorder associated with elevated levels of CX3CR1 and/or CX3CL1 (such as eye diseases, lung diseases, skin diseases, joint and/or bone diseases, autoimmune diseases, cardiovascular diseases, metabolic diseases, brain diseases, neurodegenerative diseases, pain, cancer, liver diseases, kidney diseases, gastrointestinal diseases and human immunodeficiency virus as described herein), wherein each of components (I) and (II) is formulated in admixture, optionally with one or more a pharmaceutically-acceptable excipient.

In a seventh aspect of the invention, there is provided a kit-of-parts comprising:

(a) a pharmaceutical formulation as hereinbefore defined (i.e. in the fourth aspect of the invention); and (b) one or more other therapeutic agent that is useful in the treatment or prevention of a disease or disorder associated with elevated levels of CX3CR1 and/or CX3CL1 (such as eye diseases, lung diseases, skin diseases, joint and/or bone diseases, autoimmune diseases, cardiovascular diseases, metabolic diseases, brain diseases, neurodegenerative diseases, pain, cancer, liver diseases, kidney diseases, gastrointestinal diseases and human immunodeficiency virus as described herein), optionally in admixture with one or more pharmaceutically-acceptable excipient, which components (a) and (b) are each provided in a form that is suitable for administration in conjunction (i.e. concomitantly or sequentially) with the other.

With respect to the kits-of-parts as described herein, by "administration in conjunction with" (and similarly "administered in conjunction with") we include that respective formulations are administered, sequentially, separately or simultaneously, as part of a medical intervention directed towards treatment of the relevant condition.

Thus, in relation to the present invention, the term "administration in conjunction with" (and similarly "administered in conjunction with") includes that the two active ingredients (i.e. a compound of the invention and a further agent for the treatment and/or prevention of fractalkine-related diseases, or compositions comprising the same) are administered (optionally repeatedly) either together, or sufficiently closely in time, to enable a beneficial effect for the patient, that is greater, over the course of the treatment and/or prevention of the relevant condition, than if either agent is administered (optionally repeatedly) alone, in the absence of the other component, over the same course of treatment and/or prevention. Determination of whether a combination provides a greater beneficial effect in respect of, and over the course of, treatment and/or prevention of a particular condition will depend upon the condition to be treated and/or prevented, but may be achieved routinely by the skilled person.

Further, in the context of the present invention, the term "in conjunction with" includes that one or other of the two formulations may be administered (optionally repeatedly) prior to, after, and/or at the same time as, administration of the other component. When used in this context, the terms "administered simultaneously" and "administered at the same time as" includes instances where the individual doses of the compound of the invention and the additional compound for the treatment of a disease or disorder associated with elevated levels of CX3CR1 and/or CX3CL1, or pharmaceutically acceptable salts thereof, are administered within 48 hours (e.g. within 24 hours, 12 hours, 6 hours, 3 hours, 2 hours, 1 hour, 45 minutes, 30 minutes, 20 minutes or 10 minutes) of each other.

As used herein, references to other therapeutic agents that are "useful" in a certain manner (e.g. in the treatment of a certain disease or disorder) will refer to agents that are known to be suitable for use in that manner (e.g. agents commonly used for that purpose). Such references may therefore be replaced with references to agents "suitable for" the relevant purpose.

Other therapeutic agents useful in the treatment and/or prevention of fractalkine-related diseases (such as those described herein) will be well-known to those skilled in the art. For example, such other therapeutic agents may include:

anti-inflammatory drugs (such as non-steroidal anti-inflammatory drugs (NSAIDs), corticosteroids and targeted anti-inflammatory antibodies);

anti-cancer agents (such as alkylating agents, antimetabolites, anti-tumour antibiotics, topoisomerase inhibitors, mitotic inhibitors, immunomodulators, targeted therapies (e.g. kinase inhibitors) and DNA-repair interfering drugs);

compounds for treating cardiovascular diseases (such as ACE inhibitors (angiotensin-converting enzyme inhibitors), antiarrhythmic medicines, anticoagulant medicines, antiplatelet medicines, beta-blockers, calcium channel blockers cholesterol-lowering medicines (such as statins), and acetylsalicylic acid.

Preparation of Compounds/Compositions

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable excipient.

In further aspects of the invention, there is provided a process for the preparation of a combination product or kit-of-parts as hereinbefore defined, which process comprises bringing into association a compound of the invention, as hereinbefore defined, with the other therapeutic agent that is useful in the treatment of the relevant disease or disorder, and at least one pharmaceutically-acceptable excipient.

As used herein, references to bringing into association will mean that the two components are rendered suitable for administration in conjunction with each other.

Thus, in relation to the process for the preparation of a kit-of-parts as hereinbefore defined, by bringing the two components "into association with" each other, we include that the two components of the kit-of-parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Compounds of the invention as described herein may be prepared in accordance with techniques that are well known to those skilled in the art, such as those described in the examples provided hereinafter.

Precursor compounds to the compounds of the invention (such as (2R)-2-[(2-amino-5-{[(1S)-1-phenylethyl]sulfanyl}-[1,3] thiazolo[4,5-d]pyrimidin-7-yl)amino]-4-methylpentan-1-ol hydrochloride and 5-{[(1S)-1-(5-chloropyridin-2-yl)ethyl]sulfanyl}-7-{[(1R)-1-(hydroxymethyl)-3-methylbutyl]amino}[1,3]thiazolo[4,5-d]pyrimidin-2(3H)-one (Compounds of formula II) may be prepared following procedures known in the art, such as those described in Karlström S., et al., (*J. Med. Chem.*, 2013, 56, 3177-3190 (including supporting information)), WO 2006/107258 and WO 2008/039138.

According to an eighth aspect of the invention there is provided a process for the preparation of a compound of the invention as hereinbefore defined, which process comprises:

(a) for compounds wherein $Q^1$ represents —PO(OR$^6$)(OR$^7$), wherein $R^6$ and $R^7$ are as defined herein (i) reacting a compound of formula II

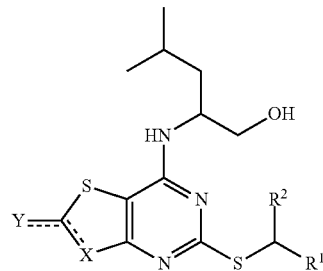

(II)

wherein $R^1$ and $R^2$ are as defined herein; and

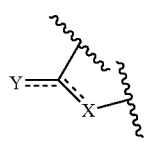

represents

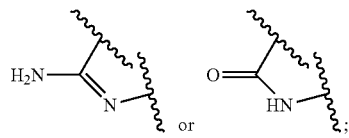 [SMILES: */N=C(\*)N ; *NC(*)=O]

with phosphorus oxychloride in the presence of a suitable solvent (for example tetrahydrofuran, diethyl ether or methyl tert-butyl ether) and a suitable base (for example pyridine or triethylamine); then (ii) adding water or $R^6$OH/$R^7$OH to the reaction mixture;

(b) for compounds wherein $Q^2$ represents —PO(OR$^6$)(OR$^7$);

reacting a compound of formula III

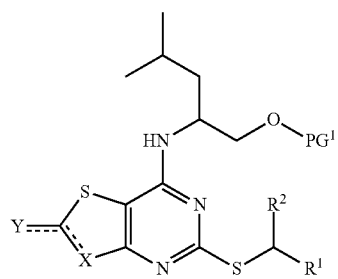

(III)

wherein:

$R^1$ and $R^2$ are as defined herein;

PG$^1$ represents a suitable oxygen protecting group (for example a silyl protecting group, e.g. trimethyl silyl, tert-butyldimethylsilyl or triisopropyl silyl);

in the presence of phosphorus pentachloride, suitable solvent (e.g. dichloromethane) and, optionally, a suitable base (e.g. pyridine)

(c) for compounds wherein $Q^3$ or $Q^4$, represents —CH$_2$OPO(OR$^6$)(OR$^7$) and at least one of $R^6$ and $R^7$ represents $C_{1-4}$ alkyl or $C_{2-4}$ alkenyl reacting a compound of formula II

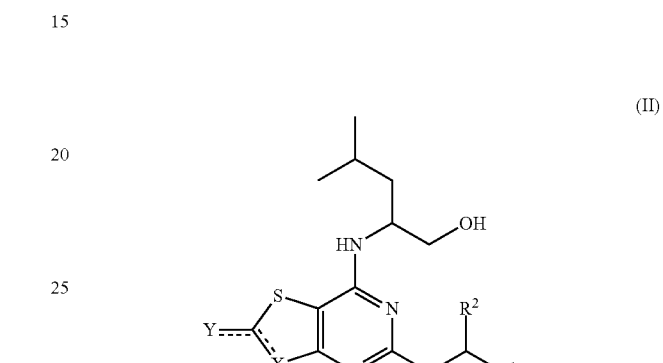

(II)

wherein $R^1$ and $R^2$ are as defined herein; and

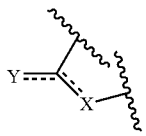

represents

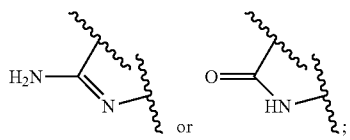

with a compound of formula IV

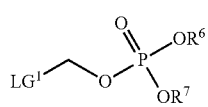

(IV)

wherein $R^6$ and $R^7$ are as defined herein with the proviso that at least one of $R^6$ and $R^7$ represents $C_{1-4}$ alkyl or $C_{2-4}$ alkenyl and LG$^1$ represents a suitable leaving group (such as halo (e.g. Cl, Br);

in the presence of a suitable base (e.g. $K_2CO_3$) and a suitable solvent (e.g. acetonitrile);

(d) for compounds wherein $Q^3$ or $Q^4$, represents $-CH_2OPO(OH)_2$ (i) reacting a compound of formula II

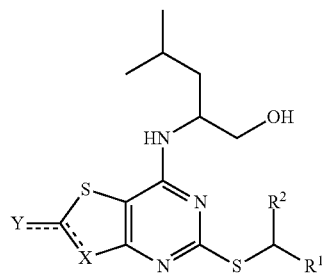

wherein $R^1$ and $R^2$ are as defined herein; and

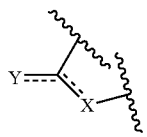

represents

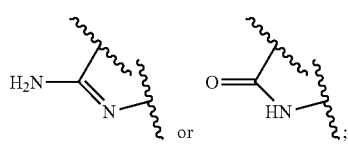

with a compound of formula V

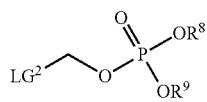

wherein $R^8$ and $R^9$ represent $C_{1-6}$ alkyl, $LG^2$ represents a suitable leaving group (such as halo (e.g. Cl, Br);

in the presence of a suitable base (e.g. $K_2CO_3$) and a suitable solvent (e.g. acetonitrile); and;

(ii) reacting the product formed in the presence of a suitable acid (e.g. HCl) and a suitable solvent (e.g. dioxane).

Compounds of formulae I to V are either commercially available, are known in the literature, or may be obtained either by analogy with the processes described herein, or by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991. Further references that may be employed include "*Heterocyclic Chemistry*" by J. A. Joule, K. Mills and G. F. Smith, 3$^{rd}$ edition, published by Chapman & Hall, "*Comprehensive Heterocyclic Chemistry II*" by A. R. Katritzky, C. W. Rees and E. F. V. Scriven, Pergamon Press, 1996 and "*Science of Synthesis*", Volumes 9-17 (Hetarenes and Related Ring Systems), Georg Thieme Verlag, 2006.

The skilled person will understand that the substituents as defined herein, and substituents thereon, may be modified one or more times, after or during the processes described above for the preparation of compounds of the invention by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "*Comprehensive Organic Functional Group Transformations*" by A. R. Katritzky, O. Meth-Cohn and C. W. Rees, Pergamon Press, 1995 and/or "*Comprehensive Organic Transformations*" by R. C. Larock, Wiley-VCH, 1999.

Compounds of the invention may be isolated from their reaction mixtures and, if necessary, purified using conventional techniques as known to those skilled in the art. Thus, processes for preparation of compounds of the invention as described herein may include, as a final step, isolation and optionally purification of the compound of the invention.

It will be appreciated by those skilled in the art that, in the processes described herein, the functional groups of intermediate compounds may need to be protected by protecting groups. The protection and deprotection of functional groups may take place before or after a reaction in the above-mentioned schemes.

Compounds of formulae III, IV and V feature protecting groups. Protecting groups may be applied and removed in accordance with techniques that are well-known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis*", 3rd edition, T. W. Greene & P. G. M. Wutz, Wiley-Interscience (1999), the contents of which are incorporated herein by reference.

In particular, silyl ether protecting groups for oxygen atoms may be applied by reacting the relevant alcohol with a suitable trialkylsilyl halide (for example trimethylsilyl chloride or tert-butyldimethylsilylchloride) in the presence of a suitable base (e.g. N,N-diisopropylethylamine, triethylamine or N,N-dimethylaminopyridine). Silyl ether protecting groups may be removed in the presence of a suitable source of fluoride. (e.g. tetrabutyalammonium fluoride). Carbamate protecting groups for nitrogen atoms may be applied by reacting the relevant amine group with a suitable chloroformate or carbonate anhydride (e.g. di-tert-butyl dicarbonate), optionally in the presence of a suitable base and may be removed under appropriate acidic or basic conditions as known to the person skilled in the art. Benzyl protecting groups may be applied by reacting the relevant nitrogen atom with a suitable benzyl halide in the presence of a suitable base, and may be removed under suitable conditions known to the person skilled in the art (for example a 2,4-dimethoxy benzyl group may be removed in the presence of ceric ammonium nitrate and a suitable solvent).

It is believed that the compounds of the invention offer considerable advantages over known fractalkine receptor antagonists in terms of aqueous solubility and stability to storage under aqueous conditions.

Compounds of the invention may have the advantage that they may be more efficacious than, be less toxic than, be longer acting than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, compounds of the invention may have the advantage that they are more efficacious and/or exhibit advantageous properties in vivo.

In particular, it is believed that the compounds of the invention may enable treatment with higher dosages and/or longer treatment regimens than known fractalkine receptor antagonists and therefore offer considerable advantages in terms of the treatment options available to a patient.

EXAMPLES

General Procedures

The following abbreviations are used herein:

DCM Dichloromethane

DMAP 4-Dimethylaminopyridine

DMF N,N-dimethylformamide

DMSO Dimethyl sulfoxide

ESI Electrospray ionization

EtOAc Ethyl acetate

EtOH Ethanol

HPLC High Performance Liquid Chromatography

MeOH Methanol

MS Mass Spectrometry

NMR Nuclear Magnetic Resonance $^1$H NMR and $^{13}$C NMR spectra were recorded on a Varian Inova 600 equipped with a triple resonance probe. All spectra were recorded using the residual solvent proton resonance as internal standard. Analytical HPLC was carried out on an Agilent Series 1100 system using either a Kinetex C18 (2.6 μm, 3.0×50 mm) column with 0.1% formic acid in MilliQ $H_2O$/$CH_3CN$ as mobile phase (Acidic system) or a Kinetex EVO (2.6 μm 3.0×50 mm) column with 10 mM pH10 $NH_4HCO_3$/$CH_3CN$ as mobile phase (Basic system). Electrospray mass spectrometry (ES-MS) was performed using an Agilent 1100 Series Liquid Chromatograph/Mass Selective Detector (MSD) to obtain the pseudo molecular [M+H]$^+$ ion of the target molecules. Preparative HPLC was performed on a Gilson 306 HPLC system using either a Kinetex C18 (5 μm, 21×100 mm) column with 0.1% TFA in MilliQ $H_2O$/$CH_3CN$ as mobile phase (Acidic system) or a Gemini NX (5 μm, 21×100 mm) column with 50 mM pH10 $NH_4HCO_3$/$CH_3CN$ as mobile phase (Basic system). Fractions were collected based on the UV-signal at the maximum wavelength for the compound of interest. Preparative flash chromatography was performed on Merck silica gel 60 (230-400 mesh) or YMC gel 120 Å S-150 μm. Microwave reactions were performed with a Biotage Initiator instrument using 0.5-2 mL or 2-5 mL Biotage Process Vials fitted with aluminum caps and septa. The compounds were named using the software ACD Labs 10.0.

Example 1

Preparation of (2R)-2-[(2-Amino-5-{[(1S)-1-phenylethyl]sulfanyl}[1,3]thiazolo[4,5-d]pyrimidin-7-yl)amino]-4-methylpentyl dihydrogen phosphate

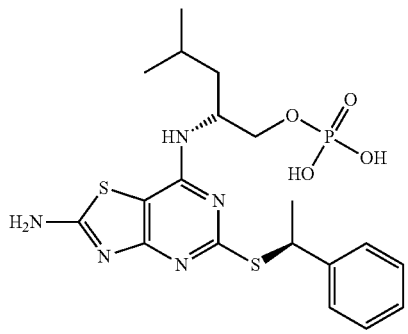

Phosphorus oxychloride (337 mg, 2.2 mmol) was dissolved in THF (0.75 mL) and water (25 mg, 1.4 mmol) was added. The mixture was cooled in an ice-bath and pyridine (111 mg, 113 μL, 1.4 mmol) was added followed by (2R)-2-[(2-amino-5-{[(1S)-1-phenylethyl]sulfanyl}-[1,3]thiazolo[4,5-d]pyrimidin-7-yl)amino]-4-methylpentan-1-ol hydrochloride (110 mg, 0.25 mmol) (Karlström S., et al., *J. Med. Chem.*, 2013, 56, 3177-3190; WO 2006/107258). The reaction mixture was stirred at ice-bath temperature for 1 h. To a mixture of phosphorus oxychloride (337 mg, 2.2 mmol) and water (25 mg, 1.4 mmol) in THF was added, at ice-bath temperature pyridine (111 mg, 113 μL, 1.4 mmol). Half of this mixture was added to the reaction mixture described above. The reaction mixture was stirred at ice-bath temperature for another 1 h. Water (3 mL) was added and the reaction mixture was stirred for 15 min at ice-bath temperature and 20 min at room temperature. DCM (3 mL) was added and the phases were separated. The aqueous phase was extracted with another portion of DCM (3 mL) and the organic phases were combined. At this point the product started to precipitate as a pale-yellow gum in the organic phase. MeOH was added and the now homogeneous solution was transferred to a round-bottomed flask and was evaporated to yield 120 mg of crude product, which according to HPLC was ca. 93% pure. The crude material was dissolved in a MeOH/water mixture and the pH was adjusted to about 6-7 with 1M NaOH. The material was purified by preparative HPLC (basic method). The pure fractions were pooled, evaporated, and dried in vacuum. The product was assumed to be the diammonium salt after purification. $^1$H NMR (600 MHz, CD$_3$OD) δ$_H$ ppm 7.43-7.47 (m, 2H) 7.30-7.35 (m, 2H) 7.20-7.24 (m, 1H) 5.08 (q, J=7.03 Hz, 1H) 4.59-4.68 (m, 1H) 3.92 (ddd, J=10.12, 5.67, 4.30 Hz, 1H) 3.88 (dt, J=10.12, 4.94 Hz, 1H) 1.74 (d, J=7.03 Hz, 3H) 1.71-1.79 (m, 1H) 1.68 (ddd, J=13.87, 9.54, 5.67 Hz, 1H) 1.57 (ddd, J=13.87, 8.54, 5.33 Hz, 1H) 0.98 (d, J=6.71 Hz, 3H) 0.96 (d, J=6.56 Hz, 3H). MS (ESI$^+$) m/z 484 [M+H]$^+$.

Example 1b (2R)-2-[(2-Amino-5-{[1-(2-fluorophenyl)ethyl]sulfanyl}[1,3]thiazolo[4,5-d]pyrimidin-7-yl)amino]-4-methylpentyl dihydrogen phosphate

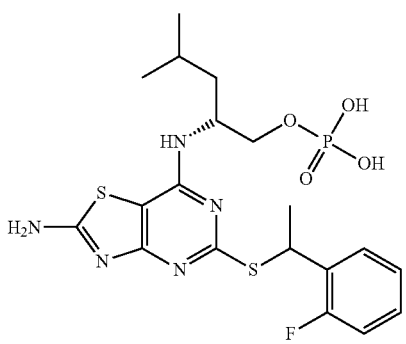

The title compound was synthesized from (2R)-2-[(2-amino-5-{[1-(2-fluorophenyl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in 55% yield using the method described for Example 1. The product is a mixture of two diastereomers. $^1$H NMR (600 MHz, DMSO-d$_6$) δ$_H$ ppm 7.98 (br. s., 4H) 8.09 (br. s., 2H) 7.50-7.57 (m, 2H) 7.26-7.32 (m, 2H) 7.15-7.20 (m, 4H) 7.30 (br. s., 4H) 5.25 (q, J=7.0 Hz, 1H) 5.24 (q, J=7.2 Hz, 1H) 4.22-4.30 (m, 1H) 4.14-4.25 (m, 1H) 3.75-3.82 (m, 1H) 3.65-3.76 (m, 3H) 1.69 (d, J=7.0 Hz, 3H) 1.66 (d, J=7.2 Hz, 3H) 1.56-1.65 (m, 2H) 1.46-1.57 (m, 2H) 1.41 (ddd, J=13.4, 6.9, 6.8 Hz, 2H) 0.88 (d, J=6.6 Hz, 3H) 0.88 (d, J=6.6 Hz, 3H) 0.85 (d, J=6.7 Hz, 3H) 0.84 (d, J=6.7 Hz, 3H). MS (ESI$^+$) m/z 502 [M+H]$^+$.

Example 1c (2R)-2-[(2-Amino-5-{[1-(2-chlorophenyl)ethyl]sulfanyl}[1,3]thiazolo[4,5-d]pyrimidin-7-yl)amino]-4-methylpentyl dihydrogen phosphate

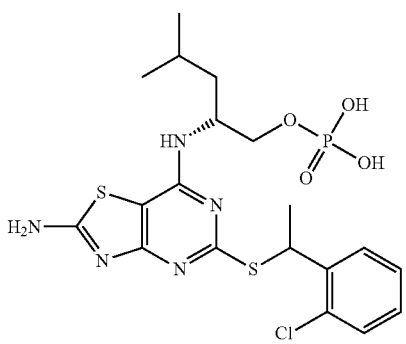

The title compound was synthesized from (2R)-2-[(2-amino-5-{[1-(2-chlorophenyl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in 55% yield using the method described for Example 1. The product is a mixture of two diastereomers. $^1$H NMR (600 MHz, DMSO-d$_6$) δ$_H$ ppm 8.31 (br. s., 2H) 7.95 (br. s., 4H) 7.61 (dd, J=7.8, 1.8 Hz, 1H) 7.60 (dd, J=7.8, 1.8 Hz, 1H) 7.45 (dd, J=8.0, 1.4 Hz, 1H) 7.45 (dd, J=8.0, 1.4 Hz, 1H) 7.35 (ddd, J=7.8, 7.3, 1.4 Hz, 1H) 7.34 (ddd, J=7.8, 7.3, 1.4 Hz, 1H) 7.28 (ddd, J=8.0, 7.3, 1.8 Hz, 1H) 7.28 (ddd, J=8.0, 7.3, 1.8 Hz, 1H) 6.77-7.56 (m, 4H) 5.42 (q, J=6.9 Hz, 1H) 5.36 (q, J=6.9 Hz, 1H) 4.16-4.29 (m, 2H) 3.76-3.84 (m, 1H) 3.64-3.76 (m, 3H) 1.71 (d, J=6.9 Hz, 3H) 1.67 (d, J=6.9 Hz, 3H) 1.49-1.65 (m, 4H) 1.37-1.45 (m, 2H) 0.89 (d, J=6.4 Hz, 3H) 0.88 (d, J=6.4 Hz, 3H) 0.87 (d, J=6.6 Hz, 3H) 0.83 (d, J=6.1 Hz, 3H). MS (ESI$^+$) m/z 518 [M+H]$^+$.

Example 1d (2R)-2-[(2-Amino-5-{[1-(5-chloropyridin-2-yl)ethyl]sulfanyl}[1,3]thiazolo[4,5-d]pyrimidin-7-yl)amino]-4-methylpentyl dihydrogen phosphate

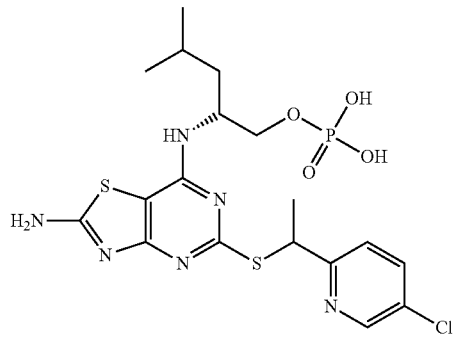

The title compound was synthesized from (2R)-2-[(2-amino-5-{[1-(5-chloropyridin-2-yl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in 16% yield using the method described for Example 1. The product is a mixture of two diastereomers. $^1$H NMR (600 MHz, DMSO-d$_6$) δ$_H$ ppm 8.57 (dd, J=2.5, 0.7 Hz, 1H) 8.55 (dd, J=2.5, 0.7 Hz, 1H) 8.02 (br. s., 4H) 7.88 (dd, J=8.5, 2.5 Hz, 1H) 7.84 (dd, J=8.4, 2.5 Hz, 1H) 7.58 (dd, J=8.5, 0.7 Hz, 1H) 7.56 (dd, J=8.5, 0.7 Hz, 1H) 6.93-7.51 (m, 4H) 5.14 (q, J=7.2 Hz, 1H) 5.07 (q, J=7.2 Hz, 1H) 4.40-4.51 (m, 1H) 4.15-4.26 (m, 1H) 3.74-3.82 (m, 3H) 3.71 (dt, J=10.3, 6.0 Hz, 1H) 1.66 (d, J=7.2 Hz, 3H) 1.64 (d, J=7.2 Hz, 3H) 1.54-1.65 (m, 2H) 1.44-1.54 (m, 2H) 1.40 (ddd, J=13.7, 8.9, 4.8 Hz, 1H) 1.35 (ddd, J=13.7, 8.7, 4.7 Hz, 1H) 0.87 (d, J=6.7 Hz, 3H) 0.85 (d, J=6.4 Hz, 3H) 0.84 (d, J=6.5 Hz, 3H) 0.76 (d, J=6.6 Hz, 3H). MS (ESI$^+$) m/z 519 [M+H]$^+$.

Example 1e (2R)-2-[(2-Amino-5-{[1-(3-fluoropyridin-2-yl)ethyl]sulfanyl}[1,3]thiazolo[4,5-d]pyrimidin-7-yl)amino]-4-methylpentyl dihydrogen phosphate

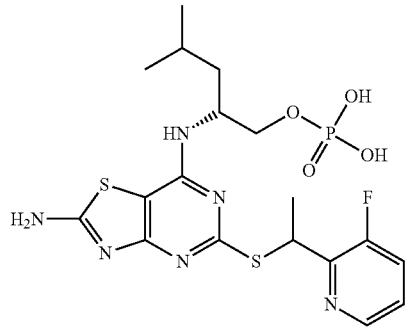

The title compound was synthesized from (2R)-2-[(2-amino-5-{[1-(3-fluoropyridin-2-yl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in 7% yield using the method described for Example 1. The product is a mixture of two diastereomers. $^1$H NMR (600 MHz, DMSO-d$_6$) δ$_H$ ppm 8.75 (br. s., 1H) 8.39-8.42 (m, 2H) 7.95 (br. s., 4H) 7.68-7.74 (m, 2H) 7.36-7.43 (m, 2H) 7.15 (br. s., 5H) 5.49 (q, J=6.9 Hz, 1H) 5.45 (q, J=6.9 Hz, 1H) 4.13-4.33 (m, 2H) 3.74-3.85 (m, 2H) 3.67-3.75 (m, 2H) 1.71 (d, J=6.9 Hz, 3H) 1.68 (d, J=6.9 Hz, 3H) 1.58-1.67 (m, 2H) 1.48-1.59 (m, 2H) 1.40-1.48 (m, 2H) 0.90 (d, J=6.5 Hz, 3H) 0.90 (d, J=6.5 Hz, 3H) 0.87 (d, J=6.7 Hz, 3H) 0.86 (d, J=6.7 Hz, 3H). MS (ESI$^+$) m/z 503 [M+H]$^+$.

Example 1f (2R)-2-[(2-Amino-5-{[1-(3-cyanophenyl)ethyl]sulfanyl}[1,3]thiazolo[4,5-d]pyrimidin-7-yl)amino]-4-methylpentyl dihydrogen phosphate

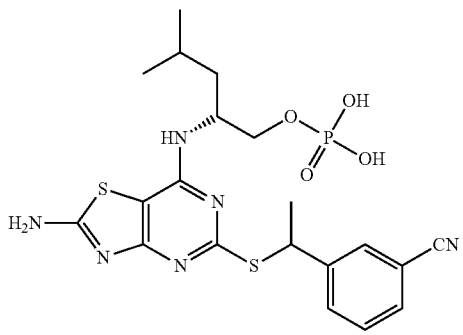

The title compound was synthesized from 3-{1-[(2-amino-7-{[(1R)-1-(hydroxymethyl)-3-methylbutyl]amino}[1,3]thiazolo[4,5-d]pyrimidin-5-yl)sulfanyl]ethyl}benzonitrile (Karlström S., et al., *J. Med. Chem.*, 2013, 56, 3177-3190; WO 2006/107258) in 50% yield using the method described for Example 1. The product is a mixture of two diastereomers. $^1$H NMR (600 MHz, DMSO-d$_6$) δ$_H$ ppm 8.17 (br. s., 1H) 7.99 (br. s., 4H) 8.04 (br. s., 1H) 7.92 (t, J=1.6 Hz, 1H) 7.90 (t, J=1.7 Hz, 1H) 7.80-7.85 (m, 2H) 7.67-7.70 (m, 2H) 7.56 (t, J=7.8 Hz, 1H) 7.51 (t, J=7.8 Hz, 1H) 7.26 (br. s., 4H) 5.03 (q, J=7.2 Hz, 1H) 5.03 (q, J=7.2 Hz, 1H) 4.18-4.29 (m, 1H) 4.06-4.16 (m, 1H) 3.64-3.74 (m, 4H) 1.66 (d, J=7.2 Hz, 3H) 1.65 (d, J=7.2 Hz, 3H) 1.53-1.62 (m, 2H) 1.37-1.51 (m, 4H) 0.88 (d, J=6.6 Hz, 3H) 0.86 (d, J=6.5 Hz, 3H) 0.85 (d, J=6.5 Hz, 3H) 0.78 (d, J=6.5 Hz, 3H). MS (ESI$^+$) m/z 509 [M+H]$^+$.

Example 1g (2R)-2-[(2-Amino-5-{[1-(3-carbamoylphenyl)ethyl]sulfanyl}[1,3]thiazolo[4,5-d]pyrimidin-7-yl)amino]-4-methylpentyl dihydrogen phosphate

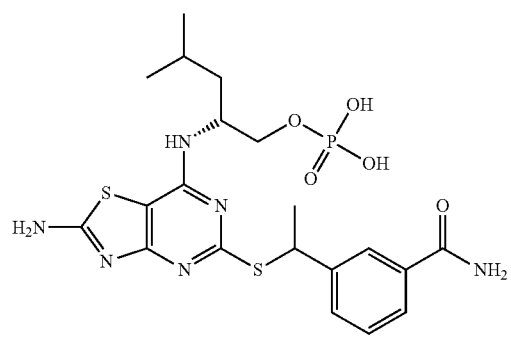

The title compound was synthesized from 3-{1-[(2-amino-7-{[(1R)-1-(hydroxymethyl)-3-methylbutyl]amino}[1,3]thiazolo[4,5-d]pyrimidin-5-yl)sulfanyl]ethyl}benzamide (Karlström S., et al., *J. Med. Chem.*, 2013, 56, 3177-3190; WO 2006/107258) as a single diastereomer, in 17% yield using the method described for Example 1. The product is a single diastereomer. $^1$H NMR (600 MHz, CD$_3$OD) δ$_H$ ppm 8.03 (t, J=1.85 Hz, 1H) 7.75 (ddd, J=7.70, 1.85, 1.10 Hz, 1H) 7.71 (dddd, J=7.70, 1.85, 1.10, 0.42 Hz, 1H) 7.42 (t, J=7.70 Hz, 1H) 5.14 (q, J=7.19 Hz, 1H) 4.35-4.43 (m, 1H) 3.98 (ddd, J=9.85, 5.11, 4.37 Hz, 1H) 3.91 (ddd, J=9.85, 5.20, 5.02 Hz, 1H) 1.73 (d, J=7.19 Hz, 3H) 1.58-1.67 (m, 2H) 1.48-1.55 (m, 1H) 0.91 (d, J=6.39 Hz, 3H) 0.76 (d, J=6.39 Hz, 3H). MS (ESI$^+$) m/z 527 [M+H]$^+$.

Example 1h (2R)-2-{[2-Amino-5-({1-[4-(methylsulfonyl)phenyl]ethyl}sulfanyl)[1,3]thiazolo[4,5-d]pyrimidin-7-yl]amino}-4-methylpentyl dihydrogen phosphate

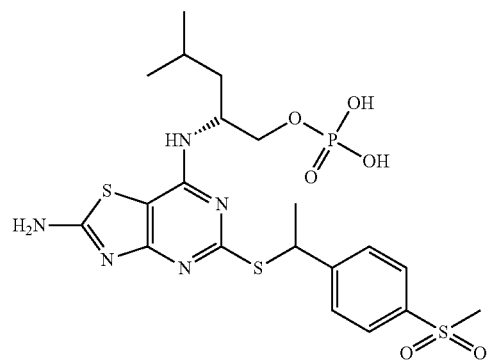

The title compound was synthesized from (2R)-2-{[2-amino-5-({1-[4-(methylsulfonyl)phenyl]ethyl}sulfanyl)[1,3]thiazolo[4,5-d]pyrimidin-7-yl]amino}-4-methylpentan-1-ol (Karlström S., et al., *J. Med. Chem.*, 2013, 56, 3177-3190; WO 2006/107258) as a single diastereomer, in 39% yield using the method described for Example 1. The product is a single diastereomer. $^1$H NMR (600 MHz, DMSO-d$_6$) δ$_H$ ppm 8.22 (br. s., 2H) 7.83-7.88 (m, 2H) 7.73-7.78 (m, 2H) 7.34 (br. s., 1H) 5.08 (q, J=7.3 Hz, 1H) 4.22-4.33 (m, 1H) 3.88 (dt, J=9.9, 5.4 Hz, 1H) 3.76 (td, J=9.9, 6.1 Hz, 1H) 3.18 (s, 3H) 1.64 (d, J=7.3 Hz, 3H) 1.53-1.61 (m, 1H) 1.51 (ddd, J=13.6, 10.3, 4.9 Hz, 1H) 1.37 (ddd, J=13.6, 9.2, 4.3 Hz, 1H) 0.85 (d, J=6.6 Hz, 3H) 0.72 (d, J=6.6 Hz, 3H). MS (ESI$^+$) m/z 562 [M+H]$^+$.

Example 1i (2R)-2-[(2-Amino-5-{[4-(methylsulfonyl)benzyl]sulfanyl}[1,3]thiazolo[4,5-d]pyrimidin-7-yl)amino]-4-methylpentyl dihydrogen phosphate

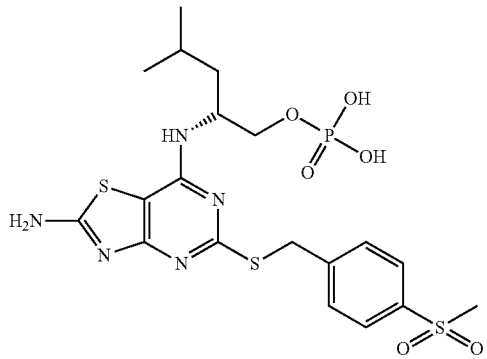

The title compound was synthesized from (2R)-2-[(2-amino-5-{[4-(methylsulfonyl)benzyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in 22% yield using the method described for Example 1. $^1$H NMR (600 MHz, DMSO-d$_6$) δ$_H$ ppm 8.02 (br. s., 2H) 7.81-7.86 (m, 2H) 7.66-7.71 (m, 2H) 7.17 (br. s., 2H) 4.45 (d, J=14.3 Hz, 1H) 4.39 (d, J=14.3 Hz, 1H) 4.20-4.34 (m, 1H) 3.67-3.76 (m, 2H) 3.17 (s, 3H) 1.52-1.61 (m, 1H) 1.46 (ddd, J=13.7, 9.0, 6.0 Hz, 1H) 1.38 (ddd, J=13.7, 8.1, 5.5 Hz, 1H) 0.83 (d, J=6.6 Hz, 3H) 0.78 (d, J=6.4 Hz, 3H). MS (ESI$^+$) m/z 548 [M+H]$^+$.

Example 1j (2R)-2-({2-Amino-5-[(1-pyridin-2-ylethyl)sulfanyl][1,3]thiazolo[4,5-d]pyrimidin-7-yl}amino)-4-methylpentyl dihydrogen phosphate

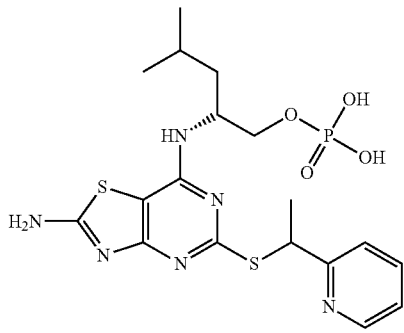

The title compound was synthesized from (2R)-2-({2-amino-5-[(1-pyridin-2-ylethyl) sulfanyl][1,3]thiazolo[4,5-d]pyrimidin-7-yl}amino)-4-methylpentan-1-ol (Karlström S., et al., *J. Med. Chem.*, 2013, 56, 3177-3190; WO 2006/107258) in 43% yield using the method described for Example 1. The product is a mixture of two diastereomers. $^1$H NMR (600 MHz, DMSO-d$_6$) δ$_H$ ppm 8.51 (ddd, J=4.8, 1.9, 1.0 Hz, 1H) 8.51 (ddd, J=4.8, 1.9, 1.0 Hz, 1H) 8.00 (br. s., 4H) 7.74 (ddd, J=7.9, 7.4, 1.9 Hz, 1H) 7.73 (ddd, J=7.9, 7.4, 1.9 Hz, 1H) 7.51 (dt, J=7.9, 1.0 Hz, 1H) 7.49 (dt, J=7.9, 1.0 Hz, 1H) 7.47 (br. s., 1H) 7.25 (ddd, J=7.4, 4.8, 1.0 Hz, 1H) 7.23 (ddd, J=7.4, 4.8, 1.0 Hz, 1H) 7.17 (br. s., 4H) 5.13 (q, J=7.0 Hz, 1H) 5.09 (q, J=7.0 Hz, 1H) 4.34-4.48 (m, 1H) 4.15-4.29 (m, 1H) 3.66-3.83 (m, 4H) 1.67 (d, J=7.0 Hz, 3H) 1.66 (d, J=7.0 Hz, 3H) 1.54-1.66 (m, 2H) 1.45-1.54 (m, 2H) 1.41 (ddd, J=13.8, 8.5, 5.3 Hz, 1H) 1.39 (ddd, J=13.8, 8.5, 5.3 Hz, 1H) 0.88 (d, J=6.6 Hz, 3H) 0.86 (d, J=6.7 Hz, 3H) 0.85 (d, J=6.6 Hz, 3H) 0.78 (d, J=6.6 Hz, 3H). MS (ESI$^+$) m/z 485 [M+H]$^+$.

Example 1k (2R)-2-[(2-Amino-5-{[(1S)-1-phenylethyl]sulfanyl}[1,3]thiazolo[4,5-d]pyrimidin-7-yl)amino]-4-methylpentyl dimethyl phosphate

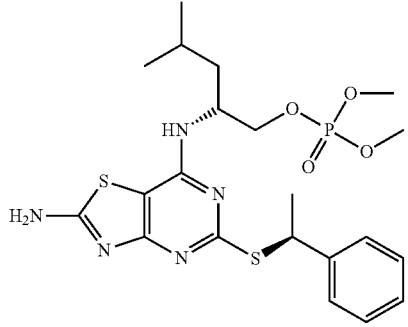

The title compound was synthesized from (2R)-2-[(2-amino-5-{[(1S)-1-phenylethyl] sulfanyl}-[1,3] thiazolo[4,5-d]pyrimidin-7-yl)amino]-4-methylpentan-1-ol (Karlström S., et al., *J. Med. Chem.*, 2013, 56, 3177-3190; WO 2006/107258) in 27% yield using the method described for Example 1 with the exception that MeOH, instead of THF and water, was added after 1 h at ice-bath temperature. $^1$H NMR (600 MHz, CD$_3$OD) δ$_H$ ppm 7.45-7.48 (m, 2H) 7.30-7.34 (m, 2H) 7.20-7.24 (m, 1H) 5.06 (q, J=7.1 Hz, 1H) 4.67-4.74 (m, 1H) 3.97 (ddd, J=10.2, 6.6, 5.7 Hz, 1H) 3.94 (ddd, J=10.2, 6.5, 4.9 Hz, 1H) 3.68 (d, J=11.1 Hz, 3H) 3.63 (d, J=11.1 Hz, 3H) 1.72-1.79 (m, 1H) 1.72 (d, J=7.1 Hz, 3H) 1.62 (ddd, J=13.9, 10.5, 5.0 Hz, 1H) 1.42 (ddd, J=13.9, 9.3, 4.4 Hz, 1H) 0.99 (d, J=6.7 Hz, 3H) 0.97 (d, J=6.6 Hz, 3H). MS (ESI$^+$) m/z 512 [M+H]$^+$.

Example 11

(2R)-2-[(2-Amino-5-{[(1S)-1-phenylethyl]sulfanyl}[1,3]thiazolo[4,5-d]pyrimidin-7-yl)amino]-4-methylpentyl diethyl phosphate

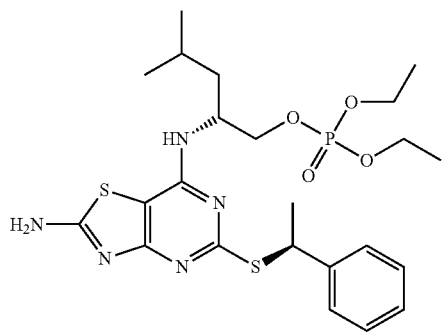

The title compound was synthesized from (2R)-2-[(2-amino-5-{[(1S)-1-phenylethyl]sulfanyl}-[1,3] thiazolo[4,5-d]pyrimidin-7-yl)amino]-4-methylpentan-1-ol (Karlström S., et al., *J. Med. Chem.*, 2013, 56, 3177-3190; WO 2006/107258) in 68% yield using the method described for Example 1 with the exception that EtOH, instead of THF and water, was added after 1 h at ice-bath temperature. $^1$H NMR (600 MHz, CD$_3$OD) δ$_H$ ppm 7.45-7.48 (m, 2H) 7.29-7.34 (m, 2H) 7.20-7.24 (m, 1H) 5.05 (q, J=7.1 Hz, 1H) 4.66-4.74 (m, 1H) 4.01 (dq, J=8.2, 7.1 Hz, 2H) 3.93-3.98 (m, J=8.0, 7.0, 7.0, 7.0, 3.4 Hz, 2H) 3.92-3.95 (m, 2H) 1.72-1.79 (m, 1H) 1.72 (d, J=7.1 Hz, 3H) 1.62 (ddd, J=13.8, 10.4, 5.0 Hz, 1H) 1.41 (ddd, J=13.8, 9.2, 4.5 Hz, 1H) 1.23 (td, J=7.1, 1.0 Hz, 3H) 1.16 (td, J=7.0, 1.0 Hz, 3H) 0.99 (d, J=6.7 Hz, 3H) 0.97 (d, J=6.6 Hz, 3H). MS (ESI$^+$) m/z 540 [M+H]$^+$.

Example 1m (2R)-2-[(2-Amino-5-{[(1S)-1-phenylethyl]sulfanyl}[1,3]thiazolo[4,5-d]pyrimidin-7-yl)amino]-4-methylpentyl bis(1-methylethyl) phosphate

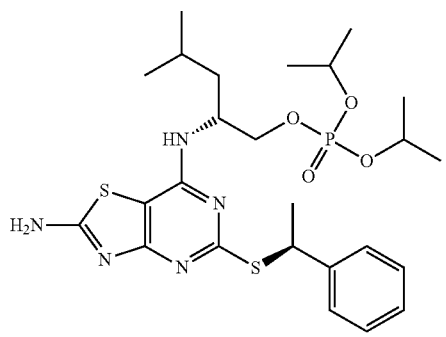

The title compound was synthesized from (2R)-2-[(2-amino-5-{[(1S)-1-phenylethyl]sulfanyl}-[1,3] thiazolo[4,5-d]pyrimidin-7-yl)amino]-4-methylpentan-1-ol (Karlström S., et al., *J. Med. Chem.*, 2013, 56, 3177-3190; WO 2006/107258) in 29% yield using the method described for Example 1 with the exception that i-PrOH, instead of THF and water, was added after 1 h at ice-bath temperature. The product was a mixture of mono- and di-isopropyl phosphate esters, that were separated by preparatory HPLC. $^1$H NMR (600 MHz, CD$_3$OD) δ$_H$ ppm 7.47 (dd, J=8.1, 1.1 Hz, 2H) 7.30-7.35 (m, 2H) 7.23 (tt, J=7.2, 1.4 Hz, 1H) 5.06 (q, J=7.2 Hz, 1H) 4.71 (br. s., 1H) 4.51 (sxt, J=6.3 Hz, 1H) 4.44 (sxt, J=6.3 Hz, 1H) 3.85-3.95 (m, 2H) 1.73-1.79 (m, 1H) 1.72 (d, J=7.0 Hz, 3H) 1.62 (ddd, J=13.7, 10.4, 5.2 Hz, 1H) 1.41 (ddd, J=13.8, 9.2, 4.4 Hz, 1H) 1.24 (d, J=6.1 Hz, 3H) 1.21 (d, J=6.1 Hz, 3H) 1.19 (d, J=6.1 Hz, 3H) 1.13 (d, J=6.1 Hz, 3H) 0.99 (d, J=6.7 Hz, 3H) 0.98 (d, J=6.7 Hz, 3H). MS (ESI$^+$) m/z 540 [M+H]$^+$.

Example 1n (2R)-2-[(2-Amino-5-{[(1S)-1-phenylethyl]sulfanyl}[1,3]thiazolo[4,5-d]pyrimidin-7-yl)amino]-4-methylpentyl 1-methylethyl hydrogen phosphate

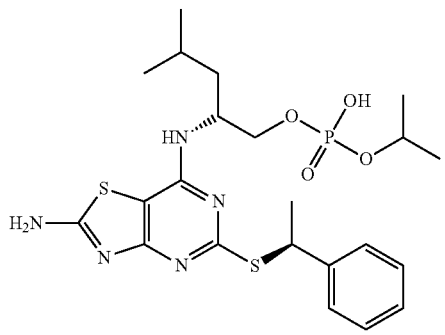

The title compound was synthesized from (2R)-2-[(2-amino-5-{[(1S)-1-phenylethyl] sulfanyl}-[1,3] thiazolo[4,5-d]pyrimidin-7-yl)amino]-4-methylpentan-1-ol (Karlström S., et al., *J. Med. Chem.*, 2013, 56, 3177-3190; WO 2006/107258) in 37% yield using the method described for Example 1 with the exception that i-PrOH, instead of THF and water, was added after 1 h at ice-bath temperature. The product was a mixture of mono- and di-isopropyl phosphate esters, that were separated by preparatory HPLC. $^1$H NMR (600 MHz, CD$_3$OD) δ$_H$ ppm 7.47 (dd, J=8.2, 1.2 Hz, 2H) 7.32-7.38 (m, 2H) 7.26 (tt, J=7.4, 1.5 Hz, 1H) 5.13 (q, J=7.0 Hz, 1H) 4.68 (br. s., 1H) 4.31-4.38 (m, 1H) 3.81-3.89 (m, 2H) 1.78 (d, J=7.0 Hz, 3H) 1.67-1.77 (m, 2H) 1.50-1.56 (m, 1H) 1.18 (d, J=6.1 Hz, 3H) 1.11 (d, J=6.4 Hz, 3H) 0.99 (d, J=6.4 Hz, 3H) 0.97 (d, J=6.7 Hz, 3H). MS (ESI$^+$) m/z 526 [M+H]$^+$.

Example 1o (2R)-2-[(2-Amino-5-{[1-(2-fluorophenyl)ethyl]sulfanyl}[1,3]thiazolo[4,5-d]pyrimidin-7-yl)amino]-4-methylpentyl diethyl phosphate

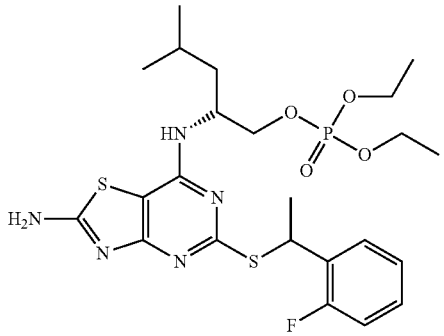

The title compound was synthesized from (2R)-2-[(2-amino-5-{[1-(2-fluorophenyl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in 46% yield using the method described for Example 1 with the exception that EtOH, instead of THF and water, was added after 1 h at ice-bath temperature. The product is a mixture of two diastereomers. 1H NMR (600 MHz, DMSO-d$_6$) δ$_H$ ppm 8.06 (s, 4H) 7.53-7.58 (m, 2H) 7.27-7.33 (m, 2H) 7.12-7.20 (m, 6H) 5.22 (q, J=7.0 Hz, 2H) 4.38-4.55 (m, 2H) 3.81-4.00 (m, 12H) 1.67 (d, J=7.0 Hz, 3H) 1.65 (d, J=7.0 Hz, 3H) 1.58-1.66 (m, 2H) 1.54 (ddd, J=18.7, 5.3, 5.0 Hz, 2H) 1.28-1.36 (m, 2H) 1.16 (td, J=7.0, 0.7 Hz, 3H) 1.15 (td, J=7.0, 0.7 Hz, 3H) 1.11 (td, J=7.0, 0.8 Hz, 6H) 0.89 (d, J=6.6 Hz, 3H) 0.88 (d, J=6.6 Hz, 3H) 0.86 (d, J=6.6 Hz, 3H) 0.81 (d, J=6.6 Hz, 3H). MS (ESI$^+$) m/z 558 [M+H]$^+$.

Example 1p (2R)-2-[(2-Amino-5-{[1-(2-chlorophenyl)ethyl]sulfanyl}[1,3]thiazolo[4,5-d]pyrimidin-7-yl)amino]-4-methylpentyl diethyl phosphate

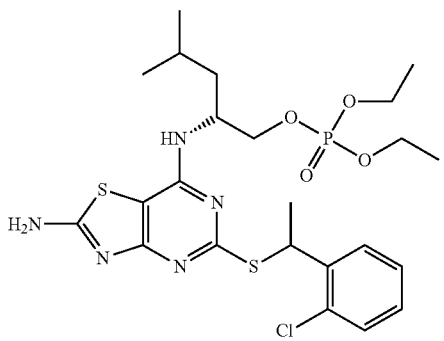

The title compound was synthesized from (2R)-2-[(2-amino-5-{[1-(2-chlorophenyl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in 36% yield using the method described for Example 1 with the exception that EtOH, instead of THF and water, was added after 1 h at ice-bath temperature. The two diastereomers were separated by preparatory HPLC (basic method).

Diastereomer A: $^1$H NMR (600 MHz, DMSO-d$_6$) δ$_H$ ppm 8.06 (s, 2H) 7.63 (dd, J=7.8, 1.7 Hz, 1H) 7.45 (dd, J=8.0, 1.3 Hz, 1H) 7.34 (ddd, J=7.8, 7.4, 1.3 Hz, 1H) 7.28 (ddd, J=8.0, 7.4, 1.7 Hz, 1H) 7.15 (d, J=8.2 Hz, 1H) 5.35 (q, J=7.0 Hz, 1H) 4.41-4.52 (m, 1H) 3.95-4.01 (m, 1H) 3.86-3.96 (m, 5H) 1.67 (d, J=7.0 Hz, 3H) 1.58-1.65 (m, 1H) 1.55 (ddd, J=13.5, 10.4, 5.0 Hz, 1H) 1.30 (ddd, J=13.5, 9.2, 4.5 Hz, 1H) 1.15 (td, J=7.1, 0.7 Hz, 3H) 1.11 (td, J=7.1, 0.7 Hz, 3H) 0.87 (d, J=6.6 Hz, 3H) 0.78 (d, J=6.6 Hz, 3H). MS (ESI$^+$) m/z 574 [M+H]$^+$.

Diastereomer B: $^1$H NMR (600 MHz, DMSO-d$_6$) δ$_H$ ppm 8.06 (s, 2H) 7.63 (dd, J=7.8, 1.7 Hz, 1H) 7.45 (dd, J=7.9, 1.3 Hz, 1H) 7.35 (ddd, J=7.8, 7.4, 1.3 Hz, 1H) 7.28 (ddd, J=7.9, 7.4, 1.7 Hz, 1H) 7.17 (d, J=8.2 Hz, 1H) 5.36 (q, J=7.1 Hz, 1H) 4.42-4.54 (m, 1H) 3.93 (dq, J=8.2, 7.1 Hz, 2H) 3.84-3.92 (m, 2H) 3.78-3.86 (m, 2H) 1.65 (d, J=7.0 Hz, 3H) 1.60-1.70 (m, 1H) 1.57 (ddd, J=13.7, 10.2, 4.8 Hz, 1H) 1.32 (ddd, J=13.7, 9.1, 4.4 Hz, 1H) 1.15 (td, J=7.1, 0.8 Hz, 3H) 1.09 (td, J=7.1, 0.8 Hz, 3H) 0.90 (d, J=6.6 Hz, 3H) 0.87 (d, J=6.6 Hz, 3H). MS (ESI$^+$) m/z 574 [M+H]$^+$.

Example 1q (2R)-2-[(2-Amino-5-{[1-(5-chloropyridin-2-yl)ethyl]sulfanyl}[1,3]thiazolo[4,5-d]pyrimidin-7-yl)amino]-4-methylpentyl diethyl phosphate

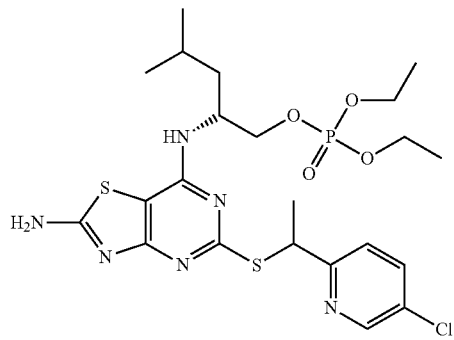

The title compound was synthesized from (2R)-2-[(2-amino-5-{[1-(5-chloropyridin-2-yl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in 27% yield using the method described for Example 1 with the exception that EtOH, instead of THF and water, was added after 1 h at ice-bath temperature. The product was isolated as a TFA salt after preparatory HPLC purification (acidic method). The product is a mixture of two diastereomers. $^1$H NMR (600 MHz, DMSO-d$_6$) δ$_H$ ppm 8.58 (dd, J=2.6, 0.7 Hz, 1H) 8.57 (dd, J=2.6, 0.7 Hz, 1H) 8.36 (br. s., 2H) 8.34 (br. s., 2H) 7.89 (dd, J=8.5, 2.6 Hz, 1H) 7.88 (dd, J=8.5, 2.6 Hz, 1H) 7.60 (dd, J=8.5, 0.7 Hz, 1H) 7.57 (dd, J=8.5, 0.7 Hz, 1H) 7.58 (br. s., 2H) 5.16 (q, J=7.1 Hz, 1H) 5.09 (q, J=7.2 Hz, 1H) 4.51-4.62 (m, 1H) 4.30-4.40 (m, 1H) 3.83-4.02 (m, 12H) 1.67 (d, J=7.1 Hz, 3H) 1.66 (d, J=7.1 Hz, 3H) 1.57-1.67 (m, 2H) 1.49-1.57 (m, 2H) 1.35 (ddd, J=13.6, 9.1, 4.3 Hz, 1H) 1.31 (ddd, J=13.6, 9.1, 4.3 Hz, 1H) 1.15 (dt, J=7.1, 0.8 Hz, 3H) 1.15 (td, J=7.1, 0.8 Hz, 3H) 1.12 (td, J=7.1, 0.8 Hz, 3H) 1.11 (td, J=7.1, 0.8 Hz, 3H) 0.90 (d, J=6.7 Hz, 3H) 0.87 (d, J=6.6 Hz, 6H) 0.76 (d, J=6.5 Hz, 3H). MS (ESI⁺) m/z 575 [M+H]⁺.

Example 1r (2R)-2-[(2-Amino-5-{[1-(3-fluoropyridin-2-yl)ethyl]sulfanyl}[1,3]thiazolo[4,5-d]pyrimidin-7-yl)amino]-4-methylpentyl diethyl phosphate

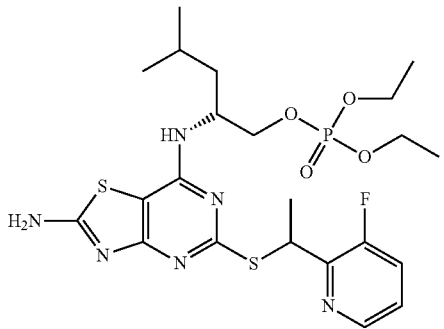

The title compound was synthesized from (2R)-2-[(2-amino-5-{[1-(3-fluoropyridin-2-yl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in 47% yield using the method described for Example 1 with the exception that EtOH, instead of THF and water, was added after 1 h at ice-bath temperature. The product was isolated as a TFA salt after preparatory HPLC purification (acidic method). The product is a mixture of two diastereomers. ¹H NMR (600 MHz, DMSO-d₆) δ$_H$ ppm 8.48 (br. s., 2H) 8.46 (br. s., 2H) 8.41-8.43 (m, 2H) 7.74 (ddd, J=10.1, 8.4, 1.4 Hz, 1H) 7.79 (br. s., 2H) 7.74 (ddd, J=10.1, 8.4, 1.4 Hz, 1H) 7.44 (ddd, J=8.4, 4.4, 3.2 Hz, 1H) 7.43 (ddd, J=8.4, 4.4, 3.2 Hz, 1H) 5.47 (q, J=6.9 Hz, 1H) 5.46 (q, J=6.9 Hz, 1H) 4.51-4.64 (m, 2H) 3.99-4.05 (m, 1H) 3.85-4.00 (m, 11H) 1.72 (d, J=7.0 Hz, 3H) 1.70 (d, J=7.0 Hz, 3H) 1.60-1.69 (m, 2H) 1.57 (ddd, J=13.6, 10.0, 5.0 Hz, 2H) 1.37 (ddd, J=13.6, 9.2, 4.5 Hz, 1H) 1.37 (ddd, J=13.6, 9.2, 4.5 Hz, 1H) 1.16 (td, J=7.0, 0.7 Hz, 3H) 1.15 (td, J=7.0, 0.7 Hz, 3H) 1.12 (td, J=7.0, 0.7 Hz, 3H) 1.10 (td, J=7.0, 0.7 Hz, 3H) 0.91 (d, J=6.6 Hz, 3H) 0.91 (d, J=6.6 Hz, 3H) 0.88 (d, J=6.6 Hz, 3H) 0.86 (d, J=6.6 Hz, 3H). MS (ESI⁺) m/z 558 [M+H]⁺.

Example 1s (2R)-2-[(2-Amino-5-{[1-(3-cyanophenyl)ethyl]sulfanyl}[1,3]thiazolo[4,5-d]pyrimidin-7-yl)amino]-4-methylpentyl diethyl phosphate

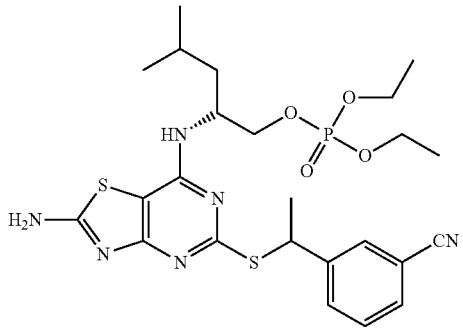

The title compound was synthesized from 3-{1-[(2-amino-7-{[(1R)-1-(hydroxymethyl)-3-methylbutyl]amino}[1,3]thiazolo[4,5-d]pyrimidin-5-yl)sulfanyl]ethyl}benzonitrile (Karlström S., et al., *J. Med. Chem.*, 2013, 56, 3177-3190; WO 2006/107258) in 50% yield using the method described for Example 1 with the exception that EtOH, instead of THF and water, was added after 1 h at ice-bath temperature. The product was isolated as a TFA salt after preparatory HPLC purification (acidic method). The product is a mixture of two diastereomers. ¹H NMR (600 MHz, DMSO-d₆) δ$_H$ ppm 8.36 (br. s., 4H) 7.95 (dd, J=1.8, 1.2 Hz, 1H) 7.93 (dd, J=1.9, 1.2 Hz, 1H) 7.84 (ddd, J=7.8, 1.8, 1.5 Hz, 1H) 7.83 (ddd, J=7.8, 1.8, 1.5 Hz, 1H) 7.72 (ddd, J=7.7, 1.5, 1.2 Hz, 1H) 7.71 (ddd, J=7.7, 1.5, 1.2 Hz, 1H) 7.55 (dd, J=7.8, 7.7 Hz, 1H) 7.53 (dd, J=7.8, 7.7 Hz, 1H) 5.08 (q, J=7.2 Hz, 1H) 5.06 (q, J=7.2 Hz, 1H) 4.45-4.56 (m, 1H) 4.30-4.40 (m, 1H) 3.84-3.99 (m, 12H) 1.68 (d, J=7.2 Hz, 3H) 1.65 (d, J=7.2 Hz, 3H) 1.49-1.65 (m, 4H) 1.34 (ddd, J=13.6, 9.1, 4.3 Hz, 1H) 1.31 (ddd, J=13.6, 9.1, 4.3 Hz, 1H) 1.16 (td, J=7.1, 0.6 Hz, 6H) 1.13 (td, J=7.1, 0.8 Hz, 3H) 1.10 (td, J=7.1, 0.7 Hz, 3H) 0.90 (d, J=6.6 Hz, 3H) 0.86 (d, J=6.5 Hz, 3H) 0.86 (d, J=6.5 Hz, 3H) 0.73 (d, J=6.5 Hz, 3H). MS (ESI⁺) m/z 565 [M+H]⁺.

Example 2

Preparation of [7-{[(1R)-1-(Hydroxymethyl)-3-methylbutyl]amino}-2-imino-5-{[(1S)-1-phenylethyl]sulfanyl}[1,3]thiazolo[4,5-d]pyrimidin-3(2H)-yl]methyl dihydrogen phosphate

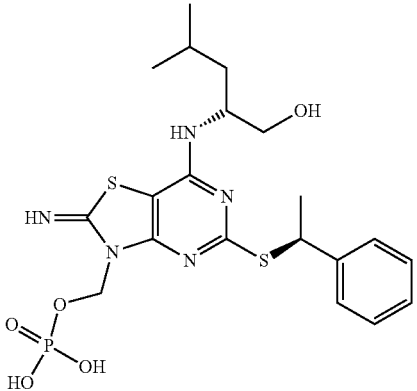

To a mixture of (2R)-2-[(2-amino-5-{[(1S)-1-phenylethyl]sulfanyl}-[1,3] thiazolo[4,5-d]pyrimidin-7-yl)amino]-4-methylpentan-1-ol (Karlström S., et al., *J. Med. Chem.*, 2013, 56, 3177-3190; WO 2006/107258) (40 mg, 0.10 mmol), K₂CO₃ (28 mg, 0.20 mmol) and sodium iodide (22 mg, 0.15 mmol) in CH₃CN was added di-tert-butyl chloromethyl phosphate (39 mg, 0.15 mmol). The reaction mixture was stirred at 50° C. for 21 h. The reaction mixture was evaporated and DCM (5 mL) and water (2 mL) were added. The phases were separated and the organic phase was washed with water (2×2 mL) and brine (2 mL), dried over MgSO₄, filtered and evaporated to yield 60 mg of crude product as an orange solid. To the crude material in dioxane (1.5 mL) was added conc. HCl (30 μL, 0.38 mmol) and the mixture was stirred at room temperature for 2 h. To the mixture was added 2M NaOH (300 µL), which resulted in a pH of ca. 7. The mixture was diluted with MeOH, DMSO and water, filtered and purified by preparative HPLC (basic method). The pure fractions were pooled, evaporated, and dried in vacuum to yield 7.2 mg (14%) of pure product as a white solid. The product was assumed to be the diammonium salt after purification. $^1$H NMR (600 MHz, CD$_3$OD) $\delta_H$ ppm 7.46-7.50 (m, 2H) 7.30-7.35 (m, 2H) 7.20-7.24 (m, 1H) 5.86-5.93 (m, 2H) 5.02 (q, J=7.12 Hz, 1H) 4.42-4.57 (m, 1H) 3.53 (dd, J=11.11, 5.42 Hz, 1H) 3.50 (dd, J=11.11, 5.32 Hz, 1H) 1.72 (d, J=7.12 Hz, 3H) 1.62-1.71 (m, 1H) 1.53 (ddd, J=13.95, 10.10, 4.87 Hz, 1H) 1.45 (ddd, J=13.95, 9.18, 4.58 Hz, 1H) 0.96 (d, J=6.71 Hz, 3H) 0.94 (d, J=6.60 Hz, 3H). MS (ESI$^+$) m/z 514 [M+H]$^+$.

Example 2b

[5-{[1-(2-Fluorophenyl)ethyl]sulfanyl}-7-{[(1R)-1-(hydroxymethyl)-3-methylbutyl]amino}-2-imino[1,3]thiazolo[4,5-d]pyrimidin-3(2H)-yl]methyl dihydrogen phosphate

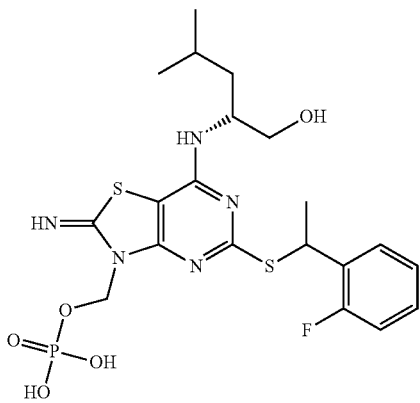

The title compound was synthesized from (2R)-2-[(2-amino-5-{[1-(2-fluorophenyl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in 12% yield using the method described for Example 2. The product is a mixture of two diastereomers. $^1$H NMR (600 MHz, CD$_3$OD) $\delta_H$ ppm 7.54-7.60 (m, 2H) 7.23-7.29 (m, 2H) 7.12-7.17 (m, 2H) 7.06-7.13 (m, 2H) 5.87-5.96 (m, 4H) 5.32 (q, J=7.17 Hz, 1H) 5.31 (q, J=7.17 Hz, 1H) 4.46-4.53 (m, 1H) 4.41-4.48 (m, 1H) 3.62 (dd, J=11.20, 5.08 Hz, 1H) 3.55 (dd, J=11.20, 5.56 Hz, 1H) 3.51 (dd, J=11.20, 5.12 Hz, 1H) 3.47 (dd, J=11.20, 4.97 Hz, 1H) 1.72 (d, J=7.17 Hz, 3H) 1.71 (d, J=7.17 Hz, 3H) 1.60-1.69 (m, 2H) 1.51-1.59 (m, 2H) 1.43 (ddd, J=13.97, 9.06, 4.46 Hz, 1H) 1.42 (ddd, J=13.79, 9.06, 4.46 Hz, 1H) 0.96 (d, J=6.71 Hz, 3H) 0.94 (d, J=6.70 Hz, 3H) 0.94 (d, J=6.50 Hz, 3H) 0.89 (d, J=6.56 Hz, 3H). MS (ESI$^+$) m/z 532 [M+H]$^+$.

Example 2c

[5-{[1-(2-Chlorophenyl)ethyl]sulfanyl}-7-{[(1R)-1-(hydroxymethyl)-3-methylbutyl]amino}-2-imino[1,3]thiazolo[4,5-d]pyrimidin-3(2H)-yl]methyl dihydrogen phosphate

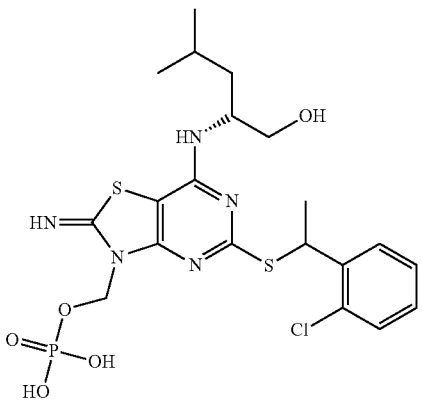

The title compound was synthesized from (2R)-2-[(2-amino-5-{[1-(2-chlorophenyl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in 12% yield using the method described for Example 2. The product is a mixture of two diastereomers. $^1$H NMR (600 MHz, CD$_3$OD) $\delta_H$ ppm 7.67 (dd, J=7.78, 1.70 Hz, 1H) 7.66 (dd, J=7.78, 1.70 Hz, 1H) 7.43 (dd, J=7.94, 1.35 Hz, 1H) 7.42 (dd, J=7.94, 1.35 Hz, 1H) 7.29 (ddd, J=7.78, 7.42, 1.35 Hz, 2H) 7.24 (ddd, J=7.94, 7.42, 1.70 Hz, 1H) 7.23 (ddd, J=7.94, 7.42, 1.70 Hz, 1H) 5.86-5.94 (m, 4H) 5.48 (q, J=7.14 Hz, 1H) 5.48 (q, J=7.14 Hz, 1H) 4.43-4.54 (m, 2H) 3.64 (dd, J=11.20, 4.93 Hz, 1H) 3.56 (dd, J=11.22, 5.51 Hz, 1H) 3.48 (dd, J=11.29, 4.80 Hz, 1H) 3.42 (dd, J=11.20, 4.93 Hz, 1H) 1.71 (d, J=7.14 Hz, 3H) 1.69 (d, J=7.14 Hz, 3H) 1.53-1.70 (m, 4H) 1.41 (ddd, J=13.69, 9.15, 4.48 Hz, 1H) 1.40 (ddd, J=13.69, 9.15, 4.48 Hz, 1H) 0.96 (d, J=6.56 Hz, 3H) 0.95 (d, J=6.56 Hz, 3H) 0.93 (d, J=6.71 Hz, 3H) 0.85 (d, J=6.56 Hz, 3H). MS (ESI$^+$) m/z 548 [M+H]$^+$.

Example 2d

[5-{[1-(5-Chloropyridin-2-yl)ethyl]sulfanyl}-7-{[(1R)-1-(hydroxymethyl)-3-methylbutyl]amino}-2-imino[1,3]thiazolo[4,5-d]pyrimidin-3(2H)-yl]methyl dihydrogen phosphate

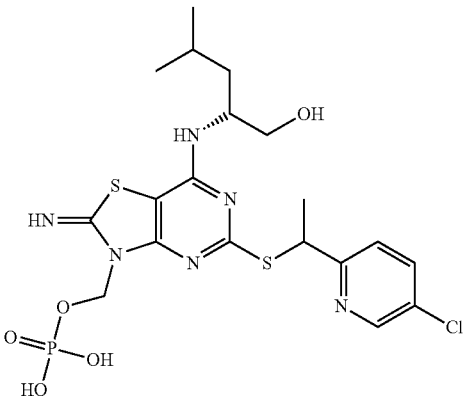

The title compound was synthesized from (2R)-2-[(2-amino-5-{[1-(5-chloropyridin-2-yl)ethyl]sulfanyl}[1,3]thiazolo[4,5-d]pyrimidin-7-yl)amino]-4-methylpentan-1-ol (Karlström S., et al., J. Med. Chem., 2013, 56, 3177-3190; WO 2006/107258) in 6% yield using the method described for Example 2. The product is a mixture of two diastereomers. $^1$H NMR (600 MHz, CD$_3$OD) $\delta_H$ ppm 8.49 (dd, J=2.46, 0.70 Hz, 1H) 8.48 (dd, J=2.46, 0.70 Hz, 1H) 7.83 (dd, J=8.41, 2.46 Hz, 1H) 7.83 (dd, J=8.41, 2.46 Hz, 1H) 7.68 (dd, J=8.41, 0.70 Hz, 1H) 7.67 (dd, J=8.41, 0.70 Hz, 1H) 5.87-5.94 (m, 2H) 5.81-5.87 (m, 2H) 5.15 (q, J=7.23 Hz, 1H) 5.12 (q, J=7.23 Hz, 1H) 4.41-4.50 (m, 1H) 4.25-4.35 (m, 1H) 3.54 (d, J=5.49 Hz, 2H) 3.45-3.52 (m, 2H) 1.71 (d, J=7.23 Hz, 3H) 1.70 (d, J=7.23 Hz, 3H) 1.56-1.69 (m, 2H) 1.47-1.54 (m, 2H) 1.42 (ddd, J=13.81, 9.23, 4.43 Hz, 1H) 1.41 (ddd, J=13.81, 9.23, 4.43 Hz, 1H) 0.95 (d, J=6.71 Hz, 3H) 0.92 (d, J=6.71 Hz, 3H) 0.92 (d, J=6.41 Hz, 3H) 0.83 (d, J=6.56 Hz, 3H). MS (ESI$^+$) m/z 549 [M+H]$^+$.

Example 2e

[7-{[(1R)-1-(Hydroxymethyl)-3-methylbutyl]amino}-2-imino-5-[(1-pyridin-2-ylethyl)sulfanyl][1,3]thiazolo[4,5-d]pyrimidin-3(2H)-yl]methyl dihydrogen phosphate

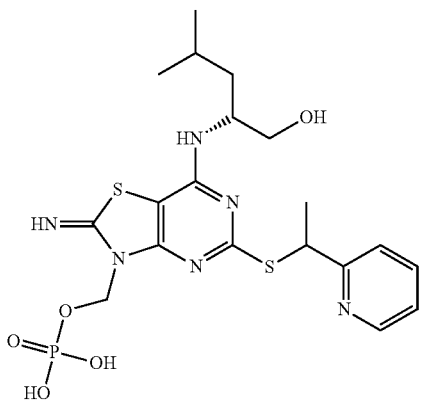

The title compound was synthesized from (2R)-2-({2-amino-5-[(1-pyridin-2-ylethyl) sulfanyl][1,3]thiazolo[4,5-d]pyrimidin-7-yl}amino)-4-methylpentan-1-ol (Karlström S., et al., J. Med. Chem., 2013, 56, 3177-3190; WO 2006/107258) in 4% yield using the method described for Example 2. The two diastereomers were separated by preparatory HPLC (basic method).

Diastereomer A: $^1$H NMR (600 MHz, CD$_3$OD) $\delta_H$ ppm 8.49 (ddd, J=4.95, 1.85, 1.00 Hz, 1H) 7.83 (ddd, J=7.89, 7.54, 1.85 Hz, 1H) 7.67 (ddd, J=7.89, 1.10, 1.00 Hz, 1H) 7.29 (ddd, J=7.54, 4.95, 1.10 Hz, 1H) 5.86 (dd, J=10.74, 9.88 Hz, 1H) 5.81 (dd, J=10.74, 9.65 Hz, 1H) 5.15 (q, J=7.28 Hz, 1H) 4.42-4.51 (m, 1H) 3.50 (dd, J=11.15, 5.52 Hz, 1H) 3.46 (dd, J=11.15, 5.46 Hz, 1H) 1.72 (d, J=7.28 Hz, 3H) 1.58-1.68 (m, 1H) 1.51 (ddd, J=13.94, 10.22, 4.87 Hz, 1H) 1.43 (ddd, J=13.94, 9.20, 4.45 Hz, 1H) 0.94 (d, J=6.56 Hz, 3H) 0.92 (d, J=6.56 Hz, 3H). MS (ESI$^+$) m/z 515 [M+H]$^+$.

Diastereomer B: $^1$H NMR (600 MHz, CD$_3$OD) $\delta_H$ ppm 8.49 (ddd, J=4.95, 1.85, 1.00 Hz, 1H) 7.82 (ddd, J=7.89, 7.54, 1.85 Hz, 1H) 7.68 (ddd, J=7.89, 1.10, 1.00 Hz, 1H) 7.29 (ddd, J=7.54, 4.95, 1.10 Hz, 1H) 5.87 (dd, J=10.74, 9.88 Hz, 1H) 5.81 (dd, J=10.74, 9.65 Hz, 1H) 5.13 (q, J=7.28 Hz, 1H) 4.28-4.37 (m, 1H) 3.56 (dd, J=11.15, 5.46 Hz, 1H) 3.52 (dd, J=11.15, 5.57 Hz, 1H) 1.71 (d, J=7.28 Hz, 3H) 1.57-1.68 (m, 1H) 1.50 (ddd, J=13.94, 10.22, 4.87 Hz, 1H) 1.42 (ddd, J=13.94, 9.20, 4.45 Hz, 1H) 0.92 (d, J=6.71 Hz, 3H) 0.84 (d, J=6.56 Hz, 3H). MS (ESI$^+$) m/z 515 [M+H]$^+$.

Example 2f

[5-{[1-(3-Fluoropyridin-2-yl)ethyl]sulfanyl}-7-{[(1R)-1-(hydroxymethyl)-3-methylbutyl]amino}-2-imino[1,3]thiazolo[4,5-d]pyrimidin-3(2H)-yl]methyl dihydrogen phosphate

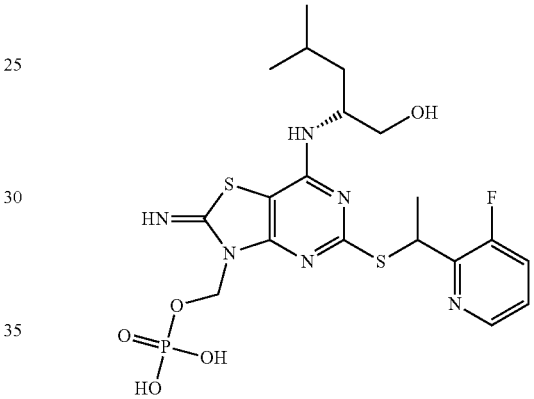

The title compound was synthesized from (2R)-2-[(2-amino-5-{[1-(3-fluoropyridin-2-yl)ethyl]sulfanyl}[1,3]thiazolo[4,5-d]pyrimidin-7-yl)amino]-4-methylpentan-1-ol (Karlström S., et al., J. Med. Chem., 2013, 56, 3177-3190; WO 2006/107258) in 19% yield using the method described for Example 2. The two diastereomers were separated by preparatory HPLC (basic method).

Diastereomer A: $^1$H NMR (600 MHz, CD$_3$OD) $\delta_H$ ppm 8.33 (dt, J=4.74, 1.32 Hz, 1H) 7.65 (ddd, J=9.96, 8.39, 1.32 Hz, 1H) 7.36 (ddd, J=8.39, 4.74, 4.12 Hz, 1H) 5.89 (t, J=10.40 Hz, 1H) 5.83 (t, J=10.40 Hz, 1H) 5.48 (q, J=7.15 Hz, 1H) 4.45-4.53 (m, 1H) 3.54 (dd, J=11.22, 5.44 Hz, 1H) 3.52 (dd, J=11.22, 5.29 Hz, 1H) 1.73 (d, J=7.15 Hz, 3H) 1.62-1.70 (m, 1H) 1.54 (ddd, J=13.85, 10.11, 5.01 Hz, 1H) 1.43 (ddd, J=13.85, 9.19, 4.52 Hz, 1H) 0.95 (d, J=6.71 Hz, 3H) 0.93 (d, J=6.56 Hz, 3H). MS (ESI$^+$) m/z 533 [M+H]$^+$.

Diastereomer B: $^1$H NMR (600 MHz, CD$_3$OD) $\delta_H$ ppm 8.34 (dt, J=4.7, 1.3 Hz, 1H) 7.64 (ddd, J=10.0, 8.4, 1.3 Hz, 1H) 7.36 (ddd, J=8.4, 4.7, 4.1 Hz, 1H) 5.89 (dd, J=10.7, 10.1 Hz, 1H) 5.83 (dd, J=10.7, 10.1 Hz, 1H) 5.48 (q, J=7.2 Hz, 1H) 4.41-4.53 (m, 1H) 3.59 (dd, J=11.2, 5.3 Hz, 1H) 3.56 (dd, J=11.2, 5.6 Hz, 1H) 1.75 (d, J=7.2 Hz, 3H) 1.62-1.70 (m, 1H) 1.54 (ddd, J=13.9, 10.1, 5.0 Hz, 1H) 1.43 (ddd, J=13.9, 9.2, 4.5 Hz, 1H) 0.95 (d, J=6.7 Hz, 3H) 0.92 (d, J=6.7 Hz, 3H). MS (ESI$^+$) m/z 533 [M+H]$^+$.

Example 2g

[5-{[1-(3-Cyanophenyl)ethyl]sulfanyl}-7-{[(1R)-1-(hydroxymethyl)-3-methylbutyl]amino}-2-imino[1,3]thiazolo[4,5-d]pyrimidin-3(2H)-yl]methyl dihydrogen phosphate

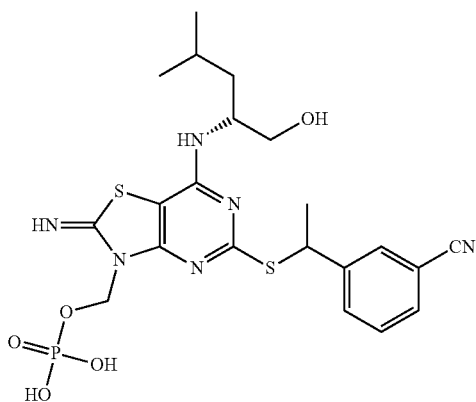

The title compound was synthesized from 3-{1-[(2-amino-7-{[(1R)-1-(hydroxymethyl)-3-methylbutyl]amino}[1,3]thiazolo[4,5-d]pyrimidin-5-yl)sulfanyl]ethyl}benzonitrile (Karlström S., et al., *J. Med. Chem.*, 2013, 56, 3177-3190; WO 2006/107258) in 22% yield using the method described for Example 2. The two diastereomers were separated by preparatory HPLC (basic method).

Diastereomer A: $^1$H NMR (600 MHz, CD$_3$OD) $\delta_H$ ppm 7.85-7.88 (m, 2H) 7.59 (dt, J=7.76, 1.38 Hz, 1H) 7.54 (dd, J=8.44, 7.76 Hz, 1H) 5.83 (d, J=9.82 Hz, 2H) 5.09 (q, J=7.21 Hz, 1H) 4.40-4.49 (m, 1H) 3.51 (dd, J=11.13, 5.49 Hz, 1H) 3.46 (dd, J=11.13, 5.35 Hz, 1H) 1.71 (d, J=7.21 Hz, 3H) 1.60-1.68 (m, 1H) 1.52 (ddd, J=13.85, 10.25, 4.91 Hz, 1H) 1.43 (ddd, J=13.85, 9.19, 4.35 Hz, 1H) 0.95 (d, J=6.71 Hz, 3H) 0.93 (d, J=6.56 Hz, 3H). MS (ESI$^+$) m/z 539 [M+H]$^+$.

Diastereomer B: $^1$H NMR (600 MHz, CD$_3$OD) $\delta_H$ ppm 7.86-7.89 (m, 2H) 7.58 (dt, J=7.8, 1.4 Hz, 1H) 7.53 (dd, J=8.4, 7.8 Hz, 1H) 5.83 (dd, J=10.6, 9.7 Hz, 1H) 5.81 (dd, J=10.6, 9.6 Hz, 1H) 5.08 (q, J=7.3 Hz, 1H) 4.28-4.38 (m, 1H) 3.57 (dd, J=11.4, 5.6 Hz, 1H) 3.55 (dd, J=11.4, 5.7 Hz, 1H) 1.70 (d, J=7.3 Hz, 3H) 1.57-1.66 (m, 1H) 1.50 (ddd, J=13.9, 10.4, 5.0 Hz, 1H) 1.41 (ddd, J=13.9, 9.3, 4.3 Hz, 1H) 0.92 (d, J=6.7 Hz, 3H) 0.82 (d, J=6.6 Hz, 3H). MS (ESI$^+$) m/z 539 [M+H]$^+$.

Example 2h

[5-{[(1S)-1-(5-Chloropyridin-2-yl)ethyl]sulfanyl}-7-{[(1R)-1-(hydroxymethyl)-3-methylbutyl]amino}-2-oxo[1,3]thiazolo[4,5-d]pyrimidin-3(2H)-yl]methyl dihydrogen phosphate

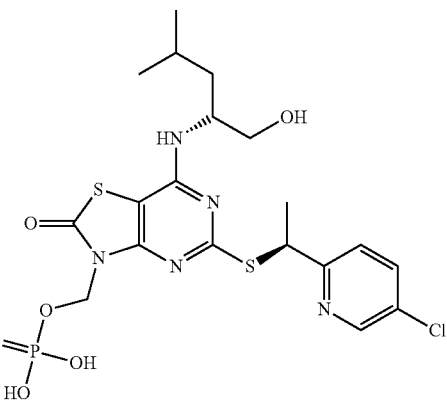

The title compound was synthesized from 5-{[(1S)-1-(5-chloropyridin-2-yl)ethyl]sulfanyl}-7-{[(1R)-1-(hydroxymethyl)-3-methylbutyl]amino}[1,3]thiazolo[4,5-d]pyrimidin-2(3H)-one (Karlström S., et al., *J. Med. Chem.*, 2013, 56, 3177-3190; WO2008/039138) in 39% yield using the method described for Example 2. $^1$H NMR (600 MHz, CD$_3$OD) $\delta_H$ ppm 8.49 (dd, J=2.53, 0.66 Hz, 1H) 7.86 (dd, J=8.47, 2.53 Hz, 1H) 7.77 (dd, J=8.47, 0.66 Hz, 1H) 5.67 (dd, J=9.30, 5.92 Hz, 1H) 5.63 (dd, J=9.30, 5.83 Hz, 1H) 5.23 (q, J=7.32 Hz, 1H) 4.35-4.48 (m, 1H) 3.51 (dd, J=11.06, 5.53 Hz, 1H) 3.45 (dd, J=11.06, 5.65 Hz, 1H) 1.68 (d, J=7.32 Hz, 3H) 1.58-1.66 (m, 1H) 1.49 (ddd, J=13.87, 10.27, 4.85 Hz, 1H) 1.41 (ddd, J=13.87, 9.27, 4.36 Hz, 1H) 0.93 (d, J=6.68 Hz, 3H) 0.90 (d, J=6.56 Hz, 3H). MS (ESI$^+$) m/z 550 [M+H]$^+$.

Example 3

Preparation of (2R)-2-[(5-{[(1S)-1-(5-chloropyridin-2-yl)ethyl]sulfanyl}-2-oxo-2,3-dihydro[1,3]thiazolo[4,5-d]pyrimidin-7-yl)amino]-4-methylpentyl dihydrogen phosphate

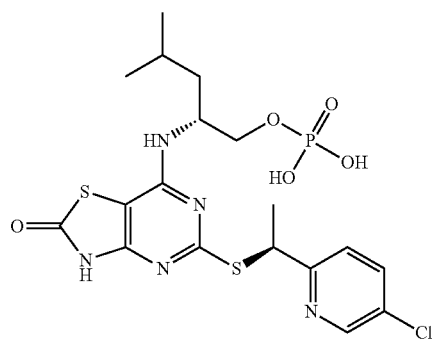 [SMILES: CC(C)C[C@H](COP(=O)(O)O)Nc1nc(S[C@@H](C)c2ccc(Cl)cn2)nc2[nH]c(=O)sc12]

Phosphorus oxychloride (383 mg, 2.5 mmol) was dissolved in THF (0.75 mL) and water (28 mg, 1.58 mmol) was added. The mixture was cooled in an ice-bath and pyridine (125 mg, 127 µL, 1.58 mmol) was added followed by 5-{[(1S)-1-(5-chloropyridin-2-yl)ethyl]sulfanyl}-7-{[(1R)-1-(hydroxymethyl)-3-methylbutyl]amino}[1,3]thiazolo[4,5-d]pyrimidin-2(3H)-one (Karlström S., et al., *J. Med. Chem.*, 2013, 56, 3177-3190; WO2008/039138) (110 mg, 0.25 mmol). The reaction mixture was stirred at ice-bath temperature for 2 h. Water (4 mL) was added and the mixture was stirred at room temperature for 1 h. The pH was adjusted to 11-12 with 5M NaOH (ca. 2.8 mL) and the mixture was washed with DCM (3×4 mL). The pH of the aqueous phase was adjusted to 1 by addition of conc. HCl (ca. 300 µL) which caused precipitation of crude product. The mixture was centrifuged and the supernatant was discarded. The remaining solid was washed with water (2 mL), centrifuged and the supernatant was discarded. The remaining solid was dissolved in MeOH and evaporated to yield 47 mg of 90% pure product. The crude material was dissolved in DMSO/water and the pH was adjusted to ca. 7 and purified by preparative HPLC (basic method). The pure fractions were pooled, evaporated, and dried in vacuum to yield 34 mg (24%) of pure product as an off-white solid. The product was assumed to be the diammonium salt after purification. $^1$H NMR (600 MHz, CD$_3$OD) $\delta_H$ ppm 8.47 (dd, J=2.54, 0.48 Hz, 1H) 7.84 (dd, J=8.42, 2.54 Hz, 1H) 7.62 (dd, J=8.42, 0.48 Hz, 1H) 5.17 (q, J=7.20 Hz, 1H) 4.53-4.68 (m, 1H) 3.88 (dt, J=10.13, 5.09 Hz, 1H) 3.83 (dt, J=10.13, 5.25 Hz, 1H) 1.72 (d, J=7.20 Hz, 3H) 1.65-1.73 (m, 1H) 1.60 (ddd, J=13.86, 9.91, 5.20 Hz, 1H) 1.54 (ddd, J=13.86, 9.04, 4.93 Hz, 1H) 0.96 (d, J=6.63 Hz, 3H) 0.94 (d, J=6.53 Hz, 3H). MS (ESI$^+$) m/z 520 [M+H]$^+$.

Example 3b (2R)-4-Methyl-2-({2-oxo-5-[(1-pyridin-2-ylethyl)sulfanyl]-2,3-dihydro[1,3]thiazolo[4,5-d]pyrimidin-7-yl}amino)pentyl dihydrogen phosphate

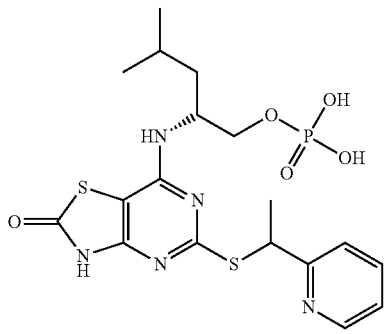

The title compound was synthesized from 7-{[(1R)-1-(hydroxymethyl)-3-methylbutyl]amino}-5-{[1-pyridin-2-ylethyl]sulfanyl}[1,3]thiazolo[4,5-d]pyrimidin-2(3H)-one (Karlström S., et al., *J. Med. Chem.*, 2013, 56, 3177-3190; WO2008/039138) in 2% yield using the method described for Example 3. The product is a mixture of two diastereomers. $^1$H NMR (600 MHz, DMSO-d$_6$) $\delta_H$ ppm 12.36 (br. s., 2H) 8.52 (ddd, J=1.97, 0.97 Hz, 1H) 8.52 (ddd, J=1.87, 0.97 Hz, 1H) 7.76 (ddd, J=7.80, 7.59, 1.87 Hz, 1H) 7.75 (ddd, J=7.80, 7.59, 1.87 Hz, 1H) 7.53 (dt, J=7.80, 0.97 Hz, 1H) 7.50 (dt, J=7.80, 0.97 Hz, 1H) 7.27 (ddd, J=7.59, 4.87, 0.97 Hz, 1H) 7.25 (ddd, J=7.59, 4.87, 0.97 Hz, 1H) 7.11 (br. s., 1H) 5.11 (q, J=7.07 Hz, 1H) 5.06 (q, J=7.07 Hz, 1H) 4.37-4.51 (m, 1H) 4.16-4.30 (m, 1H) 3.73-3.85 (m, 3H) 3.67-3.73 (m, 1H) 1.67 (d, J=7.07 Hz, 3H) 1.66 (d, J=7.07 Hz, 3H) 1.54-1.64 (m, 2H) 1.45-1.54 (m, 2H) 1.34-1.45 (m, 2H) 0.89 (d, J=6.56 Hz, 3H) 0.87 (d, J=6.71 Hz, 3H) 0.86 (d, J=6.56 Hz, 3H) 0.78 (d, J=6.26 Hz, 3H). MS (ESI$^+$) m/z 486 [M+H]$^+$.

Example 3c (2R)-4-Methyl-2-{[5-({1-[4-(methylsulfonyl)phenyl]ethyl}sulfanyl)-2-oxo-2,3-dihydro[1,3]thiazolo[4,5-d]pyrimidin-7-yl]amino}pentyl dihydrogen phosphate

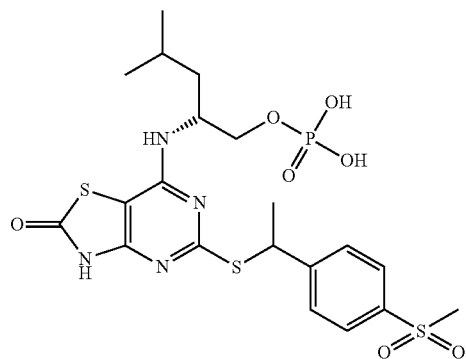

The title compound was synthesized from 7-{[(1R)-1-(hydroxymethyl)-3-methylbutyl]amino}-5-({1-[4-(methylsulfonyl)phenyl]ethyl}sulfanyl)[1,3]thiazolo[4,5-d]pyrimidin-2(3H)-one (Karlström S., et al., *J. Med. Chem.*, 2013, 56, 3177-3190; WO2008/039138) as a single diastereomer, in 43% yield using the method described for Example 3. The product is single diastereomer. $^1$H NMR (600 MHz, DMSO-d$_6$) $\delta_H$ ppm 8.41 (br. s., 1H) 7.83-7.87 (m, 2H) 7.73-7.77 (m, 2H) 7.30 (br. s., 2H) 5.04 (q, J=7.18 Hz, 1H) 4.07-4.16 (m, 1H) 3.67-3.77 (m, 2H) 3.19 (s, 3H) 1.67 (d, J=7.18 Hz, 3H) 1.51-1.60 (m, 1H) 1.47 (ddd, J=13.50, 8.30, 6.70 Hz, 1H) 1.37-1.44 (m, 1H) 0.85 (d, J=6.56 Hz, 3H) 0.77 (d, J=6.26 Hz, 3H). MS (ESI$^+$) m/z 563 [M+H]$^+$.

Example 3d (2R)-2-[(5-{[1-(3-Carbamoylphenyl)ethyl]sulfanyl}-2-oxo-2,3-dihydro[1,3]thiazolo[4,5-d]pyrimidin-7-yl)amino]-4-methylpentyl dihydrogen phosphate

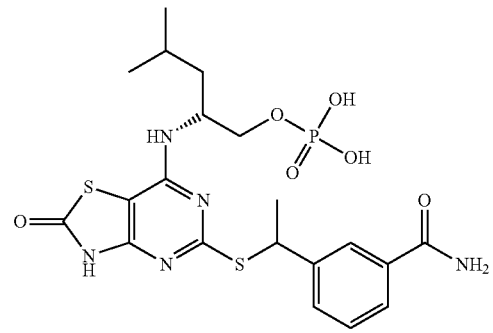

The title compound was synthesized from 3-{1-[(7-{[(1R)-1-(hydroxymethyl)-3-methylbutyl]amino}-2-oxo-2,3- dihydro[1,3]thiazolo[4,5-d]pyrimidin-5-yl)sulfanyl]
ethyl}benzamide (Karlström S., et al., *J. Med. Chem.*, 2013,
56, 3177-3190; WO2008/039138) as a single diastereomer,
in 20% yield using the method described for Example 3. The
product is single diastereomer. $^1$H NMR (600 MHz, DMSO-
$d_6$) $\delta_H$ ppm 8.33 (br. s., 1H) 8.46 (br. s., 1H) 8.06 (br. s., 1H)
7.76 (ddd, J=7.70, 1.68, 1.22 Hz, 1H) 7.58 (ddd, J=7.70,
1.51, 1.22 Hz, 1H) 7.41 (t, J=7.70 Hz, 1H) 7.30 (br. s., 1H)
7.23 (br. s., 3H) 5.07 (q, J=7.04 Hz, 1H) 4.25-4.42 (m, 1H)
3.74 (td, J=10.15, 4.82 Hz, 1H) 3.65-3.71 (m, 1H) 1.70 (d,
J=7.04 Hz, 3H) 1.57-1.66 (m, 1H) 1.40-1.51 (m, 2H) 0.89 (d,
J=6.56 Hz, 3H) 0.85 (d, J=6.56 Hz, 1H). MS (ESI$^+$) m/z 528
[M+H]$^+$.

Example 3e (2R)-2-[(5-{[1-(2-Chlorophenyl)ethyl]sulfanyl}-2-
oxo-2,3-dihydro[1,3]thiazolo[4,5-d]pyrimidin-7-yl)
amino]-4-methylpentyl dihydrogen phosphate

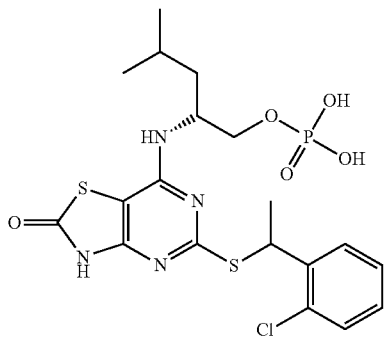

The title compound was synthesized from 5-{[1-(2-chlo-
rophenyl)ethyl]sulfanyl}-7-{[(1R)-1-(hydroxymethyl)-3-
methylbutyl]amino}[1,3]thiazolo[4,5-d]pyrimidin-2(3H)-
one (Karlström S., et al., *J. Med. Chem.*, 2013, 56, 3177-
3190; WO2008/039138) in 49% yield using the method
described for Example 3. The two diastereomers were
separated by preparatory HPLC (basic method).

Diastereomer A: $^1$H NMR (600 MHz, DMSO-$d_6$) $\delta_H$ ppm
8.43 (br. s., 2H) 7.61 (dd, J=7.75, 1.65 Hz, 1H) 7.47 (dd,
J=7.88, 1.30 Hz, 1H) 7.36 (ddd, J=7.75, 7.40, 1.60 Hz, 1H)
7.29 (ddd, J=7.88, 7.40, 1.65 Hz, 1H) 6.57-8.60 (m, 3H) 5.34
(q, J=6.93 Hz, 1H) 4.17-4.27 (m, 1H) 3.77-3.83 (m, 1H) 3.70
(td, J=10.07, 3.66 Hz, 1H) 1.74 (d, J=6.93 Hz, 3H) 1.57-1.65
(m, 1H) 1.49-1.61 (m, 1H) 1.38-1.46 (m, 1H) 0.86 (d, J=7.00
Hz, 3H) 0.82 (d, J=6.16 Hz, 3H). MS (ESI$^+$) m/z 519
[M+H]$^+$.

Diastereomer B: $^1$H NMR (600 MHz, DMSO-$d_6$) $\delta_H$ ppm
8.90 (br. s., 1H) 7.60 (dd, J=7.82, 1.72 Hz, 1H) 7.46 (dd,
J=7.96, 1.30 Hz, 1H) 7.36 (ddd, J=7.82, 7.50, 1.30 Hz, 1H)
7.30 (ddd, J=7.96, 7.50, 1.72 Hz, 1H) 6.46-8.26 (m, 3H) 5.42
(q, J=6.99 Hz, 1H) 4.15-4.25 (m, 1H) 3.70-3.76 (m, 1H) 3.66
(td, J=11.41, 4.35 Hz, 1H) 1.69 (d, J=6.99 Hz, 3H) 1.56-1.65
(m, 1H) 1.52 (dt, J=13.28, 7.48 Hz, 1H) 1.43 (dt, J=13.28,
7.02 Hz, 1H) 0.89 (d, J=6.71 Hz, 3H) 0.87 (d, J=6.56 Hz,
3H). MS (ESI$^+$) m/z 519 [M+H]$^+$.

Example 3f (2R)-2-[(5-{[1-(3-Cyanophenyl)ethyl]sulfanyl}-2-
oxo-2,3-dihydro[1,3]thiazolo[4,5-d]pyrimidin-7-yl)
amino]-4-methylpentyl dihydrogen phosphate

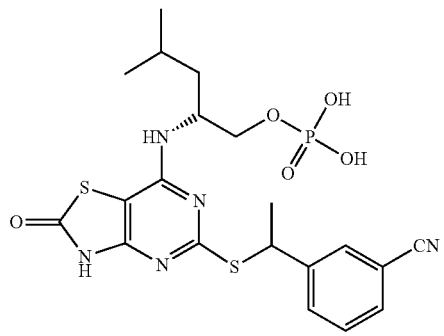

The title compound was synthesized from 3-{1-[(7-{
[(1R)-1-(hydroxymethyl)-3-methylbutyl]amino}-2-oxo-2,3-
dihydro[1,3]thiazolo[4,5-d]pyrimidin-5-yl)sulfanyl]
ethyl}benzonitrile (Karlström S., et al., *J. Med. Chem.*,
2013, 56, 3177-3190; WO2008/039138) in 49% yield using
the method described for Example 3. The two diastereomers
were separated by preparatory HPLC (basic method).

Diastereomer A: $^1$H NMR (600 MHz, DMSO-$d_6$) $\delta_H$ ppm
7.93 (dd, J=1.80, 1.36 Hz, 1H) 7.83 (ddd, J=7.95, 1.80, 1.36
Hz, 1H) 7.68 (dt, J=7.68, 1.36 Hz, 1H) 7.51 (dd, J=7.95, 7.68
Hz, 1H) 7.44 (br. s., 4H) 5.00 (q, J=7.15 Hz, 1H) 4.05-4.13
(m, 1H) 3.61-3.71 (m, 2H) 1.65 (d, J=7.15 Hz, 3H) 1.52-1.62
(m, 1H) 1.36-1.48 (m, 2H) 0.85 (d, J=6.58 Hz, 3H) 0.78 (d,
J=6.58 Hz, 3H). MS (ESI$^+$) m/z 510 [M+H]$^+$.

Diastereomer B: $^1$H NMR (600 MHz, DMSO-$d_6$) $\delta_H$ ppm
8.55 (br. s., 1H) 7.94 (dd, J=1.80, 1.36 Hz, 1H) 7.83 (ddd,
J=7.95, 1.80, 1.36 Hz, 1H) 7.69 (dt, J=7.68, 1.36 Hz, 1H)
7.56 (dd, J=7.95, 7.68 Hz, 1H) 7.37 (br. s., 3H) 5.00 (q,
J=7.19 Hz, 1H) 4.15-4.24 (m, 1H) 3.63-3.73 (m, 2H) 1.67 (d,
J=7.19 Hz, 3H) 1.54-1.63 (m, 1H) 1.39-1.48 (m, 2H) 0.89 (d,
J=6.56 Hz, 3H) 0.86 (d, J=6.56 Hz, 3H). MS (ESI$^+$) m/z 510
[M+H]$^+$.

Example 3g (2R)-2-[(5-{[(1S)-1-(5-Chloropyridin-2-yl)ethyl]
sulfanyl}-2-oxo-2,3-dihydro[1,3]thiazolo[4,5-d]py-
rimidin-7-yl)amino]-4-methylpentyl dimethyl phos-
phate

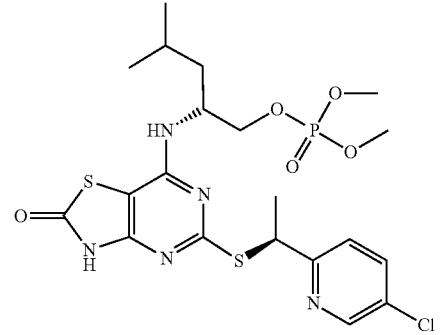

The title compound was synthesized from 5-{[(1S)-1-(5-chloropyridin-2-yl)ethyl]sulfanyl}-7-{[(1R)-1-(hydroxymethyl)-3-methylbutyl]amino}[1,3]thiazolo[4,5-d]pyrimidin-2(3H)-one (Karlström S., et al., *J. Med. Chem.*, 2013, 56, 3177-3190; WO2008/039138) in 27% yield using the method described for Example 3 with the exception that MeOH, instead of water, was added after 2 h at ice-bath temperature. $^1$H NMR (600 MHz, DMSO-d$_6$) $\delta_H$ ppm 8.48 (d, J=2.4 Hz, 1H) 7.79 (d, J=7.9 Hz, 1H) 7.61 (d, J=8.2 Hz, 1H) 5.09 (q, J=7.3 Hz, 1H) 4.63 (br. s., 1H) 3.89-3.97 (m, 2H) 3.70 (d, J=11.3 Hz, 3H) 3.67 (d, J=11.3 Hz, 3H) 1.69 (d, 3H) 1.64-1.73 (m, 1H) 1.58 (ddd, J=14.0, 10.5, 4.9 Hz, 1H) 1.38 (ddd, J=13.8, 9.4, 4.3 Hz, 1H) 0.96 (d, J=6.7 Hz, 3H) 0.94 (d, J=6.7 Hz, 3H). MS (ESI$^+$) m/z 548 [M+H]$^+$.

Example 3h (2R)-2-[(5-{[(1S)-1-(5-Chloropyridin-2-yl)ethyl]sulfanyl}-2-oxo-2,3-dihydro[1,3]thiazolo[4,5-d]pyrimidin-7-yl)amino]-4-methylpentyl diethyl phosphate

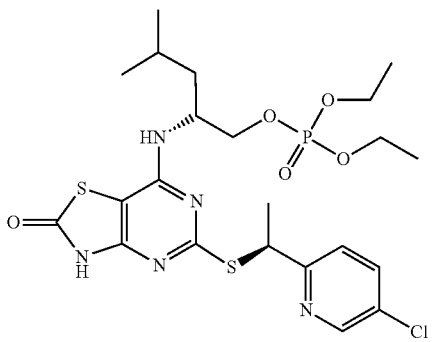

The title compound was synthesized from 5-{[(1S)-1-(5-chloropyridin-2-yl)ethyl]sulfanyl}-7-{[(1R)-1-(hydroxymethyl)-3-methylbutyl]amino}[1,3]thiazolo[4,5-d]pyrimidin-2(3H)-one (Karlström S., et al., *J. Med. Chem.*, 2013, 56, 3177-3190; WO2008/039138) in 20% yield using the method described for Example 3 with the exception that 2-methyl-THF was used as solvent and that EtOH, instead of water, was added after 2 h at ice-bath temperature. $^1$H NMR (600 MHz, DMSO-d$_6$) $\delta_H$ ppm 8.47 (d, J=1.2 Hz, 1H) 7.78 (d, J=7.0 Hz, 1H) 7.61 (d, J=7.0 Hz, 1H) 5.09 (q, J=7.0 Hz, 1H) 4.63 (br. s., 1H) 3.96-4.14 (m, 4H) 3.89-3.95 (m, 2H) 1.68 (d, J=7.0 Hz, 3H) 1.63-1.67 (m, 1H) 1.58 (ddd, J=13.8, 10.6, 4.9 Hz, 1H) 1.35-1.40 (m, 1H) 1.26 (td, J=7.2, 0.9 Hz, 3H) 1.20 (td, J=7.0, 0.9 Hz, 3H) 0.96 (d, J=6.4 Hz, 3H) 0.94 (d, J=6.4 Hz, 3H). MS (ESI$^+$) m/z 576 [M+H]$^+$.

Example 4

(7-{[(1R)-1-(Hydroxymethyl)-3-methylbutyl]amino}-5-{[(1S)-1-phenylethyl]sulfanyl}[1,3]thiazolo[4,5-d]pyrimidin-2-yl)phosphoramidic acid

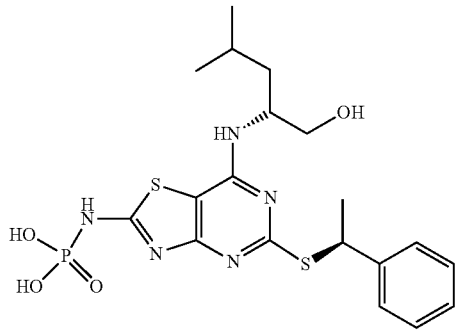

The title product was synthesized from (2R)-2-[(2-amino-5-{[(1S)-1-phenylethyl]sulfanyl}-[1,3]thiazolo[4,5-d]pyrimidin-7-yl)amino]-4-methylpentan-1-ol hydrochloride (Karlström S., et al., *J. Med. Chem.*, 2013, 56, 3177-3190; WO 2006/107258) in two steps.

Step 1: N$^7$-[(1R)-1-({[tert-Butyl(dimethyl)silyl]oxy}methyl)-3-methylbutyl]-5-{[(1S)-1-phenylethyl]sulfanyl}[1,3]thiazolo[4,5-d]pyrimidine-2,7-diamine To a solution of (2R)-2-[(2-amino-5-{[(1S)-1-phenylethyl]sulfanyl}-[1,3]thiazolo[4,5-d]pyrimidin-7-yl)amino]-4-methylpentan-1-ol hydrochloride[1,2] (605 mg, 1.50 mmol), tert-butyldimethylsilyl chloride (520 mg, 3.46 mmol) and DMAP (92 mg, 0.75 mmol) in DCM (5 mL) was added Et$_3$N (630 µL, 5.50 mmol). The reaction mixture was stirred at room temperature for 1.5 h. DCM (25 mL) was added and the resulting organic phase was washed with 2M citric acid (2×5 mL) and water (5 mL), dried over Na$_2$SO$_4$, filtered and evaporated to yield 969 mg of crude material. The crude product was purified by flash chromatography (silica, 3-4% MeOH in DCM) and the pure fractions were pooled and evaporated to yield 741 mg (95%) of >99% pure product as a white solid.

$^1$H NMR (600 MHz, CD$_3$OD) $\delta_H$ ppm 7.44 (dd, J=8.2, 0.9 Hz, 2H) 7.28-7.32 (m, 2H) 7.19-7.24 (m, 1H) 5.07 (q, J=7.2 Hz, 1H) 4.51 (br. s., 1H) 3.59 (dd, J=10.1, 5.5 Hz, 1H) 3.50 (dd, J=9.9, 6.0 Hz, 1H) 1.74 (d, J=7.0 Hz, 3H) 1.70-1.79 (m, 1H) 1.49-1.55 (m, 1H) 1.43-1.49 (m, 1H) 0.97 (d, J=6.7 Hz, 3H) 0.95 (d, J=6.4 Hz, 3H) 0.84 (s, 9H) 0.03 (s, 3H) 0.01 (s, 3H). MS (ESI$^+$) m/z 518 [M+H]$^+$.

Step 2:

N$^7$-[(1R)-1-({[tert-Butyl(dimethyl)silyl]oxy}methyl)-3-methylbutyl]-5-{[(1S)-1-phenylethyl]sulfanyl}[1,3]thiazolo[4,5-d]pyrimidine-2,7-diamine (115 mg, 0.22 mmol) in DCM (1.5 mL) was added to a mixture of phosphorous pentachloride (92 mg, 0.44 mmol) and pyridine (53 mg, 0.67 mmol) in DCM (0.5 mL) at ice-bath temperature. The reaction mixture was stirred at ice-bath temperature for 60 min. Water (1 mL) and DMSO (1 mL) were added and the reaction was stirred at 50° C. for 1.5 h. The reaction mixture was filtered through an Agilent 0.45 µm nylon disc filter and the crude mixture was purified by preparatory HPLC (basic method) to yield 49 mg (43%) of pure title product as a white solid. The product was assumed to be the diammonium salt after purification. $^1$H NMR (600 MHz, CD$_3$OD) $\delta_H$ ppm 7.44-7.48 (m, 2H) 7.27-7.33 (m, 2H) 7.21 (tt, J=7.3, 1.2 Hz, 1H) 5.09 (q, J=7.0 Hz, 1H) 4.51 (br. s., 1H) 3.57 (dd, J=11.0, 5.2 Hz, 1H) 3.49 (dd, J=11.1, 5.6 Hz, 1H) 1.73 (d, J=7.0 Hz, 3H) 1.70-1.78 (m, 1H) 1.54-1.61 (m, 1H) 1.46-1.53 (m, 1H) 0.97 (d, J=6.7 Hz, 3H) 0.95 (d, J=6.7 Hz, 3H). MS (ESI$^+$) m/z 484 [M+H]$^+$.

Example 4b (5-{[1-(2-Chlorophenyl)ethyl]sulfanyl}-7-{[(1R)-1-(hydroxymethyl)-3-methylbutyl]amino}[1,3]thiazolo[4,5-d]pyrimidin-2-yl)phosphoramidic acid

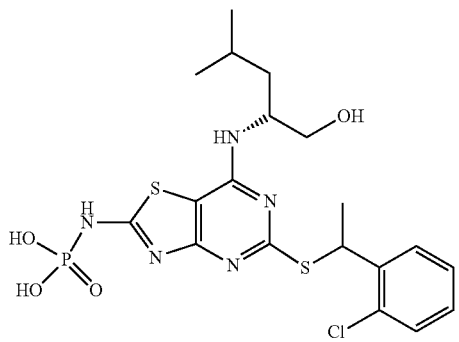

The title product was synthesized from (2R)-2-[(2-amino-5-{[1-(2-chlorophenyl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in two steps, using the method described for Example 4. Overall yield for two steps: 62%.

Step 1: N$^7$-[(1R)-1-({[tert-Butyl(dimethyl)silyl]oxy}methyl)-3-methylbutyl]-5-{[1-(2-chlorophenyl)ethyl]sulfanyl}[1,3]thiazolo[4,5-d]pyrimidine-2,7-diamine The product is a mixture of two diastereomers. $^1$H NMR (600 MHz, CD$_3$OD) δ$_H$ ppm 7.67 (dd, J=7.8, 1.7 Hz, 1H) 7.64 (dd, J=7.8, 1.7 Hz, 1H) 7.39 (dd, J=7.8, 1.2 Hz, 1H) 7.39 (dd, J=7.8, 1.2 Hz, 1H) 7.29 (td, J=7.6, 1.2 Hz, 2H) 7.22 (tt, J=7.7, 1.5 Hz, 2H) 5.52 (q, J=7.0 Hz, 1H) 5.50 (q, J=7.0 Hz, 1H) 4.51 (br. s., 2H) 3.67 (dd, J=10.1, 5.5 Hz, 1H) 3.63 (dd, J=9.8, 5.8 Hz, 1H) 3.49 (dd, J=10.1, 4.3 Hz, 1H) 3.37 (dd, J=10.1, 4.9 Hz, 1H) 1.73 (d, J=7.0 Hz, 3H) 1.68 (d, J=7.0 Hz, 3H) 1.64-1.76 (m, 2H) 1.56-1.62 (m, 1H) 1.49-1.55 (m, 1H) 1.41 (dddd, J=13.7, 9.3, 4.2, 2.4 Hz, 2H) 0.97 (d, J=6.7 Hz, 3H) 0.96 (d, J=6.7 Hz, 3H) 0.92 (d, J=6.7 Hz, 3H) 0.84 (s, 9H) 0.81 (s, 9H) 0.03 (s, 3H) 0.00 (s, 3H) −0.06 (s, 3H) −0.07 (s, 3H). MS (ESI$^+$) m/z 552 [M+H]$^+$.

Step 2: The two diastereomers were separated by preparatory HPLC (basic method).

Diastereomer A: $^1$H NMR (600 MHz, CD$_3$OD) δ$_H$ ppm 7.66 (dd, J=7.8, 1.7 Hz, 1H) 7.42 (dd, J=7.9, 1.2 Hz, 1H) 7.31 (td, J=7.6, 1.4 Hz, 1H) 7.25 (td, J=7.7, 1.7 Hz, 1H) 5.57 (q, J=7.0 Hz, 1H) 4.54 (br. s., 1H) 3.49 (dd, J=11.3, 4.3 Hz, 1H) 3.40 (dd, J=11.1, 4.7 Hz, 1H) 1.72 (d, J=7.0 Hz, 3H) 1.60-1.78 (m, 2H) 1.44 (ddd, J=13.7, 9.2, 4.6 Hz, 1H) 0.98 (d, J=6.7 Hz, 3H) 0.96 (d, J=6.7 Hz, 3H). MS (ESI$^+$) m/z 518 [M+H]$^+$.

Diastereomer B: $^1$H NMR (600 MHz, CD$_3$OD) 7.65 (dd, J=7.8, 1.7 Hz, 1H) 7.39 (dd, J=7.9, 1.5 Hz, 1H) 7.29 (td, J=7.3, 1.2 Hz, 1H) 7.22 (td, J=7.7, 1.5 Hz, 1H) 5.53 (q, J=7.0 Hz, 1H) 4.46 (br. s., 1H) 3.67 (dd, J=11.0, 5.2 Hz, 1H) 3.60 (dd, J=11.3, 4.9 Hz, 1H) 1.74 (d, J=7.0 Hz, 3H) 1.56-1.73 (m, 2H) 1.37-1.42 (m, 1H) 0.92 (d, J=6.7 Hz, 3H) 0.82 (d, J=6.7 Hz, 3H). MS (ESI$^+$) m/z 518 [M+H]$^+$.

Example 4c (7-{[(1R)-1-(Hydroxymethyl)-3-methylbutyl]amino}-5-[(1-pyridin-2-ylethyl)sulfanyl][1,3]thiazolo[4,5-d]pyrimidin-2-yl)phosphoramidic acid

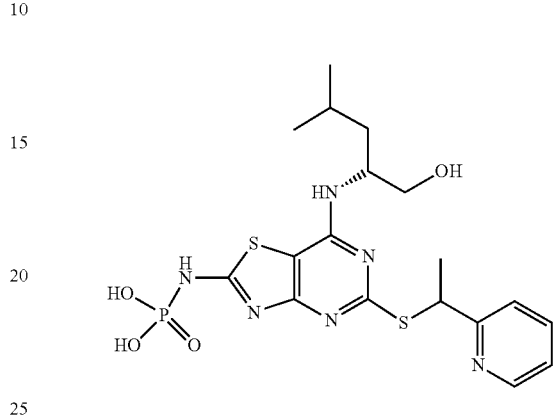

The title product was synthesized from (2R)-2-({2-amino-5-[(1-pyridin-2-ylethyl) sulfanyl][1,3]thiazolo[4,5-d]pyrimidin-7-yl}amino)-4-methylpentan-1-ol (Karlström S., et al., *J. Med. Chem.*, 2013, 56, 3177-3190; WO 2006/107258) in two steps, using the method described for Example 4. Overall yield for two steps: 29%.

Step 1: N$^7$-[(1R)-1-({[tert-Butyl(dimethyl)silyl]oxy}methyl)-3-methylbutyl]-5-[(1-pyridin-2-ylethyl)sulfanyl][1,3]thiazolo[4,5-d]pyrimidine-2,7-diamine The product is a mixture of two diastereomers. $^1$H NMR (600 MHz, CD$_3$OD) δ$_H$ ppm 8.45-8.50 (m, 2H) 7.77 (td, J=7.9, 1.8 Hz, 1H) 7.76 (td, J=7.7, 1.8 Hz, 1H) 7.60 (d, J=7.9 Hz, 2H) 7.28 (dt, J=4.9, 1.2 Hz, 1H) 7.27 (dt, J=4.9, 1.2 Hz, 1H) 5.19 (q, J=7.2 Hz, 1H) 5.18 (q, J=7.2 Hz, 1H) 4.42 (br. s., 2H) 3.60-3.67 (m, 2H) 3.54 (dd, J=10.1, 5.2 Hz, 1H) 3.44 (dd, J=9.9, 5.6 Hz, 1H) 1.76 (d, J=7.0 Hz, 3H) 1.74 (d, J=7.0 Hz, 3H) 1.66-1.73 (m, 2H) 1.47-1.55 (m, 2H) 1.39-1.46 (m, 2H) 0.96 (d, J=6.7 Hz, 3H) 0.95 (d, J=6.7 Hz, 3H) 0.94 (d, J=6.7 Hz, 3H) 0.86 (d, J=6.4 Hz, 3H) 0.83 (s, 18H) 0.02 (s, 3H) 0.01 (s, 3H) 0.00 (s, 3H) −0.01 (s, 3H). MS (ESI$^+$) m/z 519 [M+H]$^+$.

Step 2: The two diastereomers were separated by preparatory HPLC (basic method).

Diastereomer A: $^1$H NMR (600 MHz, CD$_3$OD) δ$_H$ ppm 8.47 (dt, J=5.0, 0.9 Hz, 1H) 7.78 (td, J=7.7, 1.7 Hz, 1H) 7.64 (dt, J=7.9, 1.0 Hz, 1H) 7.28 (ddd, J=7.3, 4.9, 0.9 Hz, 1H) 5.24 (q, J=7.3 Hz, 1H) 4.50 (br. s., 1H) 3.52 (dd, J=11.0, 5.5 Hz, 1H) 3.42 (dd, J=11.1, 5.6 Hz, 1H) 1.75 (d, J=7.0 Hz, 3H) 1.68-1.73 (m, 1H) 1.51-1.60 (m, 1H) 1.43-1.51 (m, 1H) 0.97 (d, J=6.7 Hz, 3H) 0.95 (d, J=6.7 Hz, 3H). MS (ESI$^+$) m/z 485 [M+H]$^+$.

Diastereomer B: $^1$H NMR (600 MHz, CD$_3$OD) δ$_H$ ppm 8.47 (dt, J=5.0, 0.9 Hz, 1H) 7.78 (td, J=7.8, 1.8 Hz, 1H) 7.66 (d, J=7.9 Hz, 1H) 7.26-7.29 (m, 1H) 5.17 (q, J=7.2 Hz, 1H) 4.24 (br. s., 1H) 3.65 (dd, J=11.0, 4.9 Hz, 1H) 3.52 (dd, J=11.0, 6.1 Hz, 1H) 1.73 (d, J=7.3 Hz, 3H) 1.60-1.67 (m, 1H) 1.51-1.59 (m, 1H) 1.43-1.51 (m, 1H) 0.91 (d, J=6.4 Hz, 3H) 0.77 (d, J=6.4 Hz, 3H). MS (ESI$^+$) m/z 485 [M+H]$^+$.

Example 4d (5-{1-(3-Cyanophenyl)ethyl]sulfanyl}-7-{[(1R)-1-(hydroxymethyl)-3-methylbutyl]amino}[1,3]thiazolo[4,5-d]pyrimidin-2-yl)phosphoramidic acid

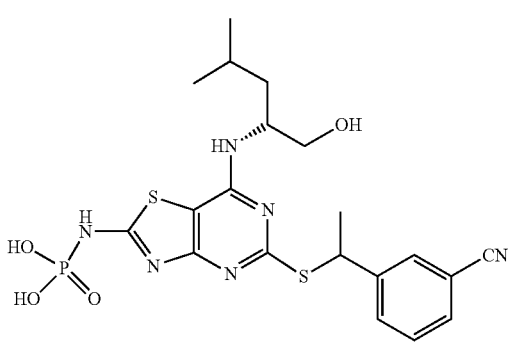

The title compound was synthesized from 3-{1-[(2-amino-7-{[(1R)-1-(hydroxymethyl)-3-methylbutyl]amino}[1,3]thiazolo[4,5-d]pyrimidin-5-yl)sulfanyl]ethyl}benzonitrile (Karlström S., et al., *J. Med. Chem.*, 2013, 56, 3177-3190; WO 2006/107258) in two steps, using the method described for Example 4. Overall yield for two steps: 47%.

Step 1: 3-{1-[(2-Amino-7-{[(1R)-1-({[tert-butyl(dimethyl)silyl]oxy}methyl)-3-methylbutyl]amino}[1,3]thiazolo[4,5-d]pyrimidin-5-yl)sulfanyl]ethyl}benzonitrile The product is a mixture of two diastereomers. $^1$H NMR (600 MHz, CD$_3$OD) $\delta_H$ ppm 7.80-7.88 (m, 4H) 7.59 (dt, J=6.1, 1.2 Hz, 1H) 7.58 (dt, J=6.1, 1.2 Hz, 1H) 7.49 (q, J=7.5 Hz, 2H) 5.10 (q, J=7.3 Hz, 2H) 4.44 (br. s., 1H) 4.35 (br. s., 1H) 3.68 (dd, J=9.8, 5.8 Hz, 1H) 3.58 (dd, J=9.8, 6.1 Hz, 1H) 3.54 (dd, J=9.9, 5.3 Hz, 1H) 3.43-3.48 (m, 1H) 1.71 (d, J=7.3 Hz, 3H) 1.70 (d, J=7.3 Hz, 3H) 1.63-1.75 (m, 2H) 1.39-1.55 (m, 4H) 0.97 (d, J=6.7 Hz, 3H) 0.96 (d, J=6.7 Hz, 3H) 0.93 (d, J=6.7 Hz, 3H) 0.85 (s, 9H) 0.81 (s, 9H) 0.81 (d, J=6.4 Hz, 3H) 0.05 (s, 3H) 0.03 (s, 3H) 0.00 (s, 3H) −0.02 (s, 3H). MS (ESI$^+$) m/z 543 [M+H]$^+$.

Step 2: The two diastereomers were separated by preparatory HPLC (basic method).

Diastereomer A: $^1$H NMR (600 MHz, CD$_3$OD) $\delta_H$ ppm 7.87 (s, 1H) 7.85 (dd, J=7.8, 1.1 Hz, 1H) 7.57 (dd, J=7.6, 1.5 Hz, 1H) 7.49 (t, J=7.8 Hz, 1H) 5.13 (q, J=7.2 Hz, 1H) 4.29 (br. s., 1H) 3.63 (dd, J=11.0, 5.2 Hz, 1H) 3.55 (dd, J=10.7, 5.8 Hz, 1H) 1.70 (d, J=7.3 Hz, 3H) 1.61-1.68 (m, 1H) 1.49-1.57 (m, 1H) 1.41-1.48 (m, 1H) 0.92 (d, J=6.7 Hz, 3H) 0.80 (d, J=6.7 Hz, 3H). MS (ESI$^+$) m/z 509 [M+H]$^+$.

Diastereomer B: $^1$H NMR (600 MHz, CD$_3$OD) $\delta_H$ ppm 7.86 (s, 1H) 7.84 (dd, J=7.9, 1.5 Hz, 1H) 7.58 (d, J=7.9 Hz, 1H) 7.49 (t, J=7.8 Hz, 1H) 5.12 (q, J=7.0 Hz, 1H) 4.44 (br. s., 1H) 3.53 (dd, J=11.0, 5.2 Hz, 1H) 3.43 (dd, J=11.0, 5.5 Hz, 1H) 1.71 (d, J=7.3 Hz, 3H) 1.67-1.74 (m, 1H) 1.51-1.60 (m, 1H) 1.43-1.51 (m, 1H) 0.97 (d, J=6.7 Hz, 3H) 0.95 (d, 3H). MS (ESI$^+$) m/z 509 [M+H]$^+$.

Example 4e (5-{[1-(3-Fluoropyridin-2-yl)ethyl]sulfanyl}-7-{[(1R)-1-(hydroxymethyl)-3-methylbutyl]amino}[1,3]thiazolo[4,5-d]pyrimidin-2-yl)phosphoramidic acid

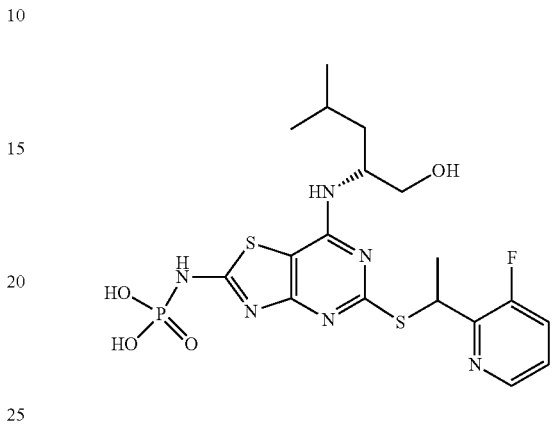

The title compound was synthesized from (2R)-2-[(2-amino-5-{[1-(3-fluoropyridin-2-yl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in two steps, using the method described for Example 4. Overall yield for two steps: 55%.

Step 1: N$^7$-[(1R)-1-({[tert-Butyl(dimethyl)silyl]oxy}methyl)-3-methylbutyl]-5-{[1-(3-fluoropyridin-2-yl)ethyl]sulfanyl}[1,3]thiazolo[4,5-d]pyrimidine-2,7-diamine The product is a mixture of two diastereomers. $^1$H NMR (600 MHz, CD$_3$OD) $\delta_H$ ppm 8.35 (d, J=1.2 Hz, 1H) 8.34 (d, J=0.9 Hz, 1H) 7.59 (dt, J=8.5, 1.2 Hz, 1H) 7.57 (dt, J=8.2, 1.2 Hz, 1H) 7.34-7.39 (m, 2H) 5.59 (q, J=7.0 Hz, 2H) 4.54 (br. s., 2H) 3.65 (d, J=5.8 Hz, 2H) 3.62 (dd, J=10.1, 5.5 Hz, 1H) 3.57 (dd, J=10.1, 5.8 Hz, 1H) 1.79 (d, J=7.0 Hz, 3H) 1.77 (d, J=7.0 Hz, 3H) 1.70-1.76 (m, 2H) 1.50-1.57 (m, 2H) 1.42-1.50 (m, 2H) 0.98 (d, J=6.7 Hz, 3H) 0.96 (d, J=6.7 Hz, 3H) 0.96 (d, J=6.4 Hz, 3H) 0.93 (d, J=6.4 Hz, 3H) 0.83 (s, 9H) 0.82 (s, 9H) 0.03 (s, 3H) 0.02 (s, 3H) 0.00 (s, 3H) −0.01 (s, 3H). MS (ESI$^+$) m/z 537 [M+H]$^+$.

Step 2: The two diastereomers were separated by preparatory HPLC (basic method).

Diastereomer A: $^1$H NMR (600 MHz, CD$_3$OD) $\delta_H$ ppm 8.33 (dd, J=4.9, 1.5 Hz, 1H) 7.59 (t, J=9.4 Hz, 1H) 7.34-7.38 (m, 1H) 5.62 (q, J=7.1 Hz, 1H) 4.53 (br. s., 1H) 3.59 (dd, J=11.0, 4.9 Hz, 1H) 3.54 (d, J=11.0, 4.9 Hz, 1H) 1.77 (d, J=7.3 Hz, 3H) 1.70-1.75 (m, 1H) 1.55-1.64 (m, 1H) 1.45-1.52 (m, 1H) 0.98 (d, J=6.4 Hz, 3H) 0.96 (d, J=6.4 Hz, 3H). MS (ESI$^+$) m/z 503 [M+H]$^+$.

Diastereomer B: $^1$H NMR (600 MHz, CD$_3$OD) $\delta_H$ ppm 8.34 (dt, J=4.9, 1.2 Hz, 1H) 7.58 (ddd, J=9.8, 8.4, 1.2 Hz, 1H) 7.34-7.38 (m, 1H) 5.60 (q, J=7.0 Hz, 1H) 4.49 (br. s., 1H) 3.63 (dd, J=5.2, 1.5 Hz, 2H) 1.79 (d, J=7.0 Hz, 3H) 1.70-1.75 (m, 1H) 1.55-1.64 (m, 1H) 1.44-1.52 (m, 1H) 0.97 (d, J=7.0 Hz, 3H) 0.91 (d, J=6.7 Hz, 3H). MS (ESI$^+$) m/z 503 [M+H]$^+$.

Example 4f

Diethyl (7-{[(1R)-1-(hydroxymethyl)-3-methylbutyl]amino}-5-{[(1S)-1-phenylethyl]sulfanyl}[1,3]thiazolo[4,5-d]pyrimidin-2-yl)amidophosphate

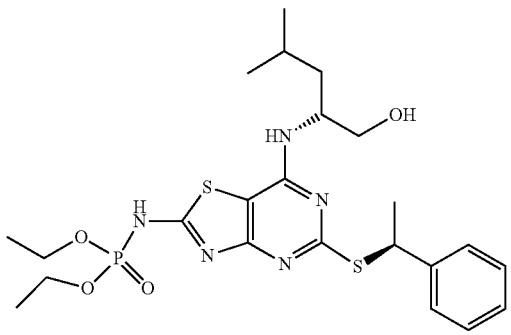

The title product was synthesized from (2R)-2-[(2-amino-5-{[(1S)-1-phenylethyl]sulfanyl}-[1,3]thiazolo[4,5-d]pyrimidin-7-yl)amino]-4-methylpentan-1-ol hydrochloride (Karlström S., et al., *J. Med. Chem.*, 2013, 56, 3177-3190; WO 2006/107258) in two steps, using the method described for Example 4 with the exception that EtOH, instead of water and DMSO, was added after 1 h at ice-bath temperature in step 2.

The starting material for step 2 was the same as in Example 4. Overall yield for two steps: 71%.

Step 2: $^1$H NMR (600 MHz, CD$_3$OD) $\delta_H$ ppm 7.44-7.47 (m, 2H) 7.29-7.34 (m, 2H) 7.22 (tt, J=7.3, 1.5 Hz, 1H) 5.05 (q, J=7.0 Hz, 1H) 4.51 (br. s., 1H) 4.08-4.17 (m, 4H) 3.55 (dd, J=11.0, 5.2 Hz, 1H) 3.49 (dd, J=11.0, 5.5 Hz, 1H) 1.73 (d, J=7.0 Hz, 3H) 1.67-1.72 (m, 1H) 1.53-1.59 (m, 1H) 1.44-1.50 (m, 1H) 1.34 (tdd, J=7.0, 2.1, 0.61 Hz, 6H) 0.97 (d, J=6.7 Hz, 3H) 0.95 (d, J=6.7 Hz, 3H). MS (ESI$^+$) m/z 540 [M+H]$^+$.

Example 4g

Dimethyl (7-{[(1R)-1-(hydroxymethyl)-3-methylbutyl]amino}-5-{[(1S)-1-phenylethyl]sulfanyl}[1,3]thiazolo[4,5-d]pyrimidin-2-yl)amidophosphate

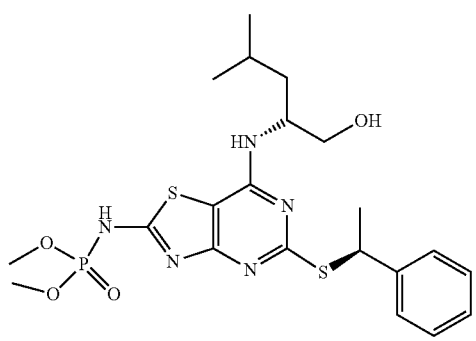

The title product was synthesized from (2R)-2-[(2-amino-5-{[(1S)-1-phenylethyl]sulfanyl}-[1,3]thiazolo[4,5-d]pyrimidin-7-yl)amino]-4-methylpentan-1-ol hydrochloride (Karlström S., et al., *J. Med. Chem.*, 2013, 56, 3177-3190; WO 2006/107258) in two steps, using the method described for Example 4 with the exception that MeOH, instead of water and DMSO, was added after 1 h at ice-bath temperature in step 2.

The starting material for step 2 was the same as in Example 4. Overall yield for two steps: 75%.

Step 2: $^1$H NMR (600 MHz, CD$_3$OD) $\delta_H$ ppm 7.43-7.47 (m, 2H) 7.29-7.33 (m, 2H) 7.22 (tt, J=7.4, 1.5 Hz, 1H) 5.04 (q, J=7.1 Hz, 1H) 4.50 (br. s., 1H) 3.76 (d, J=10.7 Hz, 6H) 3.55 (dd, J=11.0, 5.5 Hz, 1H) 3.49 (dd, J=11.0, 5.5 Hz, 1H) 1.73 (d, J=7.0 Hz, 3H) 1.66-1.75 (m, 1H) 1.52-1.58 (m, 1H) 1.44-1.50 (m, 1H) 0.97 (d, J=6.7 Hz, 3H) 0.94 (d, J=6.7 Hz, 3H). MS (ESI$^+$) m/z 512 [M+H]$^+$.

Example 4h

Diethyl (5-{[1-(2-chlorophenyl)ethyl]sulfanyl}-7-{[(1R)-1-(hydroxymethyl)-3-methylbutyl]amino}[1,3]thiazolo[4,5-d]pyrimidin-2-yl)amidophosphate

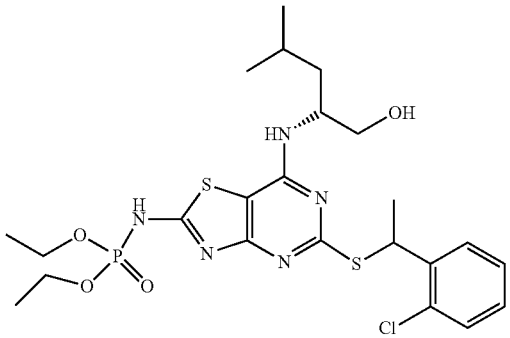

The title product was synthesized from (2R)-2-[(2-amino-5-{[1-(2-chlorophenyl)ethyl]sulfanyl}[1,3]thiazolo[4,5-d]pyrimidin-7-yl)amino]-4-methylpentan-1-ol (Karlström S., et al., *J. Med. Chem.*, 2013, 56, 3177-3190; WO 2006/107258) in two steps, using the method described for Example 4 with the exception that EtOH, instead of water and DMSO, was added after 1 h at ice-bath temperature in step 2.

The starting material for step 2 was the same as in Example 4b. The product is a mixture of two diastereomers. Overall yield for two steps: 73%.

Step 2: The two diastereomers were separated by preparatory HPLC (basic method).

Diastereomer A: $^1$H NMR (600 MHz, CD$_3$OD) $\delta_H$ ppm 7.64 (dd, J=7.6, 1.5 Hz, 1H) 7.41 (dd, J=7.9, 1.2 Hz, 1H) 7.30 (td, J=7.6, 1.4 Hz, 1H) 7.23 (td, J=7.8, 1.7 Hz, 1H) 5.50 (q, J=7.0 Hz, 1H) 4.50 (br. s., 1H) 4.08-4.16 (m, 4H) 3.48 (dd, J=11.0, 4.6 Hz, 1H) 3.39 (dd, J=11.3, 4.9 Hz, 1H) 1.70 (d, J=7.0 Hz, 3H) 1.67-1.75 (m, 1H) 1.59-1.66 (m, 1H) 1.41 (ddd, J=13.7, 9.2, 4.6 Hz, 1H) 1.34 (td, J=7.1, 1.7 Hz, 6H) 0.97 (d, J=6.7 Hz, 3H) 0.95 (d, J=6.7 Hz, 3H). MS (ESI$^+$) m/z 574 [M+H]$^+$.

Diastereomer B: $^1$H NMR (600 MHz, CD$_3$OD) $\delta_H$ ppm 7.63 (dd, J=7.8, 1.7 Hz, 1H) 7.39 (dd, J=7.9, 1.2 Hz, 1H) 7.30 (td, J=7.6, 1.2 Hz, 1H) 7.23 (td, J=7.8, 1.4 Hz, 1H) 5.50 (q, J=7.0 Hz, 1H) 4.45 (br. s., 1H) 4.08-4.16 (m, 4H) 3.64 (dd, J=11.3, 5.2 Hz, 1H) 3.58 (dd, J=11.0, 5.2 Hz, 1H) 1.74 (d, J=7.0 Hz, 3H) 1.63-1.69 (m, 1H) 1.56-1.63 (m, 1H) 1.38-1.44 (m, 1H) 1.34 (t, J=7.2 Hz, 6H) 0.93 (d, J=6.4 Hz, 3H) 0.83 (d, J=6.4 Hz, 3H). MS (ESI$^+$) m/z 574 [M+H]$^+$.

Example 4i

Diethyl (7-{[(1R)-1-(hydroxymethyl)-3-methyl-butyl]amino}-5-[(1-pyridin-2-ylethyl)sulfanyl][1,3]thiazolo[4,5-d]pyrimidin-2-yl)amidophosphate

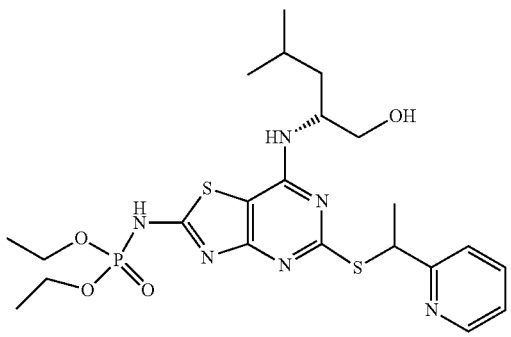

The title product was synthesized from (2R)-2-({2-amino-5-[(1-pyridin-2-ylethyl)sulfanyl][1,3]thiazolo[4,5-d]pyrimidin-7-yl}amino)-4-methylpentan-1-ol (Karlström S., et al., J. Med. Chem., 2013, 56, 3177-3190; WO 2006/107258) in two steps, using the method described for Example 4 with the exception that EtOH, instead of water and DMSO, was added after 1 h at ice-bath temperature in step 2.

The starting material for step 2 was the same as in Example 4c. The product is a mixture of two diastereomers. Overall yield for two steps: 31%.

Step 2: The two diastereomers were separated by preparatory HPLC (basic method).

Diastereomer A: $^1$H NMR (600 MHz, CD$_3$OD) $\delta_H$ ppm 8.47 (dt, J=4.9, 0.8 Hz, 1H) 7.79 (td, J=7.7, 1.4 Hz, 1H) 7.62 (d, J=7.3 Hz, 1H) 7.28 (dd, J=7.6, 4.9 Hz, 1H) 5.19 (q, J=7.3 Hz, 1H) 4.48 (br. s., 1H) 4.06-4.16 (m, 4H) 3.51 (dd, J=11.1, 5.3 Hz, 1H) 3.43 (dd, J=11.0, 5.5 Hz, 1H) 1.74 (d, J=7.3 Hz, 3H) 1.65-1.72 (m, 1H) 1.51-1.57 (m, 1H) 1.42-1.48 (m, 1H) 1.33 (t, J=7.0 Hz, 6H) 0.96 (d, J=6.4 Hz, 3H) 0.94 (d, J=6.7 Hz, 3H). MS (ESI$^+$) m/z 541 [M+H]$^+$.

Diastereomer B: $^1$H NMR (600 MHz, CD$_3$OD) $\delta_H$ ppm 8.47 (dd, J=5.1, 0.9 Hz, 1H) 7.78 (td, J=7.9, 1.8 Hz, 1H) 7.65 (d, J=7.9 Hz, 1H) 7.27-7.29 (m, 1H) 5.14 (q, J=7.3 Hz, 1H) 4.25 (br. s., 1H) 4.07-4.14 (m, 4H) 3.61 (dd, J=11.0, 5.2 Hz, 1H) 3.51 (dd, J=11.0, 5.8 Hz, 1H) 1.72 (d, J=7.3 Hz, 3H) 1.59-1.66 (m, 1H) 1.49-1.54 (m, 1H) 1.41-1.46 (m, 1H) 1.33 (t, J=7.0 Hz, 6H) 0.92 (d, J=6.4 Hz, 3H) 0.79 (d, J=6.7 Hz, 3H). MS (ESI$^+$) m/z 541 [M+H]$^+$.

Example 4j

Diethyl (5-{[1-(3-cyanophenyl)ethyl]sulfanyl}-7-{[(1R)-1-(hydroxymethyl)-3-methylbutyl]amino}[1,3]thiazolo[4,5-d]pyrimidin-2-yl)amidophosphate

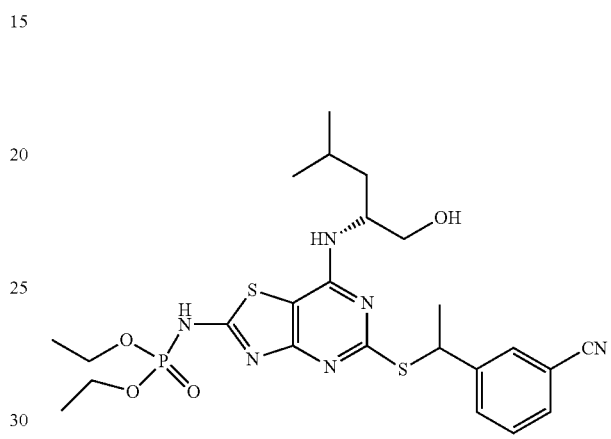

The title product was synthesized from 3-{1-[(2-amino-7-{[(1R)-1-(hydroxymethyl)-3-methylbutyl]amino}[1,3]thiazolo[4,5-d]pyrimidin-5-yl)sulfanyl]ethyl}benzonitrile (Karlström S., et al., J. Med. Chem., 2013, 56, 3177-3190; WO 2006/107258) in two steps, using the method described for Example 4 with the exception that EtOH, instead of water and DMSO, was added after 1 h at ice-bath temperature in step 2.

The starting material for step 2 was the same as in Example 4d. The product is a mixture of two diastereomers. Overall yield for two steps: 60%.

Step 2: The two diastereomers were separated by preparatory HPLC (basic method).

Diastereomer A: $^1$H NMR (600 MHz, CD$_3$OD) $\delta_H$ ppm 7.86 (t, J=1.7 Hz, 1H) 7.84 (dt, J=7.9, 1.4 Hz, 1H) 7.58 (dt, J=7.6, 1.4 Hz, 1H) 7.49 (t, J=7.8 Hz, 1H) 5.08 (q, J=7.2 Hz, 1H) 4.30 (br. s., 1H) 4.07-4.16 (m, 4H) 3.59 (dd, J=11.0, 5.5 Hz, 1H) 3.55 (dd, J=11.0, 5.8 Hz, 1H) 1.70 (d, J=7.3 Hz, 3H) 1.59-1.67 (m, 1H) 1.49-1.55 (m, 1H) 1.40-1.46 (m, 1H) 1.33 (td, J=7.1, 0.8 Hz, 6H) 0.92 (d, J=6.7 Hz, 3H) 0.80 (d, J=6.4 Hz, 3H). MS (ESI$^+$) m/z 565 [M+H]$^+$.

Diastereomer B: $^1$H NMR (600 MHz, CD$_3$OD) $\delta_H$ ppm 7.86 (t, J=1.7 Hz, 1H) 7.83 (dt, J=7.9, 1.4 Hz, 1H) 7.59 (dt, J=7.6, 1.4 Hz, 1H) 7.50 (t, J=7.8 Hz, 1H) 5.09 (q, J=7.2 Hz, 1H) 4.45 (br. s., 1H) 4.07-4.16 (m, 4H) 3.52 (dd, J=11.0, 5.2 Hz, 1H) 3.44 (dd, J=11.0, 5.5 Hz, 1H) 1.71 (d, J=7.3 Hz, 3H) 1.65-1.70 (m, 1H) 1.51-1.57 (m, 1H) 1.42-1.49 (m, 1H) 1.33 (t, J=7.0 Hz, 6H) 0.96 (d, J=6.7 Hz, 3H) 0.94 (d, J=6.4 Hz, 3H). MS (ESI$^+$) m/z 565 [M+H]$^+$.

Example 4k

Diethyl (5-{[1-(3-fluoropyridin-2-yl)ethyl]sulfanyl}-7-{[(1R)-1-(hydroxymethyl)-3-methylbutyl]amino}[1,3]thiazolo[4,5-d]pyrimidin-2-yl)amidophosphate

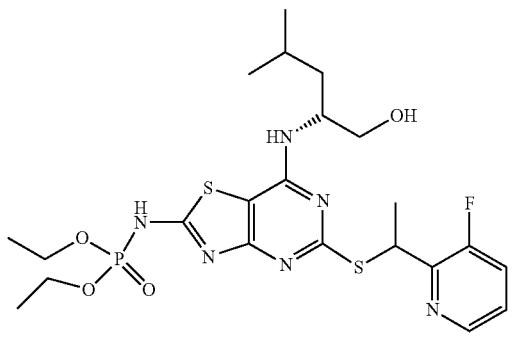

The title product was synthesized from (2R)-2-[(2-amino-5-{[1-(3-fluoropyridin-2-yl)ethyl]sulfanyl}[1,3]thiazolo[4,5-d]pyrimidin-7-yl)amino]-4-methylpentan-1-ol (Karlström S., et al., J. Med. Chem., 2013, 56, 3177-3190; WO 2006/107258) in two steps, using the method described for Example 4 with the exception that EtOH, instead of water and DMSO, was added after 1 h at ice-bath temperature in step 2.

The starting material for step 2 was the same as in Example 4e. The product is a mixture of two diastereomers. Overall yield for two steps: 56%.

Step 2: The two diastereomers were separated by preparatory HPLC (basic method).

Diastereomer A: $^1$H NMR (600 MHz, CD$_3$OD) $\delta_H$ ppm 8.34 (dt, J=4.9, 1.2 Hz, 1H) 7.60 (ddd, J=9.8, 8.5, 1.2 Hz, 1H) 7.37 (dt, J=8.5, 4.3 Hz, 1H) 5.56 (q, J=7.1 Hz, 1H) 4.52 (br. s., 1H) 4.07-4.17 (m, 4H) 3.57 (dd, J=11.0, 5.2 Hz, 1H) 3.53 (dd, J=11.0, 5.5 Hz, 1H) 1.76 (d, J=7.0 Hz, 3H) 1.67-1.74 (m, 1H) 1.55-1.61 (m, 1H) 1.46 (ddd, J=13.7, 9.2, 4.6 Hz, 1H) 1.34 (td, J=7.2, 1.8 Hz, 6H) 0.97 (d, J=6.7 Hz, 3H) 0.95 (d, J=6.7 Hz, 3H). MS (ESI$^+$) m/z 559 [M+H]$^+$.

Diastereomer B: $^1$H NMR (600 MHz, CD$_3$OD) $\delta_H$ ppm 8.35 (dt, J=4.9, 1.2 Hz, 1H) 7.59 (ddd, J=9.8, 8.4, 1.4 Hz, 1H) 7.37 (ddd, J=8.4, 4.4, 4.3 Hz, 1H) 5.55 (q, J=7.0 Hz, 1H) 4.48 (br. s., 1H) 4.08-4.16 (m, 4H) 3.61 (d, J=5.5 Hz, 2H) 1.78 (d, J=7.0 Hz, 3H) 1.67-1.74 (m, 1H) 1.54-1.61 (m, 1H) 1.43-1.50 (m, 1H) 1.34 (t, J=7.0 Hz, 6H) 0.97 (d, J=6.4 Hz, 3H) 0.92 (d, J=6.4 Hz, 3H). MS (ESI$^+$) m/z 559 [M+H]$^+$.

Example 5

Comparative Kinetic Solubility of Example 1 and Compound A

Samples of the compound of Example 1 and (2R)-2-[(2-amino-5-{[(1S)-1-phenylethyl]sulfanyl}-[1,3]thiazolo[4,5-d]pyrimidin-7-yl)amino]-4-methylpentan-1-ol. HCl (compound A) were diluted to a nominal concentration of 250 µM in 50 mM phosphate buffer pH 7.4 then agitated for 1 hour and filtered.

Standard solutions of the two compounds at concentrations of 25 and 250 µM in 50:50 acetontrile:water were prepared.

The solutions were then analysed by reverse phase HPLC with UV-detection, and solubility was determined by the ratio of the sample peaks to the standard curve. The results are shown in the Table below.

| Compound | Solubility (µM) |
|---|---|
| Example 1 (diammonium salt) | 118 |
| Compound A (HCl salt) | 5 |

Example 6

Comparative Stability of Solutions of Example 1 and Compound A

An aqueous solution of the compound of Example 1 (diammonium salt) was prepared in MilliQ water at a concentration of 1.7 mg/mL and the stability of the compound to long-term storage in aqueous solution was assessed by analysis of the solution by HPLC-MS over an extended time period.

The results of this study are shown in Table 1

TABLE 1

Stability of Example 1 in aqueous solution (1.7 mg/mL) at room temperature (RT)

| Entry | Days of storage | Example 1 % area |
|---|---|---|
| 1 | 0 | 99.6 |
| 2 | 4 | 99.6 |
| 3 | 13 | 99.6 |
| 4 | 20 | 99.6 |
| 5 | 40 | 99.6 |

It was not possible to dissolve the Compound A in pure water, so a number of solutions with various co-solvents were prepared, and the stability of the compound to long-term storage in aqueous solution was assessed by analysis of the solution by HPLC-MS over an extended time period. The results of these experiments are shown in Tables 2 to 4.

TABLE 2

Stability of Compound A in water + 20% MeOH (1.75 mg/mL) at RT

| Entry | Days | Compound A % area |
|---|---|---|
| 1 | 0 | 98.4% |
| 2 | 4 | 96.7% |

Table 3 shows the stability of Compound A in aqueous solution containing various amounts of the compound and added poly ethylene glycol.

TABLE 3

Stability of Compound A in water containing various amounts of polyethylene glycol at RT

| Entry | Days | Compound A (1.22 mg/mL) | Compound A (2.25 mg/mL) | Compound A (1.18 mg/mL) |
|---|---|---|---|---|
| Polyethylene glycol conc. (v/v) | | 24% | 26% | 24% |
| 1 Compound A remaining % | 0 | 98.6 | 98.5 | 98.5 |
| 2 Compound A remaining % | 3 | 98.0 | 97.7 | 97.7 |
| 3 Compound A remaining % | 56 | 31 | 35 | 28 |

Table 3 shows the stability of Compound A in aqueous solution containing various amounts of the compound and added polyethylene glycol and ethanol.

TABLE 4

Stability of Compound A in water containing poly ethylene glycol and ethanol at RT

| Entry | Days | Compound A (3.2 mg/mL) | Compound A (4.0 mg/mL) |
|---|---|---|---|
| polyethylene conc. (v/v) | | 28% | 25% |
| Ethanol (v/v) | | 0 | 3% |
| 1 Compound A remaining % | 0 | 98.4 | 98.4 |
| 2 Compound A remaining % | 14 | 88.1 | 92.3 |
| 3 Compound A remaining % | 70 | 60.7 | 75.1 |

Aqueous formulations of compound A required additional co-solvents, such as polyethylene glycol and/or ethanol to solubilize the compound. These formulations proved to be unstable to storage at room temperature, and relatively fast degradation of the compound was observed. In contrast, Example 1, showed not only an improved aqueous solubility (no co-solvents required), but also an unexpectedly pronounced stability over Compound A in aqueous solutions.

The major degradation products observed for Compound A were the debenzylated thiol and the corresponding disulfide together with phenyl ethanol and minor amounts of styrene.

A ⟶

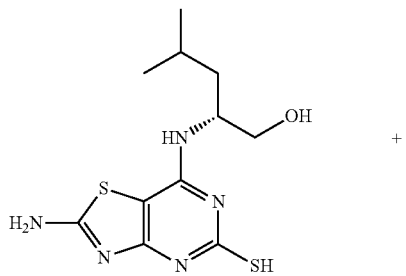

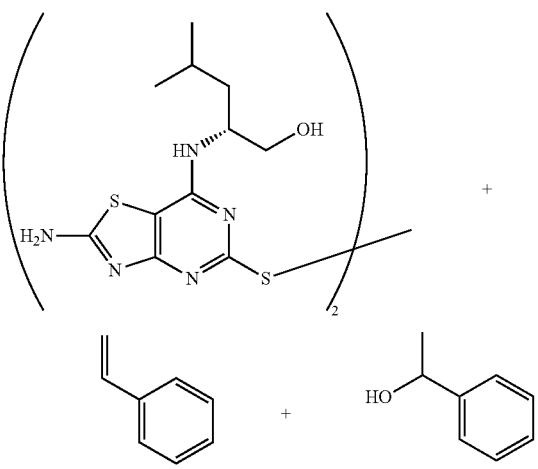

Surprisingly, these degradation products were not observed on storing Example 1 in aqueous solution.

Example 6

Further Stability Studies

Aqueous solutions of several of the example compounds were prepared at concentrations of 1.2 mg/mL (10 mg/mL for Example 1 (no salt)) according to the following procedures.

i) Examples 1 b, 2h and 3 (diammonium salts) were dissolved in pure water.

ii) Examples 1d (diammonium salt) and 1n (monoammonium salt) were suspended in water and $Na_2HPO_3$ was added until all of the compound was in solution.

iii) Examples 1q, 4f an 4g (no salts) were dissolved in water with added DMSO (100 μL) and (2-hydroxypropyl)-β-cyclodextrin was added until all of the compound was in solution.

The stability of the compounds to long-term storage in aqueous solution at room temperature and/or 40° C. was then assessed by analysis of the solution by HPLC-MS after 60 days.

TABLE 5

Stability of aqueous solutions after storage at room temperature for 60 days

| Example | % Area by HPLC (60 days) |
|---|---|
| 1b (diammonium salt) | 100 |
| 1d (diammonium salt) | 98.0 |
| 1n (monoammonium salt) | 98.2 |
| 1q | 63.1 |
| 2h (diammonium salt) | 92.3 |
| 3 (diammonium salt) | 99.6 |
| 4f | 95.7 |
| 4g | 91.6 |

TABLE 6

Stability of aqueous solutions after storage at room 40° C. for 60 days.

| Example | % Area by HPLC (60 days) |
|---|---|
| 1b (diammonium salt) | 100 |
| 1d (diammonium salt) | 99.7 |
| 1n (monoammonium salt) | 100 |
| 1q | 0 |
| 2h (diammonium salt) | 82.2 |
| 3 (diammonium salt) | 100 |
| 4f | 82.1 |
| 4g | 45.1 |
| 1 (10 mg/mL) | 100 |

These data show that compounds of the invention are generally stable to storage in aqueous solution, including under accelerated aging conditions at 40° C.

Example 7

Comparison of Plasma Concentration of Example 1 and Compound a in Mice after Intravenous and Peroral Administration Compound A A peroral dosing solution of Compound A (12 mg/mL) in 30% HP-β-CD in 10 mM Na$_2$PO$_4$ and an intravenous dosing solution of Compound A (2.5 mg/mL) in 30% HP-β-CD in 10 mM Na$_2$PO$_4$ in DPBS were prepared. The intravenous dosing solution was administered to male CD1 mice (weight 28-30 g) via intravenous injection (25 mg/kg) and the peroral dosing solution was administered to male CD1 mice (weight 28-30 g) via oral gavage (120 mg/kg).

Blood was collected from the animals at time points of 0.083, 0.25, 0.5, 1, 2, 4, 6, 12 and 24 hours and analysed for blood plasma concentration, and the data generated were used to calculate the area under the curve (AUC) values shown in Table 5.

Compound a Hydrochloride Salt

A peroral dosing solution of Compound A HCl salt (12 mg/mL) in 30% HP-β-CD in 10 mM Na$_2$PO$_4$ and an intravenous dosing solution of Compound A HCl salt (2.5 mg/mL) in 30% HP-β-CD in 10 mM Na$_2$PO$_4$ in DPBS were prepared. The intravenous dosing solution was administered to male CD1 mice (weight 28-30 g) via intravenous injection (25 mg/kg) and the peroral dosing solution was administered to male CD1 mice (weight 28-30 g) via oral gavage (125 mg/kg).

Blood was collected from the animals at time points of 0.083, 0.25, 0.5, 1, 2, 4, 6, 12 and 24 hours and analysed for blood plasma concentration, and the data generated were used to calculate the area under the curve (AUC) values shown in Table 5.

Example 1 Disodium Salt

A peroral dosing solution of Example 1 disodium salt in water (15.4 mg/mL) at a pH of 7.18 and an intravenous dosing solution of Example 1 disodium salt in water (6.4 mg/mL) at a pH of 7.11 were prepared by dissolving Example 1 diammonium salt in water and adjusting the pH with 0.1M NaOH solution. The intravenous dosing solution was administered to male CD1 mice (weight 24-25 g) via tail injection (32 mg/kg) and the peroral dosing solution was administered to male CD1 mice (weight 24-25 g) via oral gavage (154 mg/kg).

Blood was collected from the animals at time points of 0.083, 0.25, 0.5, 1, 2, 4, 6, 12 and 24 hours and analysed for blood plasma concentration, and the data generated were used to calculate the area under the curve (AUC) values shown in Table 5.

TABLE 5

Comparison of blood plasma concentration area under the curve for Compound A and Example 1.

| | | | | Plasma Compound A | |
|---|---|---|---|---|---|
| Administered compound | | | | | AUC dose |
| ID | Route | Dose (mg/kg) | Dose (mol/kg) | AUC (hr*μM) | adjusted (hr*μM) |
| Compound A | IV | 25 | 62 | 45.92 | 0.74 |
| Compound A •HCl | | 25 | 57 | 50.07 | 0.88 |
| Example 1 •2Na | | 32 | 62 | 55.44 | 0.90 |
| Compound A | PO | 120 | 297 | 92.57 | 0.31 |
| Compound A •HCl | | 125 | 284 | 170.19 | 0.60 |
| Example 1 •2Na | | 154 | 298 | 230.80 | 0.78 |

The invention claimed is:

1. A compound (2R)-2-[(2-Amino-5-{[(1S)-1-phenyl-ethyl]sulfanyl}[1,3]thiazolo[4,5-d]pyrimidin-7-yl)amino]-4-methylpentyl dihydrogen phosphate,

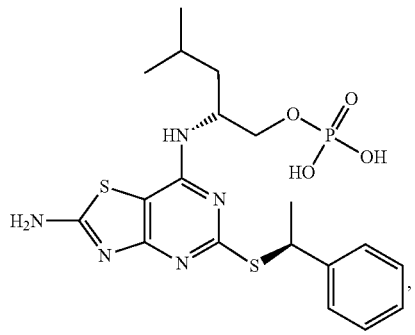

or a pharmaceutically acceptable salt thereof.

2. The compound as claimed in claim 1, wherein the pharmaceutically acceptable salt is a base addition salt.

3. The compound as claimed in claim 1, wherein the pharmaceutically acceptable salt is an ammonium salt or an alkali metal salt.

4. The compound as claimed in claim 1, wherein the compound is in the form of a base addition salt.

5. The compound as claimed in claim 1, wherein the compound is in the form of an ammonium salt or an alkali metal salt.

6. A pharmaceutical composition comprising a compound as defined in claim 1, including pharmaceutically acceptable salts thereof, in admixture with one or more pharmaceutically acceptable excipient.

7. The pharmaceutical composition as claimed in claim 6, wherein the composition further comprises water and less than 20% (w/w) solubilising excipients.

8. The pharmaceutical composition as claimed in claim 7, wherein the composition is in the form of an aqueous solution.

9. The pharmaceutical composition as claimed in claim 6, wherein the composition is in the form of a powder.

10. A method of treating and/or preventing a disease or disorder associated with elevated levels of CX3CR1 and/or CX3CL1 comprising administering to a patient in need thereof, a therapeutically effective amount of a compound as defined in claim 1, including pharmaceutically-acceptable salts thereof, wherein the disease or disorder is selected from the group consisting of acute and/or chronic inflammation, a cardiovascular disease, an autoimmune disease, a gastrointestinal disease and pain.

11. The method as claimed in claim 10, wherein the disease or disorder is arteriosclerosis.

12. The method as claimed in claim 10, wherein the disease or disorder is myocardial infarction.

13. The method as claimed in claim 10, wherein the disease or disorder is multiple sclerosis.

14. The method as claimed in claim 10, wherein the disease or disorder is pancreatitis.

15. The method as claimed in claim 10, wherein the disease or disorder is chemotherapy-induced pain.

16. The method as claimed in claim 10, wherein the disease or disorder is neuropathic pain.

17. A combination product comprising:
   (I) a compound as defined in claim 1, or a pharmaceutically acceptable salt thereof; and
   (II) one or more other therapeutic agent that is useful in the treatment and/or prevention of a disease or disorder associated with elevated levels of CX3CR1 and/or CX3CL1, wherein the disease or disorder is selected from acute and/or chronic inflammation, a cardiovascular disease, an autoimmune disease, a gastrointestinal disease and pain,
wherein each of components (I) and (II) is formulated in admixture, optionally with a pharmaceutically-acceptable excipient.

* * * * *